(12) United States Patent
McCreedy

(10) Patent No.: US 10,632,193 B2
(45) Date of Patent: *Apr. 28, 2020

(54) NANOPARTICLE COMPOSITIONS AND METHODS FOR IMMUNOTHERAPY

(71) Applicant: NexImmune, Inc., Gaithersburg, MD (US)

(72) Inventor: Bruce McCreedy, Gaithersburg, MD (US)

(73) Assignee: NEXIMMUNE, INC., Gaithersburg, MD (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/537,773

(22) PCT Filed: Dec. 24, 2015

(86) PCT No.: PCT/US2015/000340
§ 371 (c)(1),
(2) Date: Jun. 19, 2017

(87) PCT Pub. No.: WO2016/105542
PCT Pub. Date: Jun. 30, 2016

(65) Prior Publication Data
US 2019/0022215 A1  Jan. 24, 2019

Related U.S. Application Data

(60) Provisional application No. 62/096,725, filed on Dec. 24, 2014.

(51) Int. Cl.
*A61K 39/39* (2006.01)
*A61K 39/395* (2006.01)
*C07K 16/28* (2006.01)
*A61K 39/00* (2006.01)
*A61K 47/69* (2017.01)
*C07K 14/74* (2006.01)

(52) U.S. Cl.
CPC .... *A61K 39/39533* (2013.01); *A61K 39/0011* (2013.01); *A61K 39/39* (2013.01); *A61K 39/395* (2013.01); *A61K 47/6937* (2017.08); *C07K 14/70539* (2013.01); *C07K 16/2818* (2013.01); *A61K 2039/55555* (2013.01); *A61K 2039/6093* (2013.01); *C07K 2317/14* (2013.01); *C07K 2317/24* (2013.01); *C07K 2317/52* (2013.01); *C07K 2317/53* (2013.01); *C07K 2319/00* (2013.01)

(58) Field of Classification Search
None
See application file for complete search history.

(56) References Cited

U.S. PATENT DOCUMENTS

| 6,797,514 | B2 | 9/2004 | Berenson et al. |
| 6,867,041 | B2 | 3/2005 | Berenson et al. |
| 6,908,874 | B2 | 6/2005 | Berenson et al. |
| 8,354,110 | B2 | 1/2013 | Santamaria et al. |
| 8,629,098 | B2 | 1/2014 | Fahmy et al. |
| 9,511,151 | B2 | 12/2016 | Santamaria |
| 10,124,045 | B2 | 11/2018 | Santamaria |
| 2004/0115216 | A1 | 6/2004 | Schneck et al. |
| 2007/0003547 | A1 | 1/2007 | Foote |
| 2009/0017000 | A1 | 1/2009 | Cal et al. |
| 2010/0028450 | A1 | 2/2010 | Vasu |
| 2010/0129392 | A1 | 5/2010 | Shi et al. |
| 2010/0284965 | A1* | 11/2010 | Fahmy .................. A61K 39/39 424/85.2 |
| 2012/0039899 | A1 | 2/2012 | Olsen et al. |
| 2013/0309250 | A1* | 11/2013 | Cogswell ........... C07K 16/2827 424/172.1 |
| 2016/0051698 | A1 | 2/2016 | Schneck et al. |
| 2016/0129133 | A1 | 5/2016 | McCreedy et al. |
| 2017/0246277 | A1 | 8/2017 | Schneck et al. |

FOREIGN PATENT DOCUMENTS

| WO | 2010/042555 | 4/2010 |
| WO | 2013086500 | 6/2013 |
| WO | 2013090804 | 6/2013 |
| WO | 2014/052545 | 4/2014 |

OTHER PUBLICATIONS

Webster (Nature, 13:883-884, published online: Oct. 27, 2014).*
Cheng et al. (Biomaterials, 28: 869-876, 2008).*
Purkiss et al. (Langmuir, 19: 8428-8435, 2003).*
Gref, et all, "'Stealth' Corona-Core Nanoparticles Surface Modified by Polyethylene Glycol (PEG): Influences of the Corona (PEG Chain Length and Surface Density) and of the Core Composition on Phagocytic Uptake and Plasma Protein Adsorption", Colloids and Surfaces B: Biointerfaces vol. 18, Issues 3-4, Oct. 2000, pp. 301-313.
Gadad et al., "Study of Different Properties and Applications of Poly Lactic-CO-Glycolic Acid (PLFA) Nanotechnology: An Overview", Indian Drugs 49(12):5-22—Dec. 2012.
Im, et al., "Defining CD8+ T cells that provide the proliferative burst after PD-1 therapy", Nature. Sep. 15, 2016; 537(7620): 417-421.
Kamphorst, et al., "Rescue of exhausted CD8 T cells by PD-1 targeted therapies is CD28-dependent", Science. Mar. 31, 2017; 355(6332): 1423-1427.

(Continued)

*Primary Examiner* — Nelson B Moseley, II

(74) *Attorney, Agent, or Firm* — Morgan, Lewis & Bockius LLP

(57) ABSTRACT

The present invention provides compositions and methods for immunotherapy, which include shelf-stable pharmaceutical compositions for inducing antigen-specific T cells. Such compositions are employed as components of an artificial antigen presenting cell (aAPC), to provide a patient with complexes for presentation of an antigen (e.g., a tumor antigen) and/or a T cell co-stimulatory molecule.

28 Claims, 39 Drawing Sheets

Specification includes a Sequence Listing.

(56) References Cited

OTHER PUBLICATIONS

Perica, et al., "Nanoscale artificial antigen presenting cells for T cell immunitherapy", Nanomedicine, Epub. Jul. 24, 2013, vol. 10 No. 1 pp. 119-129.

Perica, et al., "Enrichment and Expansion with Nano-Artificial Antigen Presenting Cells for Adoptive Immunotherapy", ACS Nano. Jul. 28, 2015; 9(7): 6861-6871.

Perica et al., "Magnetic Field-Induced T Cell Receptor Clustering by Nanoparticles Enhances T Cell Activation and Stimulates Antitumor Activity", ACS Nano, 2014, vol. 8, No. 3, pp. 2252-2260.

Oelke et al. "Ex vivo induction and expansion of antigen-specific cytotoxic T cells by HLA-Ig-coated artificial antigen-presenting cells," Nat Med., 2003, vol. 9, pp. 619-624.

Betancourt, et al., "PEGylation Strategies for Active Targeting of PLA/PLGA Nanoparticles", Journal of Biomedical Materials Research Part A, 2008, pp. 263-276.

\* cited by examiner

Anti-CD28 VH2 Sequences

```
        10        20        30        40        50        60        70        80        90       100
GAGGTGAAGCTGCAGCAGTCAGGACCTGGCCTGGTGAAGCCCTCAGAGACCCTGTCCCTCACTTGTACTGTCTCTGGGTTTTCATTAAGCGACTATGGTG
 E  V  K  L  Q  Q  S  G  P  G  L  V  K  P  S  E  T  L  S  L  T  C  T  V  S  G  F  S  L  S  D  Y  G
                            10                            20                            30

110       120       130       140       150       160       170       180       190       200
TTCATTGGGTTCGCCAGGCTCCAGGAAAGGGACTGGAGTGGCTGGGAGTAATATGGGCTGGTGGAGGCACGAATTATAATTCGGCTCTCATGTCCAGAAA
V  H  W  V  R  Q  A  P  G  K  G  L  E  W  L  G  V  I  W  A  G  G  G  T  N  Y  N  S  A  L  M  S  R  K
                40                            50                            60

210       220       230       240       250       260       270       280       290       300
GACCATCAGCAAAGACAACTCCAAGAGCCAAGTTTCCTTAAAAATGAGCAGTGTGACAGCTGCTGACACAGCCGTGTATTACTGTGCCAGAGATAAGGGA
  T  I  S  K  D  N  S  K  S  Q  V  S  L  K  M  S  S  V  T  A  A  D  T  A  V  Y  Y  C  A  R  D  K  G
     70                            80    82  A  B  C                          90

310       320       330       340       350       360
TACTCCTATTACTATTCTATGGACTACTGGGGCCAAGGCACCCTGGTCACCGTCTCCTCA
 Y  S  Y  Y  Y  S  M  D  Y  W  G  Q  G  T  L  V  T  V  S  S
    100  A  B  C  D                           110
```

CDR definitions and protein sequence numbering according to Kabat. CDR nucleotide and protein sequences are highlighted in red

FIGURE 3

Anti-CD28 VH3 Sequences

*[Illegible sequence data]*

CDR definitions and protein sequence numbering according to Kabat. CDR nucleotide and protein sequences are highlighted in red.

FIGURE 4

Anti-CD28 VK1 Sequences

```
        10        20        30        40        50        60        70        80        90        10
GACATCGAGCTCACTCAGTCTCCAGATTCTTTGGCTGTGTCTCTAGGGGAGAGAGCCACCATCAACTGCAGAGCCAGTGAGAGTGTTGAATATTATGTC
 D  I  E  L  T  Q  S  P  D  S  L  A  V  S  L  G  E  R  A  T  I  N  C  R  A  S  E  S  V  E  Y  Y  V
                           10                            20                      27  A  B  C  D 110       120       130       140       150       160       170       180       190       20
CAAGTTTAATGCAGTGGTACCAGCAGAAAGCCAGGACAGCCACCCAAACTCCTCATCTTTGCTGCATCCAACGTAGAATCTGGGGTCCCTGACAGGTTTA
 T  S  L  M  Q  W  Y  Q  Q  K  P  G  Q  P  P  K  L  L  I  F  A  A  S  N  V  E  S  G  V  P  D  R  F
30                            40                            50                            60

210       220       230       240       250       260       270       280       290       30
TGGCAGTGGGTCTGGGACAAACTTCACCCTCACCATCTCTTCTCTGCAGGAGGAGGATGTTGCAATGTATTTCTGTCAGCAAAGTAGGAAGGTTCCTTA
  G  S  G  S  G  T  N  F  T  L  T  I  S  S  L  Q  E  E  D  V  A  M  Y  F  C  Q  Q  S  R  K  V  P  Y
                     70                            80                            90

310       320       330
ACGTTCGGAGGGGGGACCAAGGTGGAAATAAAA
 T  F  G  G  G  T  K  V  E  I  K
                           110
```

CDR definitions and protein sequence numbering according to Kabat. CDR nucleotide and protein sequences are highlighted in red

Anti-CD28 VK3 Sequences

```
         10        20        30        40        50        60        70        80        90       100
GACATCGAGCTCACTCAGTCTCCAGATTCTTTGGCTGTGTCTCTAGGGGAGAGAGCCACCATCAACTGCAGAGCCAGTGAGAGTGTTGAATATTATGTCA
 D  I  E  L  T  Q  S  P  D  S  L  A  V  S  L  G  E  R  A  T  I  N  C  R  A  S  E  S  V  E  Y  Y  V
                              10                            20                      27  A  B  C  D 110       120       130       140       150       160       170       180       190       200
CAAGTTTAATGCAGTGGTACCAGCAGAAGCCAGGACAGCCACCCAAACTCCTCATCTTTGCTGCATCCAACGTAGAATCTGGGGTCCCTGACAGGTTTAG
T  S  L  M  Q  W  Y  Q  Q  K  P  G  Q  P  P  K  L  L  I  F  A  A  S  N  V  E  S  G  V  P  D  R  F  S
30                            40                            50                            60

210       220       230       240       250       260       270       280       290       300
TGGCAGTGGGTCTGGGACAGACTTCACCCTCACCATCTCTTCTCTGCAGGCGGAGGATGTTGCAATGTATTTCTGTCAGCAAAGTAGGAAGGTTCCTTAC
  G  S  G  S  G  T  D  F  T  L  T  I  S  S  L  Q  A  E  D  V  A  M  Y  F  C  Q  Q  S  R  K  V  P  Y
                         70                            80                            90

310       320       330
ACGTTCGGAGGGGGGACCAAGGTGGAAATAAAA
 T  F  G  G  G  T  K  V  E  I  K
                           110
```

CDR definitions and protein sequence numbering according to Kabat. CDR nucleotide and protein sequences are highlighted in red

Constant κ light

FIGURE 9

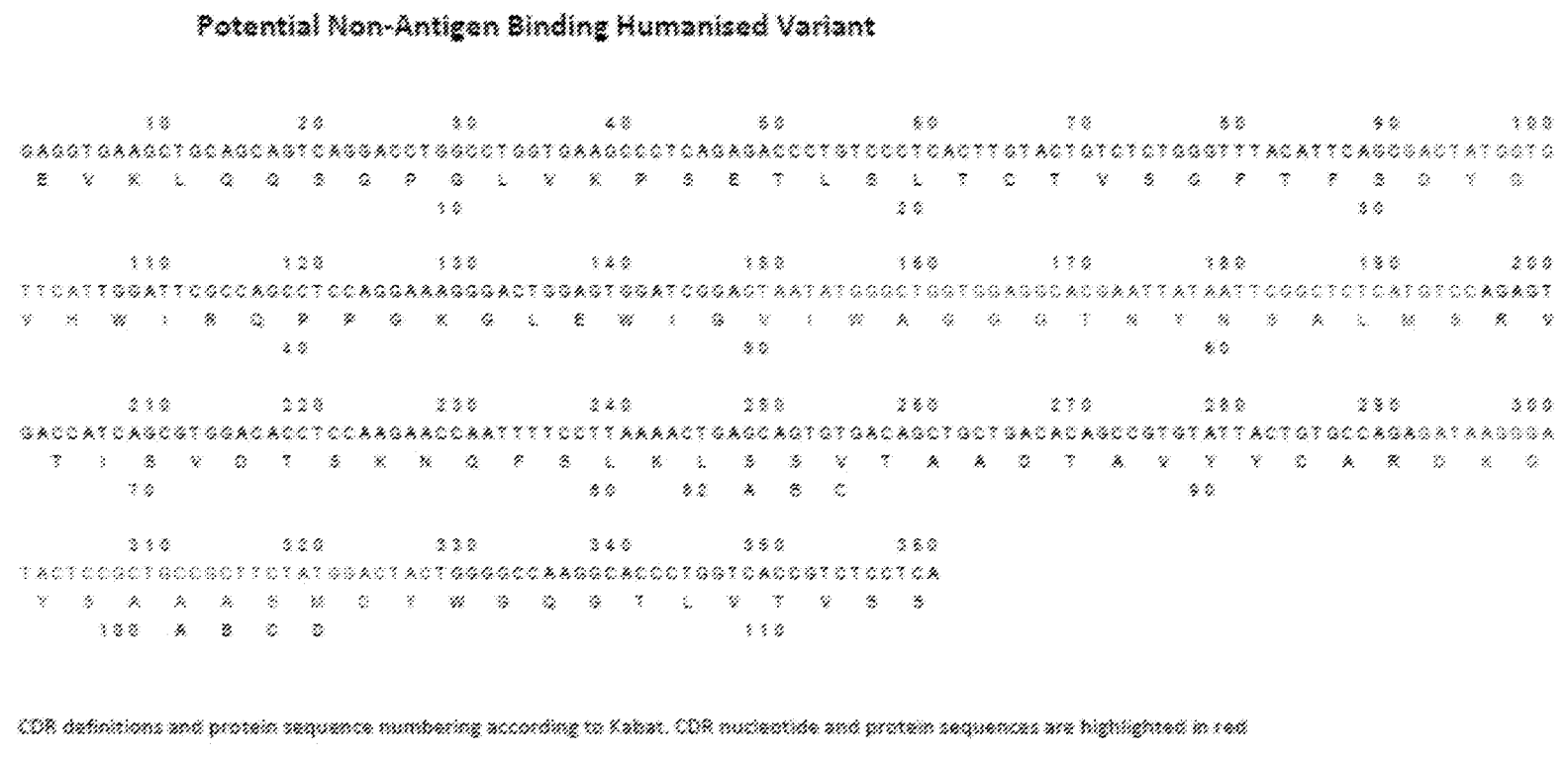

Potential Non-Antigen Binding Humanised Variant

CDR definitions and protein sequence numbering according to Kabat. CDR nucleotide and protein sequences are highlighted in red.

FIGURE 10

```
Gln Val Gln Leu Thr Arg Glu Gly Ser Gly Ser His Ser Met Arg Tyr
1               5                   10                  15

Phe Phe Thr Ser Val Ser Arg Pro Gly Arg Gly Glu Pro Arg Phe Ile
                20                  25                  30

Ala Val Gly Tyr Val Asp Asp Thr Gln Phe Val Arg Phe Asp Ser Asp
            35                  40                  45

Ala Ala Ser Gln Arg Met Glu Pro Arg Ala Pro Trp Ile Glu Gln Glu
        50                  55                  60

Gly Pro Glu Tyr Trp Asp Gly Glu Thr Arg Lys Val Lys Ala His Ser
65                  70                  75                  80

Gln Thr His Arg Val Asp Leu Gly Thr Leu Arg Gly Tyr Tyr Asn Gln
                85                  90                  95

Ser Glu Ala Gly Ser His Thr Val Gln Arg Met Tyr Gly Cys Asp Val
            100                 105                 110

Gly Ser Asp Trp Arg Phe Leu Arg Gly Tyr His Gln Tyr Ala Tyr Asp
        115                 120                 125

Gly Lys Asp Tyr Ile Ala Leu Lys Glu Asp Leu Arg Ser Trp Thr Ala
    130                 135                 140

Ala Asp Met Ala Ala Gln Thr Thr Lys His Lys Trp Glu Ala Ala His
145                 150                 155                 160

Val Ala Glu Gln Leu Arg Ala Tyr Leu Glu Gly Thr Cys Val Glu Trp
                165                 170                 175

Leu Arg Arg Tyr Leu Glu Asn Gly Lys Glu Thr Leu Gln Arg Thr Asp
            180                 185                 190

Ala Pro Lys Thr His Met Thr His His Ala Val Ser Asp His Glu Ala
        195                 200                 205

Thr Leu Arg Cys Trp Ala Leu Ser Phe Tyr Pro Ala Glu Ile Thr Leu
    210                 215                 220
```

FIGURE 10, continued

```
Thr Trp Gln Arg Asp Gly Glu Asp Gln Thr Gln Asp Thr Glu Leu Val
225                 230                 235                 240

Glu Thr Arg Pro Ala Gly Asp Gly Thr Phe Gln Lys Trp Ala Ala Val
                245                 250                 255

Val Val Pro Ser Gly Gln Glu Gln Arg Tyr Thr Cys His Val Gln His
            260                 265                 270

Glu Gly Leu Pro Lys Pro Leu Thr Trp Ala Arg Glu Val Ser Glu Val
            275                 280                 285

Lys Leu Gln Gln Ser Gly Pro Gly Leu Val Lys Pro Ser Glu Thr Leu
    290                 295                 300

Ser Leu Thr Cys Thr Val Ser Gly Phe Thr Phe Ser Asp Tyr Gly Val
305                 310                 315                 320

His Trp Ile Arg Gln Pro Pro Gly Lys Gly Leu Glu Trp Ile Gly Val
                325                 330                 335

Ile Trp Ala Gly Gly Gly Thr Asn Tyr Asn Ser Ala Leu Met Ser Arg
                340                 345                 350

Val Thr Ile Ser Val Asp Thr Ser Lys Asn Gln Phe Ser Leu Lys Leu
            355                 360                 365

Ser Ser Val Thr Ala Ala Asp Thr Ala Val Tyr Tyr Cys Ala Arg Asp
    370                 375                 380

Lys Gly Tyr Ser Ala Ala Ala Ser Met Asp Tyr Trp Gly Gln Gly Thr
385                 390                 395                 400

Leu Val Thr Val Ser Ser Ala Ser Thr Lys Gly Pro Ser Val Phe Pro
                405                 410                 415

Leu Ala Pro Cys Ser Arg Ser Thr Ser Glu Ser Thr Ala Ala Leu Gly
            420                 425                 430

Cys Leu Val Lys Asp Tyr Phe Pro Glu Pro Val Thr Val Ser Trp Asn
```

Ser Gly Ala Leu Thr Ser Gly Val His Thr Phe Pro Ala Val Leu Gln
        450                     455                 460

Ser Ser Gly Leu Tyr Ser Leu Ser Ser Val Val Thr Val Pro Ser Ser
465                     470                 475                 480

Ser Leu Gly Thr Lys Thr Tyr Thr Cys Asn Val Asp His Lys Pro Ser
                485                     490                 495

Asn Thr Lys Val Asp Lys Arg Val Glu Ser Lys Tyr Gly Pro Pro Cys
                500                     505                 510

Pro Pro Cys Pro Ala Pro Glu Phe Glu Gly Gly Pro Ser Val Phe Leu
            515                     520                 525

Phe Pro Pro Lys Pro Lys Asp Thr Leu Met Ile Ser Arg Thr Pro Glu
        530                     535                 540

Val Thr Cys Val Val Val Asp Val Ser Gln Glu Asp Pro Glu Val Gln
545                     550                 555                 560

Phe Asn Trp Tyr Val Asp Gly Val Glu Val His Asn Ala Lys Thr Lys
                565                     570                 575

Pro Arg Glu Glu Gln Phe Asn Ser Thr Tyr Arg Val Val Ser Val Leu
                580                     585                 590

Thr Val Leu His Gln Asp Trp Leu Asn Gly Lys Glu Tyr Lys Cys Lys
            595                     600                 605

Val Ser Asn Lys Gly Leu Pro Ser Ser Ile Glu Lys Thr Ile Ser Lys
        610                     615                 620

Ala Lys Gly Gln Pro Arg Glu Pro Gln Val Tyr Thr Leu Pro Pro Ser
625                     630                     635                 640

Gln Glu Glu Met Thr Lys Asn Gln Val Ser Leu Thr Cys Leu Val Lys
                645                     650                 655
```

FIGURE 10, continued

Gly Phe Tyr Pro Ser Asp Ile Ala Val Glu Trp Glu Ser Asn Gly Gln
            660                 665                 670

Pro Glu Asn Asn Tyr Lys Thr Thr Pro Pro Val Leu Asp Ser Asp Gly
        675                 680                 685

Ser Phe Phe Leu Tyr Ser Arg Leu Thr Val Asp Lys Ser Arg Trp Gln
    690                 695                 700

Glu Gly Asn Val Phe Ser Cys Ser Val Met His Glu Ala Leu His Asn
705                 710                 715                 720

His Tyr Thr Gln Lys Ser Leu Cys Leu Ser Leu Gly Lys
                725                 730

FIGURE 11

```
Asp Ile Glu Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25              30

Val Thr Ser Leu Met Gln Trp Tyr Gln Gln Lys Pro Gly Gln Pro Pro
            35                  40              45

Lys Leu Leu Ile Phe Ala Ala Ser Asn Val Glu Ser Gly Val Pro Asp
        50              55              60

Arg Phe Ser Gly Ser Gly Ser Gly Thr Asp Phe Thr Leu Thr Ile Ser
65              70              75                      80

Ser Leu Gln Ala Glu Asp Val Ala Met Tyr Phe Cys Gln Gln Ser Arg
            85                  90              95

Lys Val Pro Tyr Thr Phe Gly Gly Gly Thr Lys Val Glu Ile Lys Arg
            100             105             110

Thr Val Ala Ala Pro Ser Val Phe Ile Phe Pro Pro Ser Asp Glu Gln
            115             120             125

Leu Lys Ser Gly Thr Ala Ser Val Val Cys Leu Leu Asn Asn Phe Tyr
    130             135             140

Pro Arg Glu Ala Lys Val Gln Trp Lys Val Asp Asn Ala Leu Gln Ser
145             150             155                     160

Gly Asn Ser Gln Glu Ser Val Thr Glu Gln Asp Ser Lys Asp Ser Thr
            165             170             175

Tyr Ser Leu Ser Ser Thr Leu Thr Leu Ser Lys Ala Asp Tyr Glu Lys
            180             185             190

His Lys Val Tyr Ala Cys Glu Val Thr His Gln Gly Leu Ser Ser Pro
            195             200             205

Val Thr Lys Ser Phe Asn Arg Gly Glu Cys
    210             215
```

FIGURE 12

```
Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25              30

Gly Val His Trp Val Arg Gln Ala Pro Gly Lys Gly Leu Glu Trp Leu
            35                  40              45

Gly Val Ile Trp Ala Gly Gly Thr Asn Tyr Asn Ser Ala Leu Met
            50              55                  60

Ser Arg Lys Thr Ile Ser Lys Asp Asn Ser Lys Ser Gln Val Phe Leu
65              70                  75                  80

Lys Met Asn Ser Leu Thr Ala Ala Asp Thr Ala Val Tyr Tyr Cys Ala
                85                  90                  95

Arg Asp Lys Gly Tyr Ser Tyr Tyr Tyr Ser Met Asp Tyr Trp Gly Gln
                100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
                180                 185                 190

Ser Ser Ser Leu Gly Thr Lys Thr Tyr Thr Cys Asn Val Asp His Lys
        195                 200                 205

Pro Ser Asn Thr Lys Val Asp Lys Arg Val Glu Ser Lys Tyr Gly Pro
    210                 215                 220
```

FIGURE 12, continued

```
Pro Cys Pro Pro Cys Pro Ala Pro Glu Phe Glu Gly Gly Pro Ser Val
225             230              235              240

Phe Leu Phe Pro Pro Lys Pro Lys Asp Thr Leu Met Ile Ser Arg Thr
            245              250              255

Pro Glu Val Thr Cys Val Val Val Asp Val Ser Gln Glu Asp Pro Glu
            260              265              270

Val Gln Phe Asn Trp Tyr Val Asp Gly Val Glu Val His Asn Ala Lys
        275              280              285

Thr Lys Pro Arg Glu Glu Gln Phe Asn Ser Thr Tyr Arg Val Val Ser
    290              295              300

Val Leu Thr Val Leu His Gln Asp Trp Leu Asn Gly Lys Glu Tyr Lys
305             310              315              320

Cys Lys Val Ser Asn Lys Gly Leu Pro Ser Ser Ile Glu Lys Thr Ile
            325              330              335

Ser Lys Ala Lys Gly Gln Pro Arg Glu Pro Gln Val Tyr Thr Leu Pro
            340              345              350

Pro Ser Gln Glu Glu Met Thr Lys Asn Gln Val Ser Leu Thr Cys Leu
            355              360              365

Val Lys Gly Phe Tyr Pro Ser Asp Ile Ala Val Glu Trp Glu Ser Asn
    370              375              380

Gly Gln Pro Glu Asn Asn Tyr Lys Thr Thr Pro Pro Val Leu Asp Ser
385             390              395              400

Asp Gly Ser Phe Phe Leu Tyr Ser Arg Leu Thr Val Asp Lys Ser Arg
            405              410              415

Trp Gln Glu Gly Asn Val Phe Ser Cys Ser Val Met His Glu Ala Leu
            420              425              430

His Asn His Tyr Thr Gln Lys Ser Leu Cys Leu Ser Leu Gly Lys
            435              440              445
```

FIGURE 13

```
Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25              30

Gly Val His Trp Val Arg Gln Ala Pro Gly Lys Gly Leu Glu Trp Leu
            35                  40              45

Gly Val Ile Trp Ala Gly Gly Thr Asn Tyr Asn Ser Ala Leu Met
            50              55              60

Ser Arg Lys Thr Ile Ser Lys Asp Asn Ser Lys Ser Gln Val Ser Leu
65              70              75                          80

Lys Met Ser Ser Val Thr Ala Ala Asp Thr Ala Val Tyr Tyr Cys Ala
                85                  90              95

Arg Asp Lys Gly Tyr Ser Tyr Tyr Ser Met Asp Tyr Trp Gly Gln
            100             105             110

Gly Thr Leu Val Thr Val Ser Ser Ala Ser Thr Lys Gly Pro Ser Val
            115             120             125

Phe Pro Leu Ala Pro Cys Ser Arg Ser Thr Ser Glu Ser Thr Ala Ala
    130             135             140

Leu Gly Cys Leu Val Lys Asp Tyr Phe Pro Glu Pro Val Thr Val Ser
145             150             155                         160

Trp Asn Ser Gly Ala Leu Thr Ser Gly Val His Thr Phe Pro Ala Val
            165             170             175

Leu Gln Ser Ser Gly Leu Tyr Ser Leu Ser Ser Val Val Thr Val Pro
            180             185             190

Ser Ser Ser Leu Gly Thr Lys Thr Tyr Thr Cys Asn Val Asp His Lys
    195             200             205
```

FIGURE 13, continued

```
Pro Ser Asn Thr Lys Val Asp Lys Arg Val Glu Ser Lys Tyr Gly Pro
    210             215             220

Pro Cys Pro Pro Cys Pro Ala Pro Glu Phe Glu Gly Gly Pro Ser Val
225             230             235                         240

Phe Leu Phe Pro Pro Lys Pro Lys Asp Thr Leu Met Ile Ser Arg Thr
                245             250                 255

Pro Glu Val Thr Cys Val Val Val Asp Val Ser Gln Glu Asp Pro Glu
            260             265                 270

Val Gln Phe Asn Trp Tyr Val Asp Gly Val Glu Val His Asn Ala Lys
        275             280             285

Thr Lys Pro Arg Glu Glu Gln Phe Asn Ser Thr Tyr Arg Val Val Ser
    290             295             300

Val Leu Thr Val Leu His Gln Asp Trp Leu Asn Gly Lys Glu Tyr Lys
305             310             315                         320

Cys Lys Val Ser Asn Lys Gly Leu Pro Ser Ser Ile Glu Lys Thr Ile
                325             330                 335

Ser Lys Ala Lys Gly Gln Pro Arg Glu Pro Gln Val Tyr Thr Leu Pro
            340             345                 350

Pro Ser Gln Glu Glu Met Thr Lys Asn Gln Val Ser Leu Thr Cys Leu
        355             360             365

Val Lys Gly Phe Tyr Pro Ser Asp Ile Ala Val Glu Trp Glu Ser Asn
    370             375             380

Gly Gln Pro Glu Asn Asn Tyr Lys Thr Thr Pro Pro Val Leu Asp Ser
385             390             395                         400

Asp Gly Ser Phe Phe Leu Tyr Ser Arg Leu Thr Val Asp Lys Ser Arg
                405             410                 415
```

FIGURE 13, continued

Trp Gln Glu Gly Asn Val Phe Ser Cys Ser Val Met His Glu Ala Leu
            420                 425                 430

His Asn His Tyr Thr Gln Lys Ser Leu Cys Leu Ser Leu Gly Lys
        435                 440                 445

FIGURE 18
A
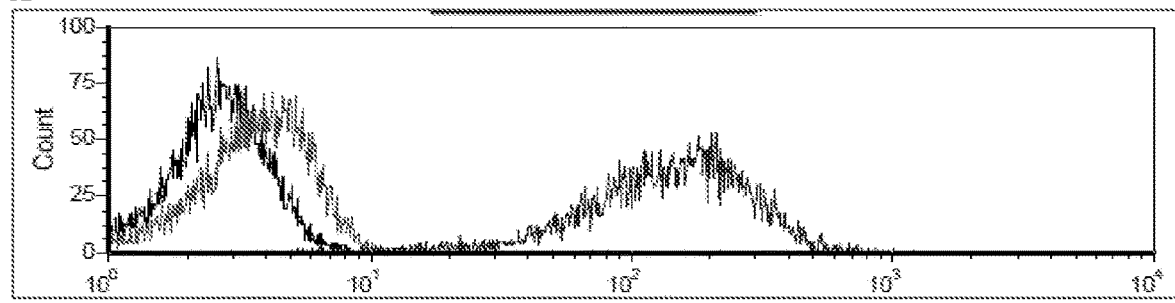
B
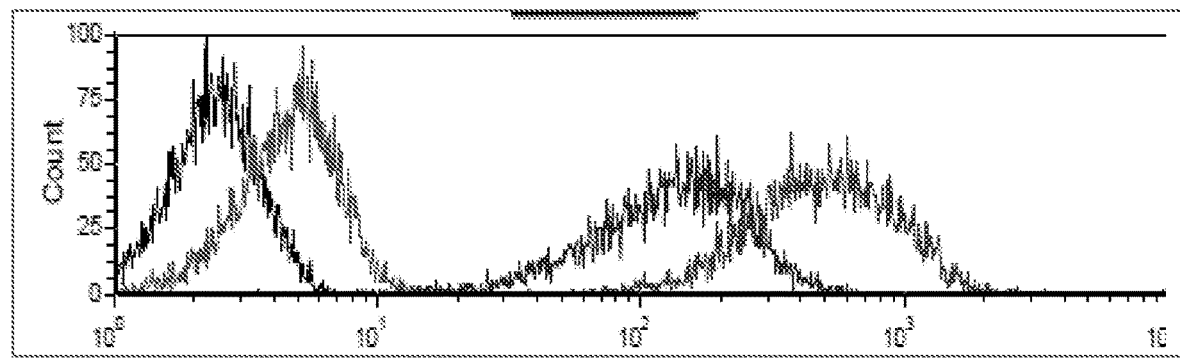

FIGURE 32

| Batch | Maleimide content (%w/w) | Average size (nm) | ζ (mV) | μg Prot input/mg NP | Coupling efficiency, % | # ligands/NP |
|---|---|---|---|---|---|---|
| ND19 | 5 | 91.8 | -8.7 | 51.5 | 41.6 | 45.8 |
| ND20 | 25 | 95.9 | -4.9 | 51.5 | 95.8 | 130.2 |
| ND21 | 55 | 98 | -3.1 | 51.5 | 93.5 | 125.2 |
| ND22 | 55 | 102 | -8.6 | 51.5 | 79.1 | 119 |
| ND3* | 0 | 68 | -9.2 | 51.5 | --- | --- |
| ND24 | 1 | 80.9 | -2.5 | 51.5 | 22.9 | 17.3 |
| ND25 | 10 | 92.9 | -5.8 | 51.5 | 67.2 | 76.8 |
| ND26 | 10 | 108 | -6.7 | 51.5 | 59.6 | 106.8 |

*Batch ND23 was used to determine the amount of proteins that absorbs nonspecifically to nanoparticles. The amount of protein absorbed nonspecifically was found < 3%.

NANOPARTICLE COMPOSITIONS AND METHODS FOR IMMUNOTHERAPY

REFERENCE TO PRIORITY APPLICATIONS

This application claims priority to U.S. Provisional Application No. 62/096,725 filed Dec. 24, 2014, which is hereby incorporated by reference in its entirety.

FIELD OF THE INVENTION

The present invention relates to nanoparticle compositions that present biological ligands for modulating the activity of immune cells.

BACKGROUND

An antigen-presenting cell (APC) is a cell that processes and displays antigenic peptides in complexes with major histocompatibility complex (MHC) proteins on their surfaces. Effector cells, such as T-cells, recognize these peptide-MHC (pMHC) complexes through cell-surface receptors, such as T-cell receptors (TCRs).

Dendritic cells (DCs) are an example of an antigen presenting cell that can be stimulated to effectively present antigen and support expansion of immune effector cells, thereby activating a cytotoxic response towards an antigen. In some immunotherapies, DCs are harvested from a patient and either pulsed with an antigen or transfected with a viral vector. Upon transfusion back into the patient these activated cells present tumor antigen to effector lymphocytes (e.g. $CD4^+$ T cells, $CD8^+$ T cells, and B cells). When successful, this therapy initiates a cytotoxic response against cells expressing antigens (including tumor antigens).

However, there remains a need for shelf-stable pharmaceutical compositions that are effective for immunotherapy, including antigen-specific immunotherapy for cancer. This disclosure meets these and other objectives.

BRIEF DESCRIPTION OF THE INVENTION

The present invention provides compositions and methods for immunotherapy, which include shelf-stable pharmaceutical compositions for inducing antigen-specific T cells in a patient. Such compositions are useful for the treatment of, for example, cancer and infectious disease. The composition in some aspects is an artificial antigen presenting cell (aAPC), which comprises a pharmaceutically acceptable bead or particle having antigen presenting complexes and optionally T cell co-stimulatory signals on its surface, to provide a patient with molecular complexes that present one or more antigens (e.g., tumor antigen(s)) in the proper context for activation of antigen-specific T cells (e.g., cytotoxic T cells). The bead or particles are designed to provide pharmacodynamic advantages, including circulating properties, biodistribution, degradation kinetics, as well as antigen-specific activation and/or expansion of naive and/or previously activated T cells. Physical parameters include size, surface charge, polydispersity index, polymer composition, ligand conjugation chemistry, ligand density, ligand ratio, among others. In some aspects, the invention provides nanoscale aAPCs (e.g., less than about 200 nm) that distribute to target tissues such as lymph nodes, spleen, and tumor sites. The nano-aAPC platform described herein can be fine tuned for various immunotherapy applications. In some embodiments, the aAPCs are in the range of about 20 nM to about 200 nM and can contain from 5 to about 1500 ligands per particle, including in some embodiments, less than about 150 ligands per particle, or less than about 100 ligands per particle, such as from about 5 to about 90 ligands per particle. In some embodiments, the nano aAPCs have (on average) less than about 150 ligands or less than about 100 ligands conjugated to their surface, thereby avoiding steric constraints from an abundance of ligands on the surface, without loss of activity and/or potency.

In some embodiments, the T-cell co-stimulatory signal is an anti-CD28 antibody or antigen-binding portion thereof, which may comprise human heavy chain amino acid sequences, including sequences selected from IgG, IgD, IgA, or IgM isotypes. In some embodiments, the immunoglobulin sequences include human IgG constant and variable sequences. The framework (FW) sequences may be modified to contain important or desired murine framework residues to maintain the integrity of the antigen-binding site(s). The complementarity determining regions (CDRs) may be based on a murine antibody amino acid sequence (e.g., 9.3 mAb), or other CD28 binding sequence, and which may bind a competing epitope with 9.3 mAb. In some embodiments, the antibody heavy chain is a variant of a human IGHV4 (e.g., IGHV4-59) germline FW. In some embodiments, the antibody comprises a light chain and the light chain is a variant of a human IGKV4-01 FW. The antibody may comprise a constant region, and the constant region is a human IgG4 constant region or variant thereof in some embodiments.

The co-stimulatory molecule may be conjugated to a solid support with antigen-presenting molecular complexes, to induce antigen-specific T cells. The antigen-presenting molecular complex may include MHC Class I and/or Class II complexes, or portions thereof comprising an antigen-binding cleft. In some embodiments, the molecular complex comprises one or more HLA amino acid sequences (e.g., comprises the extracellular domain of HLA or antigen-presenting portion thereof), which may contain additional sequences, such as immunoglobulin sequences, or other multimerizing (e.g., dimerizing) or stabilizing sequence. HLA-Ig dimerizing fusions in some embodiments provide advantages in stability, binding affinity, and/or T cell activation.

Thus, in some embodiments, the invention provides a bead- or particle-conjugated molecular complex for presentation of antigen to T cells, where the complex comprises an amino acid sequence forming a Class I or Class II antigen binding cleft, or portion thereof. The amino acid sequences of the antigen presenting complex may include fusions to heterologous sequences, to provide stability, affinity, and steric advantages, for example. In some embodiments, the heterologous sequences include immunoglobulin sequences. In some embodiments, the molecular complex includes HLA (e.g., HLA-A2) amino acid sequences fused to heterologous sequences, such as immunoglobulin sequences. In some embodiments, the immunoglobulin sequences comprise a human heavy chain immunoglobulin sequence (e.g., IGVH4), which can include immunoglobulin constant region sequences (e.g., comprising the hinge region) to provide dimeric HLA, and may optionally comprise variable region sequences. The variable region sequences if present can be optionally modified to reduce or eliminate potential antigen binding, and optionally with no murine FW residues. In some embodiments, the HLA antigen presenting complex is fused directly to the Ig hinge region (e.g, does not include light or heavy chain variable sequences). The HLA amino acid sequence may be HLA-A*02:01 (IMGT Accession No. HLA00005) or a derivative thereof.

The T cell co-stimulatory ligand and/or antigen presenting complexes (as well as other ligands disclosed herein, including targeting ligands) are conjugated to a particle support for ex vivo or in vivo antigen presentation and antigen-specific T cell activation. In some embodiments, the particle is formed of PLGA or PLA polymer core, with PLGA-PEG or PLA-PEG polymers. Alternatively, other polymers and/or co-polymers can be used. For example, the polymer may contain lactic acid (L) and glycolic acid (G) at a ratio of between 1:0 and 0:1, such as about 1:0 to about 1:1. In some embodiments, surface functional groups for coupling ligands are attached to the terminal end of PEG chains that form a hydrophilic sheath. The particles are designed to provide pharmacodynamic advantages, including circulating properties, biodistribution, and degradation kinetics, as well as high potency for activating antigen-specific T cells. Physical parameters include size, surface charge, polymer composition, ligand conjugation chemistry, ligand density, among others. For example, in some embodiments, the particles have a PLGA or PLA polymer core, and a hydrophilic shell formed by the PEG portion of the co-polymers, wherein a portion of the polymers have a terminal attachment of a polypeptide ligand. The hydrophilic shell comprises some PEG chains that are inert with respect to functional groups for ligand conjugation, such as PLGA-PEG-MeOH or PLA-PEG-MeOH polymers. In these embodiments, the particle chemistry allows good control of the ligand density.

In some embodiments, the particles are polymeric nanoparticles, such as the PLGA-PEG or PLA-PEG chemistry described in detail herein or other polymer chemistry, and have a size within the range of about 20 to about 200 nm. In some embodiments, the ligand density is controlled, such that there are from 5 to about 1500 ligands per particle (on average), and in some embodiments less than about 150 ligands per particle or less than about 100 ligands per particle (e.g., from about 5 to about 90 ligands per particle).

The pharmaceutical composition in the various embodiments may further comprise an antigenic peptide for presentation to T cells, and which may be co-formulated with the ligand-conjugated bead or particle. In various embodiments, the pharmaceutical composition is shelf stable, and may be provided in lyophilized form for reconstitution prior to administration, or alternatively provided in another convenient format for administration to patients (e.g., by parenteral administration).

The pharmaceutical compositions described herein are useful for immunotherapy, for example, in methods for inducing the formation of antigen-specific T cells, by administering an effective amount of the composition to a patient in need. In particular, antigen presenting platforms can be useful for treating patients with cancer, infectious diseases, or autoimmune diseases, or to provide prophylactic protection to immunosuppressed patients. In some embodiments, the nanoparticle compositions are administered after cancer immunotherapy, such as checkpoint inhibitor therapy and/or after adoptive T cell immunotherapy, and thereby provide enhanced and/or sustained immunological attack on a variety of cancers.

The invention further provides polynucleotides encoding the amino acid sequences described herein, as well as host cells expressing the same.

The details of the invention are set forth in the accompanying description and claims below. Although methods and materials similar or equivalent to those described herein can be used in the practice or testing of the present invention, illustrative methods and materials are now described. Other features, objects, and advantages of the invention will be apparent from the description and from the claims. In the specification and the appended claims, the singular forms also include the plural unless the context clearly dictates otherwise. Unless defined otherwise, all technical and scientific terms used herein have the same meaning as commonly understood by one of ordinary skill in the art to which this invention belongs.

BRIEF DESCRIPTION OF THE DRAWINGS

FIGS. 1-3 show three humanized variable heavy sequences for anti-CD28.

FIGS. 4-6 show three humanized variable light sequences for anti-CD28.

FIG. 7 shows a modified constant heavy sequence.

FIG. 8 shows a constant κ Light sequence.

FIG. 9 shows a humanized non-CD28-binding variable region for constructing an HLA fusion.

FIG. 10 shows the amino acid sequence for humanized HLA-IgG4HC.

FIG. 11 shows the amino acid sequence for Light Chain 3 (LC3, or Vκ3).

FIG. 12 shows the amino acid sequence for Heavy Chain 1 (HC1).

FIG. 13 shows the amino acid sequence for Heavy Chain 2 (HC2).

FIG. 18 shows that the humanized anti-CD28 clones specifically stain CD28 on a human T-cell line. FIG. 18(A): staining with murine anti-human CD8 mAb (clone 9.3, Isotype IgG2a); FIG. 18(B): staining with humanized anti-CD28 (isotype IgG4).

FIG. 32 lists properties of exemplary nanoparticle formulation batches.

DETAILED DESCRIPTION OF THE INVENTION

Figure 14:
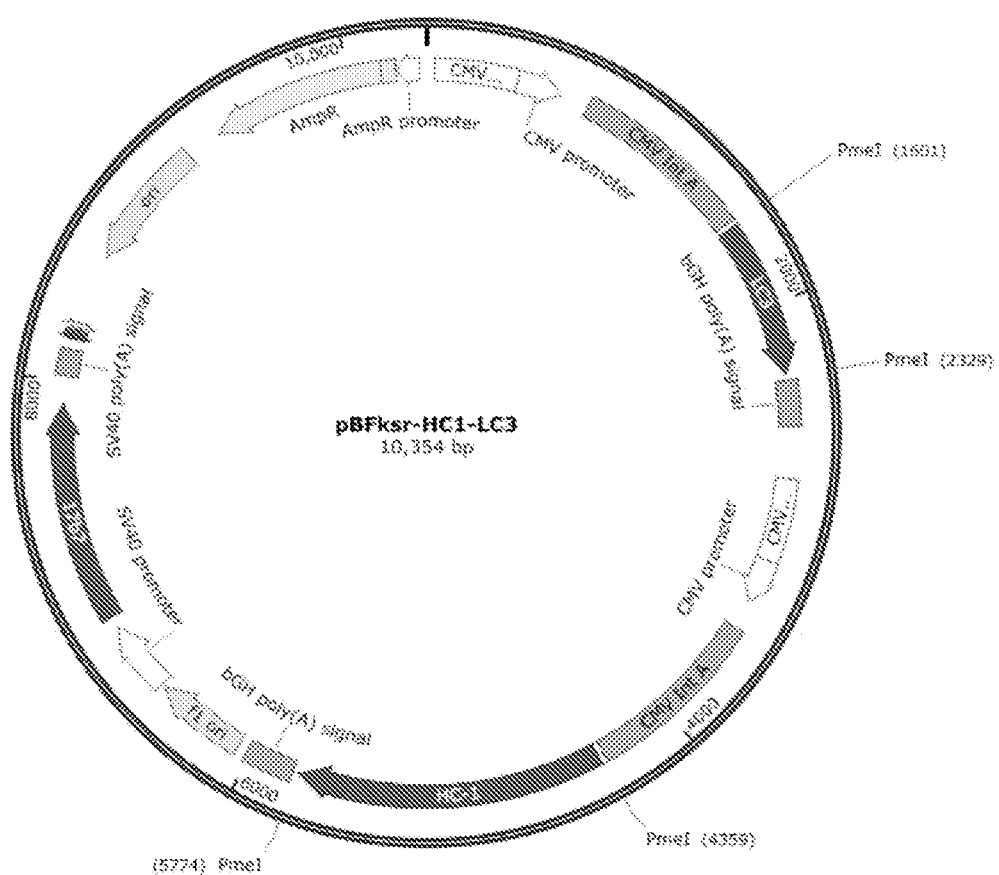
FIGS. 14-16 show expression constructs for expression in STABLEFAST-NS0 Cell Line.

The following abbreviations are used throughout: BLAST-Basic Local Ali Search Tool, CDR-Complementarity determining region, Cκ-Kappa light chain constant region, Fc-Antibody fragment crystallisable region, Fw-Framework region (of variable regions), HLA-Human leukocyte antigen, MHC-Major histocompatibility complex, VH-Variable heavy, Vκ-Variable kappa light, and V region-Variable region of an antibody, either VH or Vκ.

The present invention provides compositions and methods for immunotherapy, which include shelf-stable pharmaceutical compositions for inducing antigen-specific T cells in a patient. In some embodiments, the compositions comprise dimeric HLA antigen presenting complexes. In some embodiments, the compositions comprise humanized immunoglobulin sequences or portions thereof, which may be employed as components of the ligands on artificial antigen presenting cells (aAPCs), to provide a patient with dimeric molecular complexes for presentation of one or more antigens (e.g., tumor antigen(s)) and optionally one or more co-stimulatory signals. Antigen presenting platforms, as described in more detail below, can be based on artificial solid supports, such as pharmaceutically acceptable supports including polymeric beads or particles.

In some embodiments, the T-cell co-stimulatory signal is an anti-CD28 antibody or portion thereof. In some embodiments, the anti-CD28 antibody comprises sequences of at least one human immunoglobulin isotype selected from IgG1, IgG2, IgG3, IgG4, IgD, IgA, or IgM. For example, the anti-CD28 antibody may be an IgG isotype, and may contain sequences of one or more IgG germline framework sequences. For example, the anti-CD28 may contain a human IGHV4 heavy chain amino acid sequence, which may be modified with from one to fifteen amino acid modifications. The modifications may comprise murine framework residues to support the integrity of the antigen binding site(s).

The complementarity determining region (CDR) in some embodiments is based on a murine antibody amino acid sequence, which may optionally have from one to ten, such as from one to five, amino acid modifications. In some embodiments, one, two, three, or more CDRs are based on mouse 9.3 mAb (Tan et al. J. Exp. Med. 1993 177:165), which is publicly available. Exemplary CDRs are shown in FIGS. 1-6. In some embodiments, the antibody has the full set of heavy chain and/or full set of light chain CDRs of 9.3 mAb. For example, in some embodiments the heavy chain variable region contains one, two or three of the following CDRs, which optionally may each be modified by one, two, or three amino acid substitutions, deletions, or additions: CDR1 (DYGVH), CDR2 (VIWAGGGTNYNSALMS), and CDR3 (DKGYSYYYSMDY). In some embodiments, the light chain variable region contains one, two, or three of the following CDRs, which each may be modified by one, two, or three amino acid substitutions, deletions, or additions: CDR1 (RASESVEYYVTSLMQ), CDR2 (AASNVES), and CDR3 (QQSRKVPYT).

In some embodiments, the anti-CD28 ligand binds to the same or overlapping epitope as 9.3 mAb, or binds the same or overlapping epitope as an antibody having CDR1, CDR2, and CDR3 of 9.3 mAb. Antibodies with the same or overlapping epitope can be selected by any suitable technique, including competitive immunoassays, using, for example, Surface Plasmon Resonance (Biacore).

Alternative CDR sequences, variable regions, or CD28-binding ligands may be employed in various embodiments. Alternative ligands, CD28 epitopes, and anti-CD28 antibodies are described in U.S. Pat. Nos. 7,612,170, 6,987,171, and 6,887,466, for example, and these disclosures are hereby incorporated by reference in their entireties.

In some embodiments, the antibody heavy chain comprises a variant of a human IGHV4-59 germline framework (FW), which is modified to include from 5 to 15 murine FW residues. In some embodiments, the antibody comprises light chain amino acid sequences, and the light chain sequences may be a variant of human IGKV4-01 FW sequences, and which may be modified to include from 3 to 15 murine FW residues.

The anti-CD28 human heavy chain sequence may be modified, for example, to comprise one or more (e.g., 2 or more, 3 or more, 4 or more, 5 or more, or all) murine Fw residues at positions 1, 3, 6, 37, 48, 67, 71, 73, 76, 78, 82, 82a, and 82c (based on Kabat numbering). The murine Fw residues at these positions can be as in 9.3 mAb. The light chain may be modified to comprise one or more (e.g., 2 or more, 3 or more, 4 or more, 5 or more, or all) murine Fw residues at positions 3, 4, 49, 70, 85, 87, and 80. Selected murine Fw residues may support the integrity of the antigen-binding sites. The humanized anti-CD28 antibody maintains the affinity for CD28 and T cell co-stimulatory activity of 9.3 mAb, and is at least 40%, 50%, 75%, 80%, 90%, and in some embodiments 100% or more effective for CD28 binding and T cell activation than 9.3 mAb. In various embodiments, the anti-CD28 ligand is not a super agonist. In some embodiments, the anti-CD28 ligand binds to the same or overlapping epitope with 9.3 mAb.

The antibody may comprise a constant region and the constant region may be any isotype. In some embodiments, the antibody constant region is human IgG4 or variant thereof. In some embodiments, the constant region comprises one or more hinge stabilizing mutations, which may be introduced in the CH chain (e.g., S241, which may be substituted with P). In some embodiments, the antibody comprises a constant region and the constant region comprises one or more mutations suitable for chemically coupling the antibody to a solid support. The one or more mutations suitable for coupling may create an amino acid side chain functional group (e.g., thiol, amine, or hydroxyl), such as an unpaired cysteine (e.g., at S473). Other changes to the constant region include those modifications to reduce Fc gamma receptor binding. For example, the CH chain may be modified at L248, e.g., L248E.

In some embodiments, the co-stimulatory ligand is minimized such that the ligand is more suitable for functional attachment to nanoparticle surfaces. For example, the antibody may be an antibody fragment, such as F(ab')$_2$ or Fab, or is a single chain antibody, or other antigen-binding antibody fragment. For example, the antibody fragment can be a single chain variable fragment of the humanized mAb described herein or other anti-CD28.

In some embodiments, the co-stimulatory molecule is a single chain variable fragment (scFv) comprising or consisting essentially of the antigen binding loops formed by the VH and VL chains of an antiCD28 mAb, such as an antibody described herein. scFv antibody constructs may comprise one or several (2, 3, 4, or 5) VH and VL hypervariable region chains (the portion of each chain that together form the 3-D antigenic epitope binding pockets) linked together in head-head or head-tail configurations by short peptide linkers. Such constructs can be conveniently produced via a completely synthetic route due to their smaller size. Further, scFv can exhibit lower potential for immunogenicity.

In other embodiments, the co-stimulatory ligand is a bi-specific construct comprising one or more HLA molecules joined to a scFv of a co-stimulatory molecule ligand or inhibitory ligand. The antigen presenting complex and co-stimulatory or inhibitory ligand may be conjugated through a peptide tether that allows the bi-specific construct to be covalently linked to a nanoparticle surface. In some embodiments, such constructs produce the same activity as nanoparticles containing larger constructs of HLA and co-stimulatory or inhibitory ligands each linked to the NP surface independently, thereby providing manufacturing advantages.

In some embodiments, other ligand-binding formats are used to produce the co-stimulatory ligand, including peptides, aptamers, and AdNectins. The various formats for target binding include a single-domain antibody, a recombinant heavy-chain-only antibody (VHH), a single-chain antibody (scFv), a shark heavy-chain-only antibody (VNAR), a microprotein (cysteine knot protein, knottin), a DARPin, a Tetranectin, an Affibody; a Transbody, an Anticalin, an Affilin, a Microbody, a peptide aptamer, a phylomer, a stradobody, a maxibody, an evibody, a fynomer, an armadillo repeat protein, a Kunitz domain, an avimer, an atrimer, a probody, an immunobody, a triomab, a troybody, a pepbody, a UniBody, a DuoBody, a Fv, a Fab, a Fab', a F(ab')2, a peptide mimetic molecule, or a synthetic molecule, or as described in US Patent Nos. or Patent Publication Nos. U.S. Pat. No. 7,417,130, US 2004/132094, U.S. Pat. No. 5,831,012, US 2004/023334, U.S. Pat. Nos. 7,250,297, 6,818,418, US 2004/209243, U.S. Pat. Nos. 7,838,629, 7,186,524, 6,004,746, 5,475,096, US 2004/146938, US 2004/157209, U.S. Pat. Nos. 6,994,982, 6,794,144, US 2010/239633, U.S. Pat. No. 7,803,907, US 2010/119446, and/or U.S. Pat. No. 7,166,697, the contents of which are hereby incorporated by reference in their entireties. See also, Storz MAbs. 2011 May-June; 3(3): 310-317.

The co-stimulatory molecule may be conjugated to a solid support with antigen-presenting molecular complexes, to induce antigen-specific T cells. The antigen-presenting molecular complex may include MHC Class I and/or Class II complexes, or portions thereof comprising an antigen-binding cleft. In some embodiments, the molecular complex comprises one or two HLA amino acid sequences, which may contain additional heterologous sequences, such as immunoglobulin sequences. Alternative heterologous sequences include dimerizing amino acid sequences such as c-fos and c-jun. HLA-fusions in some embodiments provide additional advantages in stability, binding affinity, and/or T cell activation.

In various embodiments, the antigen presenting complex is either an MHC class I molecular complex or an MHC class II molecular complex, or alternatively CD1d. The MHC class I molecular complex may comprise at least two fusion proteins. A first fusion protein comprises a first MHC class I α chain and a first immunoglobulin heavy chain and a second fusion protein comprises a second MHC class I α chain and a second immunoglobulin heavy chain. The first and second immunoglobulin heavy chains associate to form the MHC class I molecular complex. The MHC class I molecular complex comprises a first MHC class I peptide binding cleft and a second MHC class I peptide binding cleft. The MHC class II molecular complex can comprise at least four fusion proteins. Two first fusion proteins comprise (i) an immunoglobulin heavy chain and (ii) an extracellular domain of an MHC class IIβ chain. Two second fusion proteins comprise (i) an immunoglobulin light chain and (ii) an extracellular domain of an MHC class IIα chain. The two first and the two second fusion proteins associate to form the MHC class II molecular complex. The extracellular domain of the MHC class IIβ chain of each first fusion protein and the extracellular domain of the MHC class IIα chain of each second fusion protein form an MHC class II peptide binding cleft. Antigenic peptides are bound to the peptide binding clefts. In various embodiments, the immunoglobulin sequence is a partial heavy chain sequence comprising the hinge region to support dimerization.

In some embodiments, the antigen presenting complex is a synthetic or recombinant HLA monomer (e.g., class I alpha chain with β2 microglobulin) engineered to contain an unpaired cysteine, or using a naturally occurring unpaired cysteine, for conjugation to nanoparticles. Further, the co-stimulatory signal (or other antibody-based ligand) may be a Fab or scFv. In such embodiments, the two signals may be combined in a single multi-functional construct comprising an HLA molecule tethered to an antigen binding antibody fragment (e.g., scFv) that binds to a desired receptor.

In other aspects and embodiments, the invention provides a bead- or particle-conjugated molecular complex for presentation of antigen to T cells, where the complex comprises a humanized immunoglobulin sequence or portion thereof fused to an antigen presenting sequence, e.g., an HLA amino acid sequence. In some embodiments, the immunoglobulin sequence is a human heavy chain sequence (e.g., IGHV4 framework). The variable region does not comprise an antigen binding activity to CD28, or other human protein. The HLA amino acid sequence may be HLA-A*02:01 (IMGT Accession No. HLA00005) or a derivative or fragment thereof, such as a derivative having from 1 to 10, or from 1 to 5, amino acid substitutions, deletions, or insertions. The humanized immunoglobulin sequence may further comprise a linker amino acid sequence between the HLA and immunoglobulin sequences. Preferably, the linker lacks immunogenicity. The molecular complex may further comprise β2 microglobulin peptide.

In various embodiments, the immunoglobulin fusion sequences is of IgG, IgD, IgA, or IgM isotype, and may be derived from any human germline framework. The germline framework includes IGHV4 (e.g., IGHV4-59), which may or may not contain one or more of the murine framework residues described with respect to anti-CD28. In some embodiments, the heavy chain of the anti-CD28 antibody described above (with or without murine framework residues) is fused to HLA in accordance with this aspect, and in such embodiments, the variable region is modified to reduce or eliminate CD28 binding.

In some embodiments, the HLA fusion construct contains no variable chain sequences. For example, the HLA or antigen presenting complex can be fused to an Ig constant region sequence above the hinge region to provide a dimeric HLA. For example, an HLA or antigen presenting portion thereof may be conjugated to a CH1 portion of each IgG heavy chain. All IgG molecules consist of two identical heavy chains (constant and variable regions) joined together by disulfide bonds in the hinge region (upper and lower). For example, in some embodiments, an HLA molecule or antigen presenting complex is fused to the CH1 (N-terminal end of the IgH chain above the hinge region), thereby creating a dimeric fusion protein that is smaller due to lack of any VH and VL light chain sequences. Thus, such constructs would include CH2 and CH3 domains. Such a construct may provide manufacturing advantages, as well as exhibit less potential for immunogenicity. In some embodiments, such constructs also display sufficient binding cooperativity for efficient T cell activation, despite the smaller distance from the hinge region.

The particle chemistry allows for the ligand density to be fine tuned. Generally, nano aAPCs have from 5 to about 1500 ligands conjugated to their surface on average. In some embodiments, the particles have less than about 500 ligands per particle, or less than about 400 ligands per particle, or less than about 300 ligands per particle, or less than about 200 ligands per particle. In some embodiments, the polymeric nanoparticles have less than about 150 ligands per particle, or less than about 100 ligands per particle. For example, the particles may have from about 5 to about 90 ligands per particle. In various embodiments, the nanoparticles comprise less than about 90 conjugated ligands per particle, or less than about 80, or less than about 70, or less than about 60, or less than about 50, or less than about 40, or less than about 30, or less than about 20 conjugated ligands per particle. In some embodiments, the particle contains from 10 to about 80 conjugated ligands on its surface, or from 10 to about 70, or about 10 to about 50 conjugated ligands per particle.

In still other embodiments, the antigen presenting complexes (e.g., HLA sequences) do not contain Ig fusion partners, and are monomeric. For example, in some embodiments, the C-terminal end of the antigen presenting complex or HLA molecule (e.g. HLA-A2, etc.) contains a peptide tether sequence suitable for site-directed binding to a functional group (e.g. a maleimide moiety) on a solid/semi-solid substrate such as a synthetic nanoparticle (e.g. containing PLGA-PEG-maleimide or PLA-PEG-maleimide block polymers). The tether sequence may contain any suitable sequence, which may be predominately composed of hydrophilic residues such as Gly, Ser, Ala, and Thr, such as two, three, four, or five repeats of GGGSG or AAAGG, with cysteine residue incorporated somewhere within the about 5 to about 15 (or about 5 to about 10 amino acid) tether. The cysteine residue should be incorporated at a site predicted not to form intramolecular disulfide bonds.

In some embodiments, the HLA-Ig fusion or other HLA construct further comprises an antigenic peptide bound to the HLA for presentation to T cells. The antigenic peptide can comprise an antigenic portion of one or more of tyrosinase, hTERT, MAGE-1, MAGE-3, gp-100, NY-ESO-1, Melan A/Mart-1, HPV 16-E7, gp75/brown, BAGE, and S-100 and/or any of the antigenic peptides as described in WO 2004/006951 for presentation by Class I or Class II complexes, the contents of which are hereby incorporated by reference in their entirety.

Other signals that can be provided with the antigen presenting complex include: CD80 (B7-1), CD86 (B7-2), B7-H3, 4-1BBL, CD27, CD30, CD134 (OX-40L), B7h (B7RP-1), CD40, LIGHT, (or Ig fusions, optionally humanized as described herein, of the such molecules or active portions thereof), antibodies that specifically bind to HVEM, antibodies that specifically bind to CD40L, antibodies that specifically bind to OX40, antibodies that specifically bind Fas, antibodies that specifically bind PD1, antibodies that specifically bind to GITR, and antibodies that specifically bind to 4-1BB. Where the co-stimulatory signal is an antibody against a natural ligand, the techniques used herein to humanize and/or minimize the size of the antibody ligand (e.g., scFv and bi-specific constructs), and engineer the antibody for conjugation to particles, may be employed.

Adhesion molecules useful for antigen presenting platforms of the invention may mediate the adhesion of the platform to a T cell or to a T cell precursor. Adhesion molecules useful in the present invention include, for example, ICAM-1 and LFA-3.

T cell growth factors affect proliferation and/or differentiation of T cells. Examples of T cell growth factors include cytokines (e.g., interleukins, interferons) and superantigens. Particularly useful cytokines include IL-2, IL-4, IL-7, IL-10, IL-12, IL-15, and gamma interferon. T cell growth factors may be encapsulated in the beads or particles or chemically conjugated or adsorbed to the surface. Thus, in some embodiments, the nanoparticles further comprise a therapeutic compound or protein/peptide entrapped in the hydrophobic core of the particle (e.g. a chemotherapy agent, cytokine or interleukin such as IL-2, a chemokine like CCL9 that attracts T cells, and/or a checkpoint inhibitor molecule like anti-PD1 antibody or anti-PD1 peptide). Such an aAPC in some embodiments is constructed to target specific cells for stimulation or inhibition as well as reprogramming. In some embodiments, entrapped compounds are released by degradation of the particle matrix. Such an aAPC could make combination therapies more tolerable and efficacious by limiting unwanted activity due to off-target interactions. In some embodiments, the nanoparticle aAPCs do not encapsulate drug compounds, such as cytokines and small molecule drugs.

Antigens presented in accordance with aspects of the invention include tumor associated antigens. Tumor-associated antigens include unique tumor antigens expressed exclusively by the tumor from which they are derived, shared tumor antigens expressed in many tumors but not in normal adult tissues (oncofetal antigens, cancer/testis antigens), and tissue-specific antigens expressed also by the normal tissue from which the tumor arose. Tumor-associated antigens can be, for example, embryonic antigens, antigens with abnormal post-translational modifications, differentiation antigens, products of mutated oncogenes or tumor suppressors, fusion proteins, or oncoviral proteins. A variety of tumor-associated antigens are known in the art, and many of these are publically available. Oncofetal and embryonic antigens include carcinoembryonic antigen and alpha-fetoprotein (usually only highly expressed in developing embryos but frequently highly expressed by tumors of the liver and colon, respectively), placental alkaline phosphatase sialyl-Lewis X (expressed in adenocarcinoma), CA-125 and CA-19 (expressed in gastrointestinal, hepatic, and gynecological tumors), TAG-72 (expressed in colorectal tumors), epithelial glycoprotein 2 (expressed in many carcinomas), pancreatic oncofetal antigen, 5T4 (expressed in gastric carcinoma), alpha fetoprotein receptor (expressed in multiple tumor types, particularly mammary tumors), and M2A (expressed in germ cell neoplasia).

In some embodiments, at least one antigen is a Cancer/Testis (CT) antigen, which may include NY-ESO-1, MAGE-A, B, and C, CTAG-1, CTAG-45, GAGE, and SSX, which are normally expressed by germ cells of the testis and not in normal adult somatic tissues. However, numerous types of cancer cells have been shown to express CT antigens including melanoma, breast, liver, lung, ovary, and Hodgkin Lymphoma.

Tumor-associated differentiation antigens include tyrosinase (expressed in melanoma) and particular surface immunoglobulins (expressed in lymphomas).

Mutated oncogene or tumor-suppressor gene products include Ras and p53, both of which are expressed in many tumor types, Her-2/neu (expressed in breast—and gynecological cancers), EGF-R, estrogen receptor, progesterone receptor, retinoblastoma gene product, myc (associated with lung cancer), ras, p53 nonmutant associated with breast tumors, MAGE-1, and MAGE-3 (associated with melanoma, lung, and other cancers).

Other tumor antigens include fusion proteins such as BCR-ABL, which is expressed in chromic myeloid leukemia, and oncoviral proteins such as HPV type 16, E6, and E7, which are found in cervical carcinoma. Tissue-specific tumor antigens include melanotransferrin and MUC1 (expressed in pancreatic and breast cancers); CD 10 (previously known as common acute lymphoblastic leukemia antigen, or CALLA) or surface immunoglobulin (expressed in B cell leukemias and lymphomas); the α chain of the IL-2 receptor, T cell receptor, CD45R, CD4+/CD8+ (expressed in T cell leukemias and lymphomas); prostate-specific antigen and prostatic acid-phosphatase (expressed in prostate carcinoma); gp100, MelanA/Mart-1, tyrosinase, gp75/brown, BAGE, and S-100 (expressed in melanoma); cytokeratins (expressed in various carcinomas); and CD19, CD20, and CD37 (expressed in lymphoma).

In some embodiments, the antigenic peptides include MART-1, gp100, NY-ESO-1, and MAGE-A3 which are presented by the HLA antigen presenting complexes described herein, such as the HLA-Ig fusion complex described herein.

In some embodiments, the aAPC presents one or more antigenic peptides based on tumor-driving mutations, or neoantigens determined from personalized evaluation of a patient tumor.

In still other embodiments, the composition comprises a cocktail of aAPCs that contain a plurality of antigens for the tumor type, such as at least 2, 3, 4, 5, 6, 7, 8, 9, or 10 antigens (e.g., from 2 to 10 or from 3-8 antigens). Generally, each aAPC presents a single antigen.

In some embodiments, the antigen is an autoantigen, which is an organism's own "self antigen" to which the organism produces an immune response. Autoantigens are involved in autoimmune diseases such as Goodpasture's syndrome, multiple sclerosis, Graves' disease, myasthenia gravis, systemic lupus erythematosus, insulin-dependent diabetes mellitis, rheumatoid arthritis, pemphigus vulgaris, Addison's disease, dermatitis herpetiformis, celiac disease, and Hashimoto's thyroiditis. For example, diabetes-related autoantigens include insulin, glutamic acid decarboxylase (GAD) and other islet cell autoantigens, e.g., ICA 512/IA-2 protein tyrosine phosphatase, ICA12, ICA69, preproinsulin or an immunologically active fragment thereof (e.g., insulin B-chain, A chain, C peptide or an immunologically active fragment thereof), IGRP, HSP60, carboxypeptidase H, peripherin, gangliosides (e.g., GM1-2, GM3) or immunologically active fragments thereof.

In some embodiments, the antigen(s) are of infectious agents, such as components of protozoa, bacteria, fungi (both unicellular and multicellular), viruses, prions, intracellular parasites, helminths, and other infectious agents that can induce an immune response.

Antigens, including antigenic peptides, can be bound to an antigen binding cleft of an antigen presenting complex either actively or passively, as described in U.S. Pat. No. 6,268,411 which is hereby incorporated by reference in its entirety. Optionally, an antigenic peptide can be covalently bound to a peptide binding cleft.

If desired, a peptide tether can be used to link an antigenic peptide to a peptide binding cleft. For example, crystallographic analyses of multiple class I MHC molecules indicate that the amino terminus of β2M is very close, approximately 20.5 Angstroms away, from the carboxyl terminus of an antigenic peptide resident in the MHC peptide binding cleft. Thus, using a relatively short linker sequence, approximately 13 amino acids in length, one can tether a peptide to the amino terminus of β2M. If the sequence is appropriate, that peptide will bind to the MHC binding groove (see U.S. Pat. No. 6,268,411, which is hereby incorporated by reference).

In some embodiments, the aAPCs have physical properties that allow them to expand and activate antigen-specific T cells (including naive cells), for example, to produce cytotoxic T cells and ideally long lived memory T cells. The nano-aAPC according to this disclosure are engineered based on aspects of particle size, ligand affinity, duration of ligand binding, densities and/or clusters of binding ligands, size and orientation of ligands, and particle surface properties, among other things. Artificial antigen presenting cells (aAPCs) have conventionally been considered in the context of the immune synapse, in which TCR and co-signal clustering is considered to play an important role in activation, particularly for naive T cells. Thus, while aAPCs have been created in an attempt to mimic these interactions by using cell-sized particles and/or matrices designed to provide "rafts" or ligand clusters, the present nanoscale aAPCs mimic the biological system through nano-size particles, having in various embodiments engineered particle size and chemistry, T cell ligands, ligand orientation, ligand densities, and ligand ratios.

In some embodiments, the antigen-presenting complex and co-stimulatory signal are conjugated to PLGA/PLGA-PEG particles or PLA/PLA-PEG particles having surface functional groups on the terminal end of the PEG co-polymer (e.g., the end that faces outward towards the surface of the particle), such as PLGA-PEG-maleimide or PLA-PEG-maleimide particles, which provide functional groups for chemical coupling on the hydrophilic exterior surface. In some embodiments, the aAPCs persist in peripheral blood circulation sufficiently long to allow distribution to target tissues, including trafficking to lymph nodes via blood/lymph exchange. The composition of the shell may also impact biodistribution. Thus, in various embodiments the particles have a hydrophilic shell, which can be formed by the PEG portion of the co-polymer. In various embodiments, the charge of the particles is slightly negative, for example, due to the combination of the COOH groups on the PLGA or PLA as well as by charge contributed by the targeting ligands attached to the surface of the particle. In some embodiments, the particles (either with or without conjugated ligand) have a surface charge of from about 0 to about −20 mV, or in some embodiments −5 to −15 mV, or from about −5 to about −10 mV. In some embodiments, the size and surface characteristics of the nanoparticles are such that they are able to be internalized by T cells.

Nanoparticles comprising PLGA-PEG copolymers are described in U.S. Pat. No. 8,420,123, for example, which is hereby incorporated by reference.

The particles can vary from being irregular in shape to being spherical and/or from having an uneven or irregular surface to having a smooth surface. Spherical particles have less surface area relative to particles of irregular size. If spherical particles are used, less reagent is necessary due to the reduced surface area. On the other hand, an irregularly shaped particle has a significantly greater surface area than a spherical particle, which provides an advantage for conjugated protein content per surface area and surface area contact for cells. For example, asymmetrical nanoparticles may have at least one surface having a radius of curvature along at least one axis which is in one of the following ranges: (a) about 1 nm to about 10 nm; (b) about 11 nm to about 100 nm; (c) about 101 nm to about 400 nm; (d) about 401 nm to about 1 μm; (e) about 10 μm to about 20 μm; (f) about 20 μm to about 100 μm; and (g) about 101 μm to about 1 mm. In some embodiments, the asymmetric nanoparticle may has an asymmetrical shape defined by a dimension (a) along an x-axis, a dimension (b) along a y-axis, and a dimension (c) along a z-axis, wherein at least one of (a), (b), or (c) is not equal to at least one other dimension (a), (b), or (c). In some embodiments, the asymmetrical shape is an ellipsoid, which can be described by one of the following equations: a>b=c (prolate ellipsoid); a>b>c (tri-axial ellipsoid); and a=b>c (oblate ellipsoid). Asymmetrical nanoparticles that may be used in accordance with the invention are described in WO 2013/086500, which is hereby incorporated by reference in its entirety.

The particle size in various embodiments is in the range of 20 to 500 nm, or 50 to 500 nm in diameter (average diameter). In some embodiments, the particles have an average size of less than about 400 nm, or less than about 300 nm, or less than about 200 nm, to allow for better peripheral blood circulation and penetration of tissues, including tumor tissue. In some embodiments, the nanoparticles have an average size (e.g., diameter or largest axis) of from about 50 nm to about 200 nm, or from about 100 nm to about 200 nm, such as from about 120 nm to about 180 nm or about 50 to about 100 nm. The term "about", when connected to a numerical feature, means±10%. In some embodiments, at least 90% of the particles are in the range of about 120 nm to about 180 nm or in the range of about 40 nm to about 110 nm. The particles can be uniform in size or can vary in size, with the average particle size preferably being as described above. In some embodiments, the particles are sufficiently small to take advantage of the "EPR effect" (enhanced permeability and retention effect).

Ligands and molecular complexes described herein can be chemically conjugated to the beads using any available process. Functional groups for ligand binding include PEG-COOH, PEG-NH2, PEG-SH, PEG-maleimide, PEG-pyridyl disulfide and PEG acrylate. See, e.g., Hermanson, BIOCONJUGATE TECHNIQUES, Academic Press, New York, 1996. Activating functional groups include alkyl and acyl halides, amines, sulfhydryls, aldehydes, unsaturated bonds, hydrazides, isocyanates, isothiocyanates, ketones, azide, alkyne-derivatives, anhydrides, epoxides, carbonates, aminoxy, furan-derivatives and other groups known to activate for chemical bonding. Alternatively, a molecule can be bound to a solid support through the use of a small molecule-coupling reagent. Non-limiting examples of coupling reagents include carbodiimides, maleimides, N-hydroxysuccinimide esters, bischloroethylamines, bifunctional aldehydes such as glutaraldehyde, anhydrides and the like. In other embodiments, a molecule can be coupled to a solid support through affinity binding such as a biotin-streptavidin linkage or coupling, as is well known in the art. For example, streptavidin can be bound to a solid support by covalent or non-covalent attachment, and a biotinylated molecule can be synthesized using methods that are well known in the art.

Activation chemistries allow for specific, stable attachment of molecules to the surface of solid supports. There are numerous methods that can be used to attach proteins to functional groups. For example, the common cross-linker glutaraldehyde can be used to attach protein amine groups to an aminated solid support surface in a two-step process. The resultant linkage is hydrolytically stable. Other methods include use of cross-linkers containing n-hydro-succinimido (NHS) esters which react with amines on proteins, cross-linkers containing active halogens that react with amine-, sulfhydryl-, or histidine-containing proteins, cross-linkers containing epoxides that react with amines or sulfhydryl groups, conjugation between maleimide groups and sulfhydryl groups, and the formation of protein aldehyde groups by periodate oxidation of pendant sugar moieties followed by reductive amination.

In some embodiments, the particle or bead is a polymer comprising PLGA as a core polymer, PLGA-PEG-maleimide, and an ester-endcapped PLGA-PEG. Alternatively, the particle or bead comprises PLA as a core polymer, PLA-PEG-maleimide, and an ester-endcapped PLA-PEG. The maleimide group provides the formed particles with a hydrophilic "stealth" coating (PEG) on the outer surface of the particle as well as functional groups attached to this shell that can be used for covalent attachment of ligands that have at least one free sulfhydryl (—SH) group available. For example, HLA-Ig ligands and/or anti-CD28 (or other antibody ligand) can be constructed on a human IgG4 framework (as described herein) that contains a S473C substitution in the Fc. This unpaired cysteine residue at 473 of either HLA-Ig or anti-CD28 can be conjugated to the maleimide group attached to the PEG under mild reducing conditions. Mild reducing conditions are unlikely to irreversibly denature the proteins, especially the HLA-beta-2-microglobulin portion of the HLA-Ig molecule.

In an exemplary embodiment, the nanoparticles have a core (PLGA) that can be tuned for a specific biodegradation rate in vivo (by adjusting the LA:GA ratio and/or molecular weight of the PLGA polymer), a hydrophilic outer shell that protects from opsonization by serum proteins and removal from circulation (acting like "PEG brushes"), surface functionalized with consistent control of ligand density (stochastic relationship of 1 molecule/maleimide group) and orientation of ligand away from the core. In exemplary embodiments, the PLGA is based on a LA:GA ratio of from 20:1 to 1:20, including compositions of L/G of: 5/95, 10/90, 15/85, 20/80, 25/75, 30/70, 35/65, 40/60, 45/55, 50/50, 55/45, 60/40, 65/35, 70/30, 75/25, 80/20, 85/15, 90/10, or 95/5. PLGA degrades by hydrolysis of its ester linkages. The time required for degradation of PLGA is related to the ratio of monomers:the higher the content of glycolide units, the lower the time required for degradation as compared to predominantly lactide units. In addition, polymers that are endcapped with esters (as opposed to the free carboxylic acid) have longer degradation half-lives.

In some embodiments, the PLGA is based on a LA:GA ratio of from 4:1 to 1:4, and in some embodiments is about 1:1. In some embodiments, the PLGA core has a molecular weight of about 20K to about 50K, or from about 30K to about 40K (e.g., about 35K). The PLGA-PEG polymers (including PLGA-PEG-maleimide and PLGA-PEG-MeOH polymers) have PLGA portion in the range of 10K to 30K in molecular weight (e.g., about 20K), and a PEG portion with a molecular weight of about 2K to about 10K, such as about 3K and/or about 5K. In various embodiments, the mass ratio of PLGA-PEG-maleimide and PLGA-PEG-MeOH polymers is from about 15:1 to about 1:15, such as about 10:1 to about 1:10, or about 5:1 to about 1:5. In some embodiments, the ratio of PLGA-PEG-maleimide and PLGA-PEG-MeOH polymers is 4:1 to about 1:4, such as about 4:1, about 3:1, about 2:1, about 1:1, about 1:2, about 1:3, and about 1:4. In still further embodiments, the mass ratio of PLGA-PEG-maleimide and PLGA-PEG-MeOH is in the range of 1:5 to about 1:15, such as about 1:10. This ratio is selected in some embodiments to fine tune the ligand density for optimal T cell activation.

In some embodiments, the particle is based on PLA polymers. In some embodiments, the PLA core polymers have a molecular weight of about 20K to about 50K, or about 30K to about 40K (e.g., about 35K). The PLA-PEG polymers (including PLA-PEG-maleimide and PLA-PEG-MeOH polymers) have PLA portion in the range of 10K to 30K in molecular weight (e.g., about 20K), and a PEG portion with a molecular weight of about 2K to about 10K, such as about 3K and/or about 5K. In various embodiments, the mass ratio of PLA-PEG-maleimide and PLA-PEG-MeOH polymers is from about 15:1 to about 1:15, such as about 10:1 to about 1:10, or about 5:1 to about 1:5. In some embodiments, the ratio of PLA-PEG-maleimide and PLA-PEG-MeOH polymers is 4:1 to about 1:4, such as about 4:1, about 3:1, about 2:1, about 1:1, about 1:2, about 1:3, and about 1:4. In still further embodiments, the mass ratio of PLA-PEG-maleimide and PLA-PEG-MeOH is in the range of 1:5 to about 1:15, such as about 1:10. This ratio is selected in some embodiments to fine tune the ligand density for optimal T cell activation.

The ratio of particular proteins on the particle can be varied. For example, ratios of antigen presenting complex to anti-CD28 can be at least about 30:1, or at least about 10:1, about 3:1, about 1:1, about 1:3; about 1:10, or at least about 1:30. In some embodiments, the ratio is about 5:1, about 4:1, about 3:1, about 2:1, about 1:1, about 1:2, about 1:3, about 1:4, or about 1:5. The total amount of protein coupled to the particles can be from 1 to about 100 µg, or from about 1 to about 50 µg, or from 1 to about 10 µg per mg of particle, or in some embodiments, from 2 to 6 µg per mg of particle. In some embodiments, the ligand density of the particles is from about $10^3$ to about $10^5$ ligands/µm$^2$, or about $10^4$ ligands/µm$^2$. For example, for nanoparticles in the range of 20 to 200 nm in size, the nanoparticles on average have about 5 to about 1500 ligands per particle, such as about 10 to about 1500 ligands per particle, or about 10 to about 1200 ligands per particle, or about 10 to about 1000 ligands per particle, or about 10 to about 800 ligands per particle. In some embodiments, the particles contain less than about 500 ligands per particle, or less than about 400 ligands per particle, or less than about 300 ligands per particle, or less than about 100 ligands per particle, or less than about 90 ligands per particle, or less than about 80 ligands per particle, or less than about 70 ligands per particle, or less than about 60 ligands per particle, or less than about 50 ligands per particle, or less than about 40 ligands per particle, or less than about 30 ligands per particle, or less than about 20 ligands per particle, or less than about 10 ligands per particle, down to about 5 ligands per particle in some embodiments.

In some embodiments, the invention employs minimal constructs for signal 1 and signal 2 (such as, for signal 1, monomeric class I alpha chain with linked β2 microglobulin, which are optionally dimeric by fusion to an Ig sequence just above the hinge region, and for signal 2, a scFv as described) thereby providing the potential for self-assembling nanoparticles. For example, the PLGA-PEG or PLA-PEG polymers are prepared with conjugated ligands (e.g., PLGA-PEG-signal 1 and PLGA-PEG-signal 2) and then mixed at a specific polymer ratio with PLGA or PLA followed by nano-precipitation such that the final NP product is formed during the mixing/precipitation step (self-assembly). Such a process can substantially simplify the manufacturing procedure.

In various embodiments, the invention provides a pharmaceutical composition comprising a polymeric bead or particle, an anti-CD28 antibody as described herein, and/or an antigen-presenting complex, such as humanized Ig HLA fusion complex as described herein. The pharmaceutical composition may further comprise an antigenic peptide for presentation to T cells as described, and which may be co-formulated with the conjugated bead or particle. In various embodiments, the pharmaceutical composition is shelf stable, and in some embodiments, is provided in lyophilized form for reconstitution prior to administration, or provided in another "off-the-shelf" pharmaceutical preparation.

In some embodiments, the invention provides a pharmaceutical composition comprising PLGA/PLGA-PEG based nanoparticles, or PLA/PLA-PEG based nanoparticles, of from 50 to 200 nm (e.g., from 100 to 200 nm) in diameter or average diameter, and comprising surface-conjugated anti-CD28 antibodies and antigen-presenting complexes. The anti-CD28 antibody can be a humanized antibody, e.g., as described herein, and may be an antibody fragment such as a single chain variable fragment. The antigen presenting complex in some embodiments comprises at least one HLA antigen-binding cleft. The anti-CD28 and HLA complex can be coupled to the particles separately or together in the same reaction. The pharmaceutical composition can include at least one peptide antigen, such as a tumor antigen (e.g., MART-1 or other antigen described herein), and which may be co-formulated with the particles without any active loading process.

Alternative polymers that can be used in connection with the nano-aAPC platforms described herein include one or more of cyclodextrin-containing polymers, cationic cyclodextrin-containing polymers, poly(D,L-lactic acid-co-glycolic acid) (PLGA), poly(caprolactone) (PCL), ethylene vinyl acetate polymer (EVA), poly(lactic acid) (PLA), poly (L-lactic acid) (PLLA), poly(glycolic acid) (PGA), poly(L-lactic acid-co-glycolic acid) (PLLGA), poly(D,L-lactide) (PDLA), poly(L-Lactide) (PLLA), PLGA-b-poly(ethylene glycol)-PLGA (PLGA-bPEG-PLGA), PLLA-bPEG-PLLA, PLGA-PEG-maieimide (PLGA-PEG-mal), PLA-PEG-maleimide, poly(D,L-lactide-co-caprolactone), poly(D,L-Lactide-co-caprolactone-co-glycolide), poly(D,L-lactide-co-PEO-co-D,L-lactide), poly(D,L-lactide-co-PPO~co-D,L-lactide), polyalkylcyanoacralate, polyurethane, poly-L-lysine (PLL), hydroxypropyl methacrylate (HPMA), polyethyleneglycol, poly-L-glutamic acid, poly(hydroxy acids), polyanhydrides, polyorthoesters, poly(ester amides), polyamides, poly(ester ethers), polycarbonates, polyalkylenes such as polyethylene and polypropylene, polyalkylene glycols such as poly(ethylene glycol) (PEG), polyalkylene oxides (PEO), polyalkylene terephthalates such as poly (ethylene terephthalate), polyvinyl alcohols (PVA), polyvinyl ethers, polyvinyl esters such as poly(vinyl acetate), polyvinyl haiides such as poly(vinyl chloride) (PVC), polyvinylpyrrolidone, polysiloxanes, polystyrene (PS), polyurethanes, derivatized celluloses such as alkyl celluloses, hydroxy alkyl celluloses, cellulose ethers, cellulose esters, nitro celluloses, hydroxypropylcellulose, carboxymethylcellulose, polymers of acrylic acids, such as polymethylmethacrylate) (P MA), poly(ethyl(meth)acrylate), poly(butyl (meth)acrylate), poly (isobutyl (meth)acrylate), poly(hexyl (meth)acrylate), poly(isodecyl(meth)acrylate), poly(lauryl (meth)acrylate), poly(phenyl(meth)acrylate), poly(methyl acrylate), poly(isopropyl acrylate), polyiisobutyl acrylate), poly(octadecyl acrylate) (poly acrylic acids), and copolymers and mixtures thereof, polydioxanone and its copolymers, polyhydroxyalkanoates, polypropylene fumarate), polyoxymethylene, poloxamers, poly(ortho)esters, poly(butyric acid), poly(valeric acid), poly(lactide-co-caprolactone), trimethylene carbonate, polyvinylpyrrolidone, polyorthoesters, polyphosphazenes, and polyphosphoesters, dendrimers and derivatives thereof, and blends and/or block copolymers of two or more such polymers.

The pharmaceutical compositions described herein are useful for immunotherapy, for example, in methods for inducing the formation of antigen-specific cytotoxic T cells, by administering an effective amount of the composition to a patient in need. In some embodiments, the patient is a cancer patient.

The particle-based antigen presenting platforms described herein can be administered to patients by any appropriate routes, including intravenous administration, intra-arterial administration, subcutaneous administration, intradermal administration, intralymphatic administration, and intra-tumoral administration. Patients include both human and veterinary patients.

In some embodiments the invention provides a pharmaceutical composition that comprises polymeric PLGA/PLGA-PEG particles, or PLA/PLA-PEG particles having a size in the range of about 20 to 200 nm (e.g., 50 to 200 nm or 100 to 200 nm in some embodiments), a surface charge of about -0 to -20 mV (and -5 to -10 mV in some embodiments), and from about 10 to 1500 protein ligands per particle, or from 10 to about 150 ligands per particle (e.g., from about 10 to about 100 ligands per particle). Exemplary particles have a polydispersity index (PDI) of 0.3 or less. The protein ligands in some embodiments are each coupled to the particle through sulfhydryl-maleimide chemistry. The ligands comprise a population of anti-CD28 antibody ligands, and a population of HLA ligands and one or more antigenic peptides for presentation to T cells. The composition comprises a pharmaceutically acceptable carrier for intravenous, intra-arterial, subcutaneous, intradermal, intralymphatic, or intra-tumoral administration. In some embodiments, the composition is formulated for subcutaneous administration.

In particular, antigen presenting platforms can be useful for treating patients with infectious diseases, cancer, or autoimmune diseases, or to provide prophylactic protection to immunosuppressed patients.

Infectious diseases that can be treated include those caused by bacteria, viruses, prions, fungi, parasites, helminths, etc. Such diseases include AIDS, hepatitis, CMV infection, and post-transplant lymphoproliferative disorder (PTLD). CMV, for example, is the most common viral pathogen found in organ transplant patients and is a major cause of morbidity and mortality in patients undergoing bone marrow or peripheral blood stem cell transplants (Zaia, Hematol. Oncol. Clin. North Am. 4, 603-23, 1990). This is due to the immunocompromised status of these patients, which permits reactivation of latent virus in seropositive patients or opportunistic infection in seronegative individuals. Current treatment focuses on the use of antiviral compounds such as gancyclovir, which have drawbacks, the most significant being the development of drug-resistant CMV. A useful alternative to these treatments is a prophylactic immunotherapeutic regimen involving the generation of virus-specific CTL derived from the patient or from an appropriate donor before initiation of the transplant procedure.

PTLD occurs in a significant fraction of transplant patients and results from Epstein-Barr virus (EBV) infection. EBV infection is believed to be present in approximately 90% of the adult population in the United States (Anagnostopoulos & Hummel, Histopathology 29, 291-2) 15, 1996). Active viral replication and infection is kept in check by the immune system, but, as in cases of CMV, individuals immunocompromised by transplantation therapies lose the controlling T cell populations, which permits viral reactivation. This represents a serious impediment to transplant protocols. EBV may also be involved in tumor promotion in a variety of hematological and non-hematological cancers. There is also a strong association between EBV and nasopharyngeal carcinomas. Thus a prophylactic treatment with EBV-specific T cells offers an excellent alternative to current therapies.

Cancers that can be treated according to the invention include melanoma, carcinomas, e.g., colon, head and neck cancer, duodenal, prostate, breast, lung, ovarian, ductal, colon, hepatic, pancreatic, renal, endometrial, stomach, dysplastic oral mucosa, polyposis, invasive oral cancer, non-small cell lung carcinoma, transitional and squamous cell urinary carcinoma etc.; neurological malignancies, e.g., neuroblastoma, gliomas, etc.; hematological malignancies, e.g., chronic myelogenous leukemia, childhood acute leukemia, non-Hodgkin's lymphomas, chronic lymphocytic leukemia, malignant cutaneous T-cells, mycosis fungoides, non-MF cutaneous T-cell lymphoma, lymphomatoid papulosis, T-cell rich cutaneous lymphoid hyperplasia, bullous pemphigoid, discoid lupus erythematosus, lichen planus, etc.; and the like. See, e.g., Mackensen et al, Int. J. Cancer 86, 385-92, 2000; Jonuleit et al., Int. J. Cancer 93, 243-51, 2001; Lan et al., J. Immunotherapy 24, 66-78, 2001; Meidenbauer et al, J. Immunol. 170(4), 2161-69, 2003.

In some embodiments, the invention provides a method for treating cancer, including those cancers identified above, through administration of the pharmaceutical composition described herein to activate T-cells having anti-tumor activity. In some embodiments, the therapy is provided together with one or more immune checkpoint inhibitors, such as Nivolumab, Pembrolizumab, and Ipilimumab. In some embodiments, the additional therapy is anti-CTLA4 or anti-PD1, or anti-PD-L1. The additional therapy or checkpoint inhibitor may be administered separately through its conventional regimen, or may be administered as an additional ligand to the nanoparticles described herein, or attached to a separate population of nanoparticles. In some embodiments, the one or more immune checkpoint inhibitors are provided as initial therapy, and therapy with the aAPCs described herein initiated subsequently, for example, after from about 1 to about 8 weeks of checkpoint inhibitor therapy, or after about 2 to about 4 weeks of checkpoint inhibitor therapy. In some embodiments, the one or more checkpoint inhibitors are provided concomitantly with the nanoparticle therapy, for example at initiation of therapy and about every two weeks, or at initiation of therapy and about every two weeks for the one or more checkpoint inhibitors and about every four weeks for the nanoparticle therapy. In some embodiments, the patient is resistant or shows only a partial or transient response to checkpoint inhibitor therapy, and the aAPCs described herein enhance tumor regression in these patient. In still other embodiments, for cancers that are typically resistant to checkpoint inhibitor therapy, the compositions described herein expand the successful use of checkpoint inhibitors to such cancers.

In some embodiments, the peptide antigen is selected in a personalized basis for the patient, based on an analysis of the patient's tumor. For example, a process described by Ionov Y., *A high throughput method for identifying personalized tumor-associated antigens, Oncotarget* 1(2):148-155 (2010) (which is hereby incorporated by reference) may be used, or other process. In these embodiments, the nanoparticles can be provided (on an "off-the shelf" basis), and tumor antigens selected and loaded in a personalized basis.

In some embodiments, the nano-aAPCs are used as a booster vaccine, after adoptive T cell therapy, in which naive T cells from the patient or T cells from an HLA-matched donor are expanded ex vivo, and administered to the patient. The nano aAPC composition may be administered from 1 to about 10 times over the course of from 4 months to about 1 year to enhance cancer immunity in these embodiments.

Autoimmune diseases that can be treated include asthma, systemic lupus erythematosus, rheumatoid arthritis, type I diabetes, multiple sclerosis, Crohn's disease, ulcerative colitis, psoriasis, myasthenia gravis, Goodpasture's syndrome, Graves' disease, pemphigus vulgaris, Addison's disease, dermatitis herpetiformis, celiac disease, and Hashimoto's thyroiditis.

Antigen-specific helper T cells can be used to activate macrophages or to activate B cells to produce specific antibodies that can be used, for example, to treat infectious diseases and cancer. Antibody-producing B cells themselves also can be used for this purpose.

The invention further provides polynucleotides encoding the amino acid sequences described herein, as well as host cells expressing the same.

This invention is further illustrated by the following non-limiting examples.

EXAMPLES

Example 1: Design of Germline Humanized Variable Regions and Human Constant Region Sequences This Example demonstrates, inter alia, a design of sequences for germline humanized (CDR grafted) antibodies from a mouse anti-CD28 antibody template; a design of human constant region sequences including human IgG4 containing the S241P (Kabat numbering) hinge stabilizing mutation, the L248E (Kabat numbering) mutation to remove residual Fc gamma receptor binding and a Cys residue (S473C, Kabat numbering) suitable for coupling the antibody; a design of a variant germline humanized antibody V domain with potential non-binding to CD28; a design of a linker sequence for the fusion of HLA-A*02:01 to the N-terminus of the germline humanized antibodies that does not contain potential T cell epitopes.

The starting anti-CD28 antibody was the murine 9.3 monoclonal antibody (Tan et al. J. Exp. Med. 1993 177:165). Structural models of the 9.3 antibody V regions were produced using Swiss PDB and analyzed in order to identify amino acids in the V regions that were likely to be essential for the binding properties of the antibody. All residues contained within the CDRs (using both Kabat and Chothia definitions) together with a number of framework residues were considered to be of potential importance for binding. Both the VH and Vκ sequences of anti-CD28 contain typical framework (Fw) residues and the CDR 1, 2 and 3 motifs are comparable to many murine antibodies.

For humanization, the human IGHV4-59 germline Fw was selected as a template for the heavy chain (in preference to the IGHV3/OR16-10 selected by Tan et al. J. Immunol 2002 169:1119-1125). The IGKV4-01 germline Fw was selected as a template for the light chain. These Fws both have 62% homology to their respective murine VH and Vκ sequences.

The murine CDRs were grafted into these Fws and varying numbers of murine Fw residues were also included to create three humanized VH variants and three humanized Vκ variants (FIGS. 1-6).

For the heavy chain Fw, Fw1 residues 1 and 3 were thought to be important for antigen binding since they are adjacent to the binding pocket, while residue 6 was considered to affect the conformation of both the beta strand supporting residues 1 and 3 and the conformation of CDR3. Therefore these murine Fw residues were retained in all variants.

In Fw2, residue 37 was considered to be important for maintaining the interface between the VH and Vκ, while residue 48 was considered to support the conformation of CDR2; therefore both of these residues were retained in all variants.

In Fw3, residues 73, 76 and 78 directly contact CDR1, while residue 71 contacts both CDR1 and CDR2; therefore these residues are likely to be required for antigen binding (depending upon the contribution of CDR1 and CDR2) and were therefore retained in all variants. Residue 71 can sometimes indirectly affect the conformation of CDR1 by influencing the conformation of residues 71 to 78, while residues 82a and 82c may also indirectly influence the conformation of CDR2. These residues were therefore retained in VH1 only. Residues 67 and 82 are adjacent in the three dimensional structure and interact to fill space which can affect the conformation of CDR2 and potentially influence the beta strands supporting CDRs 1 and 3. Therefore these residues were retained in variants VH1 and VH2.

For the light chain Fw, Fw1 residue 3 is adjacent to the binding pocket and can be directly involved in antigen binding, while residue 4 directly supports the conformation of CDR3. Therefore these murine Fw residues were retained in all variants.

In Fw2, residue 49 supports the conformation of CDR2 and is also critical for the interface between the heavy and light chains where it directly supports the conformation of heavy chain CDR3, thus was retained in all variants.

In Fw3, residues 85 and 87 were considered important for the interface of the heavy and light chains and also to support the conformation of CDR3 and were therefore retained in all variants. Residue 80 was considered to potentially have indirect effects on the conformation of CDRs 2 and 3 and was retained in Vκ1 only. Residue 70 commonly salt bridges with light chain residue R24 and therefore has important conformational effects upon the Vκ domain. In anti-CD28, this salt bridge is absent (since residue 70 is N rather than D) and introducing this interaction could be disadvantageous; however in the murine antibody N70 is glycosylated (NFS) and it would be beneficial to remove this during humanization; therefore the murine N was retained in Vκ1 and Vκ2, but changed to D in Vκ3.

Constant region sequences based upon human IgG4/κ were designed to incorporate a hinge stabilizing mutation (S241P) and a mutation in the lower hinge that removes residual Fc gamma receptor binding (L248E). A cysteine residue was also included near the C-terminus of the Fc for chemical coupling purposes (S473C). The modified IgG4 heavy chain constant region sequence is shown in FIG. 7, together with the κ light chain constant region sequence (FIG. 8).

A further VH domain was designed for potential non-binding to CD28 and this sequence is shown in FIG. 9. Analysis of the murine V region sequences suggested (from the extent of somatic mutation of mouse germline V regions) that the VH was likely to the major contributor to CD28 binding. Therefore only a potential non-binding humanized VH variant was designed. This variant does not contain any mouse Fw residues to reconstitute the correct CDR conformations and also contains three mutations in CDRH3 at residues that are likely to be critical for binding (Y100A, Y100aA, Y100bA).

Example 2: Design of Linkers for Fusion of HLA-A*02:01 to Humanized Antibodies Linkers for the fusion of HLA-A*02:01 (IMGT Accession No. HLA00005) to the N-terminus of humanized anti-CD28 antibodies were constructed and incorporated analysis by iTope™ and TCED™ to remove potential immunogenicity.

The iTope™ software predicts favorable interactions between amino acid side chains of a peptide and specific binding pockets (in particular pocket positions; p1, p4, p6, p7 and p9) within the open-ended binding grooves of 34 human MHC class II alleles. These alleles represent the most common HLA-DR alleles found world-wide with no weighting attributed to those found most prevalently in any particular ethnic population. Twenty of the alleles contain the 'open' p1 configuration and fourteen contain the 'closed' configuration where glycine at position 83 is replaced by a valine. The location of key binding residues is achieved by the in silico generation of 9mer peptides that overlap by one amino acid spanning the test protein sequence. Comparisons with physical MHC class II binding experiments has shown that iTope™ can be used to successfully discriminate with high accuracy between peptides that either bind or do not bind MHC class II molecules. Any limitations of in silico MHC class II binding analysis are reduced using the TCED™ which contains the sequences of a large database of peptides (>10,000 peptides) derived from sequences previously screened in EpiScreen™ ex vivo T cell epitope mapping assays. The TCED™ can thus be used to search any test sequence against unrelated antibody and protein sequences to find correlations with actual ex vivo immunogenicity.

Analysis of the linker sequences using iTope™ was performed with overlapping 9 mers spanning the linker sequences which were tested against each of the 34 MHC class II alleles. Each 9mer was scored based on the potential 'fit' and interactions with the MHC class II molecules. The peptide scores calculated by the software lie between 0 and 1. Non-germline peptides that produced a high mean binding score (>0.55 in the iTope™ scoring function) were highlighted and, if ≥50% of the MHC class II binding peptides (i.e. 17 out of 34 alleles) had a high binding affinity (score >0.6), such peptides were defined as "promiscuous high affinity" MHC class II binding peptides (which are considered a high risk for containing CD4+ T cell epitopes). Peptides with ≥50% of the MHC class II binding peptides with a score >0.55 (but without a majority >0.6) were defined as "promiscuous moderate affinity" MHC class II binding peptides. Further analysis of the sequences was performed using the TCED™. The sequences were used to interrogate the TCED™ by BLAST search in order to identify any high sequence homology between peptides (T cell epitopes) from unrelated proteins that stimulated T cell responses in previous EpiScreen™ studies.

The sequences used by Schneck et al. incorporated two linkers, one at the N-terminus of HLA-A*02:01 to link with an N-terminal signal sequence and one at the C-terminus for fusion to the anti-CD28 VH domain (See FIG. 9 for example). For the N-terminal linker, sequence was analyzed from the signal sequence cleavage site through the linker and including the first 8 amino acids of HLA-A*02:01 mature protein. For the C-terminal linker, sequence was analyzed from the terminal 8 amino acids of HLA-A*02:01 α3 domain, through the linker sequence and up to the first 8 amino acids of the anti-CD28 VH domain.

Peptides with binding scores >0.6 (high affinity) bind to the majority (≥17) of MHC class II alleles (termed promiscuous high affinity binder). Moderate affinity binders with a binding score between 0.55 and 0.6 bind ≥17 MHC class II alleles. The N-terminal linker was found to contain two promiscuous MHC class II binding sequences, one high affinity (with p1 anchor at position 2) and one moderate affinity (with p1 anchor at position 4). The C-terminal linker was found to contain one promiscuous moderate affinity MHC class II binding peptide with p1 anchor at position 11.

A BLAST search of Antitope's T cell epitope database (TCED™) was carried out using the same sequences as used in the iTope™ analysis to determine any homology with previously identified epitopes. The TCED™ is used to search any test sequence against a large (>10,000 peptides) database of peptides derived from unrelated sequences which have been tested in EpiScreen™ T cell epitope mapping assays. Neither of the linker sequences was found to contain any 'hits' in the TCED™.

iTope™ was further used to assess sequence changes to the linkers in order to reduce their propensity for binding to MHC class II. It was noted that the N-terminal linker could be removed entirely such that the N-terminus of HLA-A*02:01 is fused directly either to the signal sequence provided in the pBFKsr vector or to its natural signal sequence. This would ensure that the N-terminus of the fusion protein would contain only human germline sequence and avoid the risk of T cell epitopes. The recommended linker sequences below were found to reduce MHC class II binding to background residual levels (<5 of the alleles bound by any 9mer), and to provide suitable restriction sites for cloning (although both sequences will require modification of the vector):

```
N-terminal linker:
 Q  V  Q  L  T  R  E  G  S  G  S  H  S  M  R  Y  F
CAGGTCCAACTGacgcgtGAGGGGTCCGGCTCTCACTCCATGAGGTATTTC
    Vector |    Linker    |      HLA-A*-02:01

C-terminal linker:
 E  G  L  P  K  P  L  T  W  A  R  E  V  S  E  V  K  L  Q
GAGGGTTTGCCCAAGCCCCTCACCTGGGctcgagAGGTGAGCGAGGTCAAGCTGCAG
        HLA-A*02:01    |      Linker     |   Anti-CD28
```

Example 3: Codon Optimization of Sequences and Expression Cloning

Codons were optimized using GeneOptimizer®, and optimized sequences were cloned for expression as shown below.

Sequences were engineered with PmeI restriction sites, Kozak sequence, and signal peptide for expression in NS0 cells. Translation starts immediately downstream of the Kozak sequence.

The full translated amino acid sequence of the HLA-IgG4HC fusion is shown in FIG. 10.

The translated sequence of LC3 (VK3) is shown in FIG. 11.

The translated sequence for HC1 is shown in FIG. 12.

The translated sequence for HC2 is shown in FIG. 13.

Human β2 microglobulin was also expressed.

Example 4: Expression in NS0 Cells

Based on Biacore affinity data and other considerations, the HC1::LC3 and HC2::LC3 heavy chain and light chain combinations were selected as the primary and secondary mAb candidates, respectively, for StableFast-NS0 cell line development.

The final vector map for the pBFksr::HC1::LC3 bicistronic expression vector for STABLEFAST-NS0 cell line generation is depicted in FIG. 14. Construction of pBFksr::HC2::LC3 was done using the same approaches.

Parental NS0 cells were expanded in supplemented serum-free growth medium. Upon establishment of health culture, ten million cells ($10 \times 10^6$) were transfected with 45 µg linearized (ΔPvuI) expression vector DNA. Cells were allowed to recover for 24 hours in bulk in growth medium. Following recovery, cells were washed in supplemented serum-free selective medium (cholesterol-), resuspended in the selective medium and distributed to 40×96-well plates at 200 µL per well. Actual distribution was 1140 cells/well and 840 cells/well for HC1::LC3 and HC2::LC3, respectively. Plates were incubated at 37° C., 5% CO2 for 1 week and fed with phenol red supplemented selective medium. At two weeks post-transfection, numerous wells were actively growing based on medium color change from red to yellow.

A total of 1,127 wells from the HC1::LC3 transfection were screened for human IgG expression by ELISA. A total of 612 wells from the HC2::LC3 transfection were screened. Based on IgG concentration, a total of 290 and 101 cell lines were scaled up to 24-well plates for HC1::LC3 and HC2::LC3, respectively. A 24-hour productivity assay was used to select best expressers for further analysis. Briefly, 24-well plates were seeded at $5 \times 10^5$ cells in 500 µL fresh medium. After 24 hours, supernatants were screened by ELISA. Based on IgG concentration, a total of 60 and 24 cell lines were scaled up to 6-well plates for HC1::LC3 and HC2::LC3, respectively.

A 3-day specific productivity assay was used to select best expressers for further analysis. Briefly, 6-well plates were seeded at 4×105 cells in 1.5 mL fresh medium. After 3 days, cells were counted and supernatants were screened by ELISA. Based on IgG concentration and growth, the average specific productivity rate or SPR in pg/cell/day can be calculated. Based on relative SPR, a total of 20 and 10 cell lines were scaled up to T-75 flasks for HC1::LC3 and HC2::LC3, respectively. The 3-day SPR assay was repeated at the T-75 scale to select the final cell lines for suspension adaptation and scale up for mAb production.

Five cell lines for each mAb were scaled up to 30-mL shaker culture and re-evaluated for SPR and growth. All suspension lines were banked. The best performing cell line for each mAb was scaled to spinner culture for small scale production.

Figure 15:
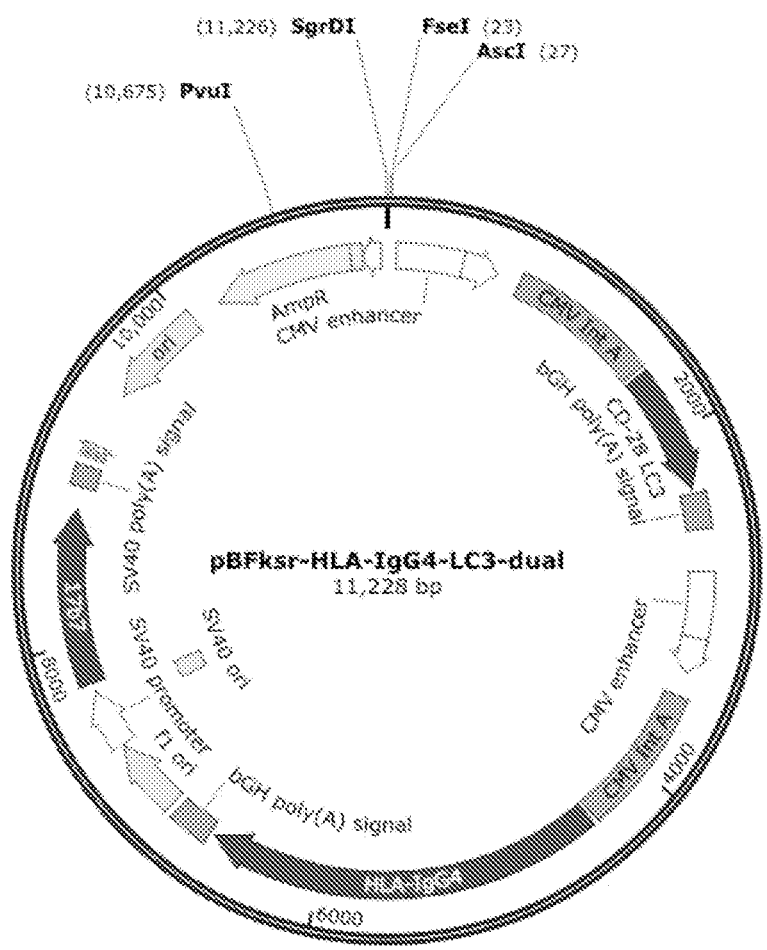
Figure 16:
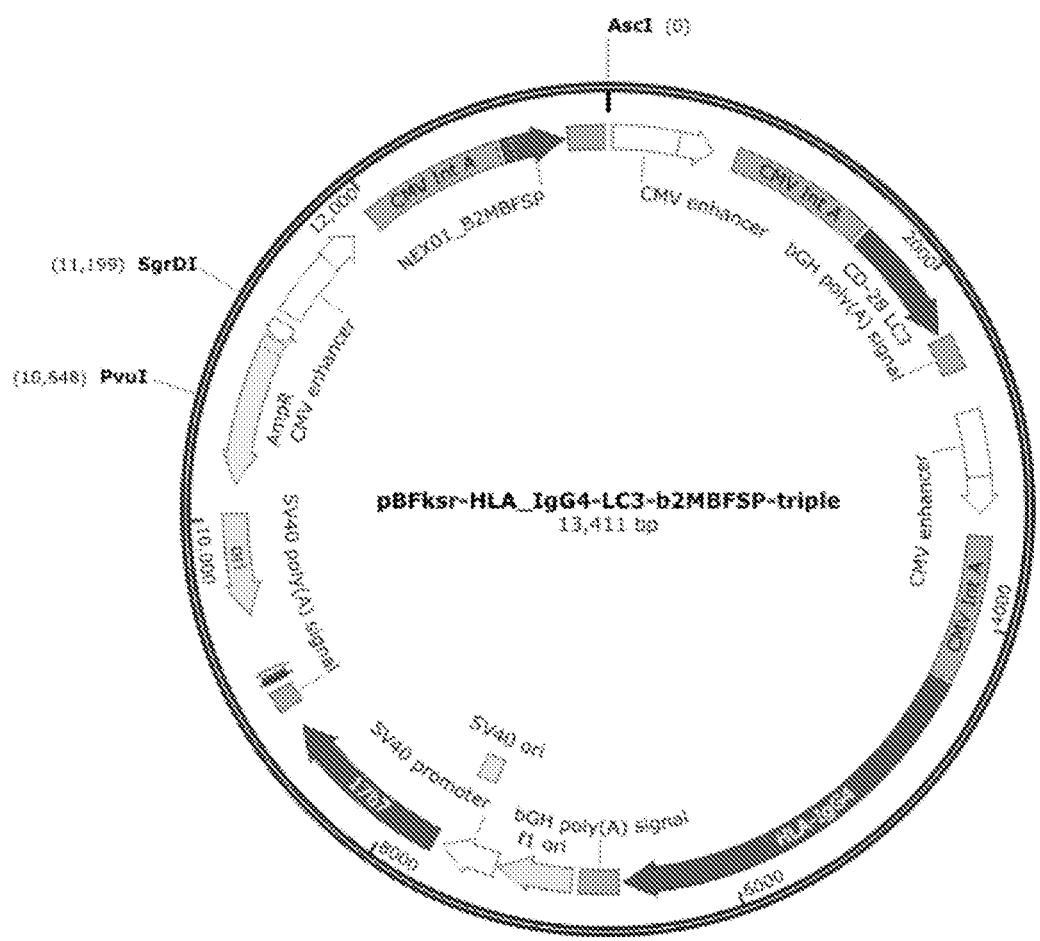

For the HLA-IgG4 Fusion Protein, the pBFksr::HLA-IgG4::LC3 bicistronic expression vector was constructed for STABLEFAST-NS0 cell line generation. The vector map is shown in FIG. 15. An expression cassette and vector containing the human β2 microglobulin gene was also created for a tricistronic expression vector that encodes all three fusion protein subunits (human HLA-IgG4 heavy chain fusion, a-CD28 light chain [LC3], and human β2 microglobulin). The tricistronic construct is shown in FIG. 16. Expression of all three genes was confirmed in transient HEK293 culture by ELISA and western blot analyses of supernatant.

Example 5: Functional Characterization of Humanized Ligands

Figure 17:
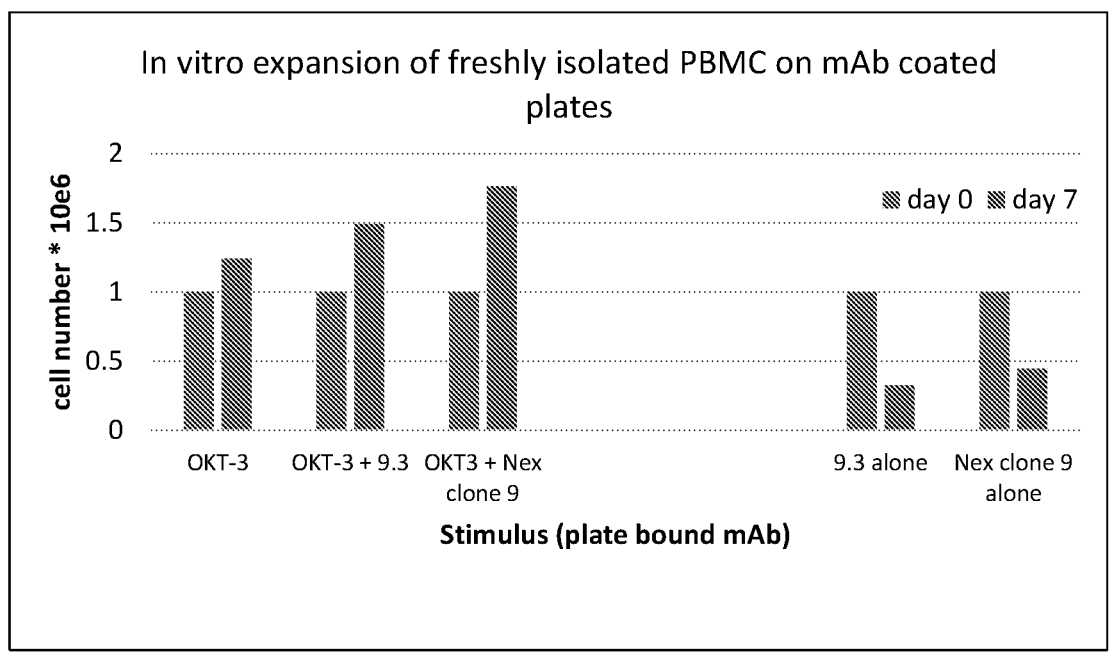
FIG. 17 shows that the humanized anti-CD28 mAb is not a super-agonist.

The humanized monoclonal antibody against CD28 was tested for its ability to induce expansion of freshly isolated PBMCs on mAb coated plates. As shown in FIG. 17, the humanized anti-CD28 functions similar to the parent close and is not a super agonist.

The humanized monoclonal antibody was tested for its ability to stain CD28 on a human T-cell line. The results are shown in FIG. 18. Panel (A) shows staining with murine anti-human CD8 mAb (clone 9.3, Isotype IgG2a). Peaks from left to right are: unstained cells, anti-IgG2a FITC, and anti-CD28+anti-IgG2a FITC. Panel (B) shows staining with humanized anti-CD28 (isotype IgG4). Peaks from left to right are: unstained cells, anti-IgG4 PE, anti-CD28 (35 ng)+anti-IgG4 PE, anti-CD28 (1 µg)+anti-IgG4 PE. The staining with humanized anti-CD28 can be blocked with Clone 9.3 mAb (not shown).

After purification of HLA-Ig, the antigen peptide loading efficiency is checked by ELISA using conformation dependent anti-HLA mAb to capture the peptide loaded protein (as described in Current protocols in Immunology Chapter 17.2). Reproducible loading efficiencies of ~90% for specific peptides (i.e. correct MHC restriction) is anticipated, compared to 0% for non-specific peptides (i.e. MHC mismatch).

Example 6: Nanoparticle Formulations

The following example demonstrates the synthesis of a nanoparticle having a core formed of PLGA (LA:GA=1:1) having a molecular weight of 35K. The corona of the particle is formed by PEG co-polymer from a mixture of PLGA-PEG-COOH or PLGA-PEG-maleimide, and PLGA-mPEG (methoxy PEG). The COOH and maleimide functional end groups allow for polypeptide conjugation. The methoxyPEG is inert with respect to functional end groups on the PEG chain. The PLGA portions have molecular weights of 10-30K (e.g., about 20K), and the molecular weight of the PEG portion is 3 and 5K. For this example, the nanoparticle is formed of 50% core PLGA (35K) and a mix of 25% PLGA-PEG-COOH and 25% PLGA-mPEG. The ratio of PLGA-PEG-COOH (or maleimide) and PLGA-mPEG allows for fine tuning of the ligand density on the surface of the particle. Similar particles can be prepared using other polymers, such as PLA and PLA-PEG, including with similar molecular weights and functional group density.

The PLGA inner core provides structure and size, and is a driver of the degradation rate. The infiltration of the core nanoparticle with water results in hydrolysis of the PLGA polymers and ultimately degradation of the nanoparticle.

The PLGA-mPEG polymer is inert with respect to functional groups that can be used to conjugate protein/peptide ligands and thus serves to provide a corona coating to the core nanoparticle that extends away from the hydrophobic PLGA core with a hydrophilic PEG outermost layer. Among other things, this helps prevent opsonization and removal of the nanoparticles by the mononuclear phagocyte system (MPS), including by limiting the binding of serum proteins (e.g., albumin).

The PLGA-PEG-COOH and PLGA-PEG-maleimide serves the same role as the PLGA-mPEG, and in addition, each PEG chain of the co-polymer is terminated with a functional group. After formation of the complete nanoparticle, the terminal COOH groups on the PLGA-PEG can be activated using EDC-Sulfo-NHS to create reactive groups that will form peptide bonds with available primary amine groups on proteins/peptides. Because this strategy does not control which available primary amine groups will conjugate to the activated —COOH groups on the PLGA-PEG polymers, the orientation of the ligands on the surface of the nanoparticle is not controlled, and thus not all will be biologically active.

An alternative is to prepare ligands that contain an unpaired cysteine residue, such as in the distal Fc region of a monoclonal IgG (IgG1 for the mouse ligands; IgG4 for the human ligands). This unpaired cysteine serves as a specific site for conjugation to the PLGA-PEG-maleimide (or other suitable functional group that can be used to form covalent bonds with unpaired cysteine residues). This allows each ligand to be conjugated in a site-specific manner that should result in a majority of the surface ligands being conjugated with an external orientation that supports biological activity. For example, the strategy has the binding portion of each ligand extending away from the hydrophobic PLGA portion of the nanoparticle and slightly external to the hydrophilic PEG chain of the corona.

The nanoparticles are in the size range of 20 to 200 nm; the polydispersity index (PDI) is 2 or less (e.g., 0.3 or less in some embodiments); and the zeta-potential (surface charge) is −15 mV to 0 mV. The nanoparticles with this composition, size, and charge are expected to have beneficial properties for in vivo PK/ADME. Specifically, they are small enough (<200 nm) to traffic to target tissues, including tumor microenvironment as well as move between blood and lymph; their hydrophilic PEG layer and slightly negative charge will help to retard binding of serum proteins and opsonization of the nanoparticles that would result in removal from circulation by cells of the MPS prior to distribution to target tissues; the polymer mix should result in a biodegradation rate measured in days to as much as 2 weeks; and the externally oriented protein ligands should provide for maximal biological activity with respect to binding of T cells with cognate TCRs and co-stimulatory receptors (e.g. CD28, 4-1BB). Further, in some embodiments the hydrophobic core of the nanoparticles could be loaded with a soluble payload (e.g., IL-2, anti-TGF-b, IL-21, or a small molecule drug) during formulation.

Exemplary polymer composition (total polymers weight 100 mg):

| | |
|---|---|
| PLGA 35 KDa | 50% w/w |
| PLGA-PEG-functional group 20 KDa-5 KDa | 25% w/w |
| PLGA-PEG-MeOH 20 KDa-5 KDa | 25% w/w |

The polymers were dissolved in 1 ml dichloromethane, 2.3 ml 5% PVA (20 KDa) was added and the solution was emulsified using probe sonicator. The emulsion was added to 46 ml 0.5% PVA solution and stirred for 2 hours until solvent was fully evaporated.

For purification, the particles were centrifuged at 3,700 rpm for 30 min, filtered through 0.45 micron filter and centrifuged at 10,000 rpm for 10 min to remove larger particles. The particles were washed with deionized water using centrifugal filtration (cut-off 100 KDa) at 2000 rpm to remove PVA.

The following protocol was used for conjugation of ligands. 40 mg of nanoparticles were dispersed in 10 mM HEPES buffer pH 6 at 1 mg/ml concentration. 80 mg EDC and 89.16 mg S—NHS were added to solution and stirred for 30 min. The excess of EDC and S—NHS was removed by centrifugal filter at 2500 rpm. The particles were re-dispersed in 1 mg/ml concentration in PBS and a mixture of Kb-Ig and anti-CD28 corresponding to 8 mg per mg particles was added to the solution. The particles were stirred at 4° C. overnight.

The particles were washed with PBS (17,000 rpm×50 min). After the second wash the particles were reconstituted in 100 mg/ml sucrose solution (total sucrose added was 4 mg).

Particles properties were determined.

| | Before Modification | | | Post Ligand Conjugation | | |
|---|---|---|---|---|---|---|
| | Size (DI) | PDI (DI) | z-potential (10 mm NaCl) | Size (DI) | PDI (DI) | z-potential (10 mm NaCl) |
| | 157.2 | 0.143 | −5.48 | 163.1 | 0.189 | −8.74 |
| | 156.3 | 0.174 | −6.15 | 162.1 | 0.160 | −8.78 |
| | 155.8 | 0.156 | −5.99 | 162.5 | 0.165 | −7.72 |
| Average | 156.4 | 0.158 | −5.87 | 162.6 | 0.171 | −8.41 |
| StDv | 0.7 | 0.016 | 0.35 | 0.5 | 0.016 | 0.60 |

Example 7: Fc Hinge Region Fusions

Figure 19:
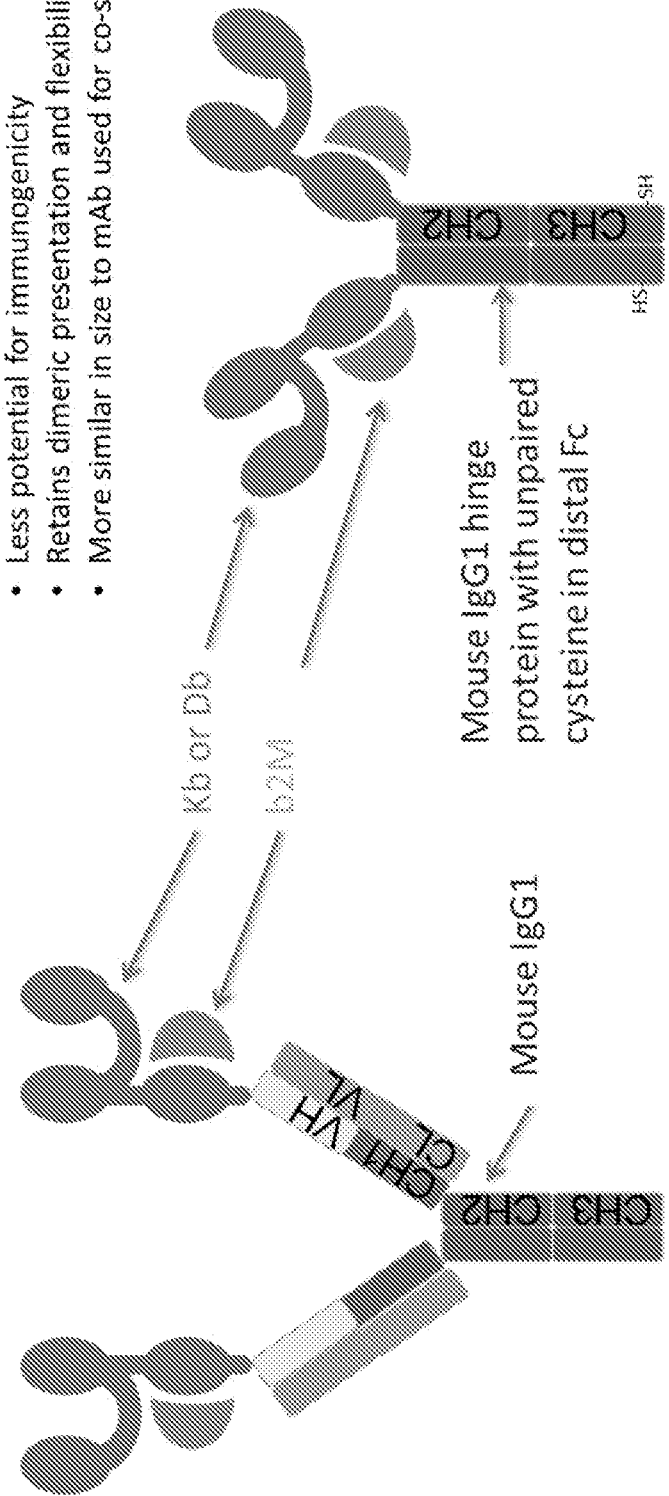
FIG. 19 shows design of smaller MHC-Ig fusion proteins based on fusion of the antigen presenting complex directly to the Fc hinge region.

Dimeric antigen presenting ligands were designed by fusing the antigen presenting complex (such as H2-Kb or HLA-2) directly to the Ig hinge region. H2-Kb Fc hinge protein contains the mouse class I Kb extracellular domain fused to the hinge-CH2-CH3 portion of a mouse IgG1, for which an unpaired cysteine residue has been engineered to replace a serine residue at position 231 of the heavy chain. This design is shown in FIG. 19.

Figure 27:
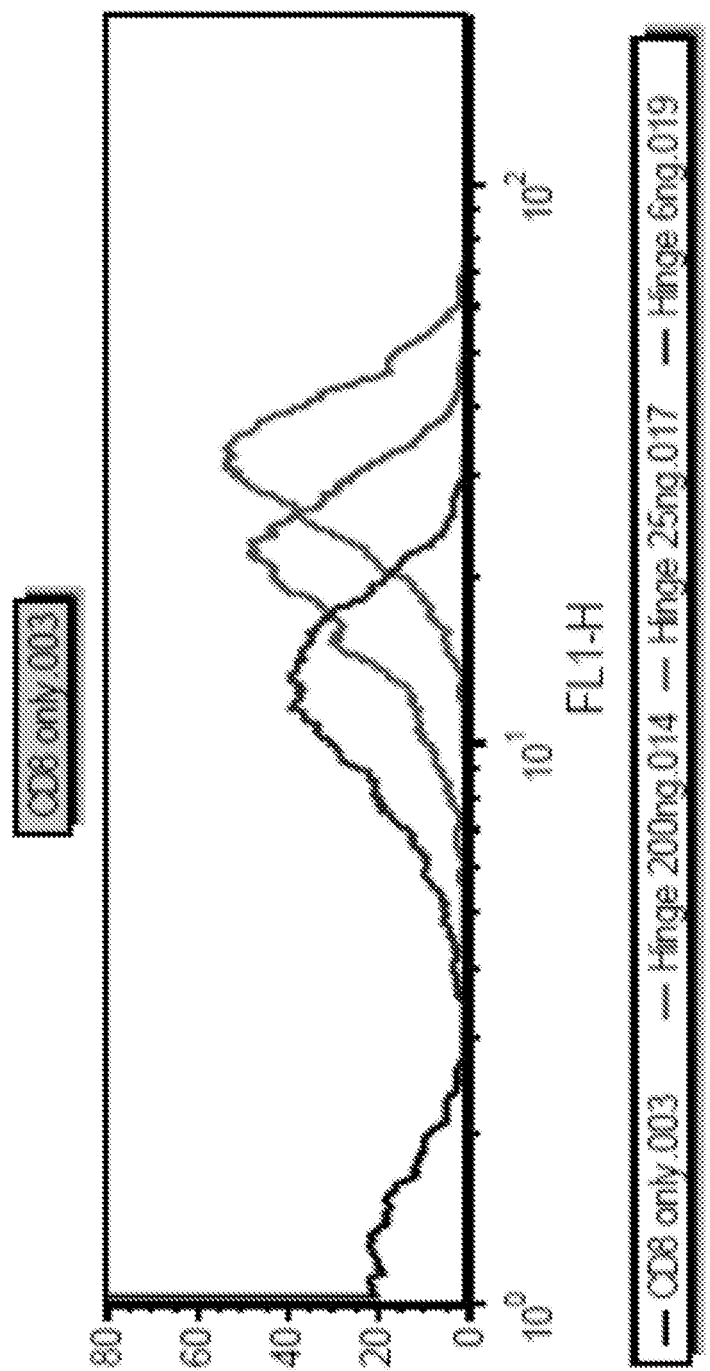
FIG. 27 shows that nano-aAPC based on Kb-SIY Fc-Hinge Protein specifically stain cognate target 2C T cells.

FIG. 27 shows that nano-aAPCs based on Kb-SIY Fc-Hinge Protein specifically stain cognate target 2C T cells.

Figure 29:
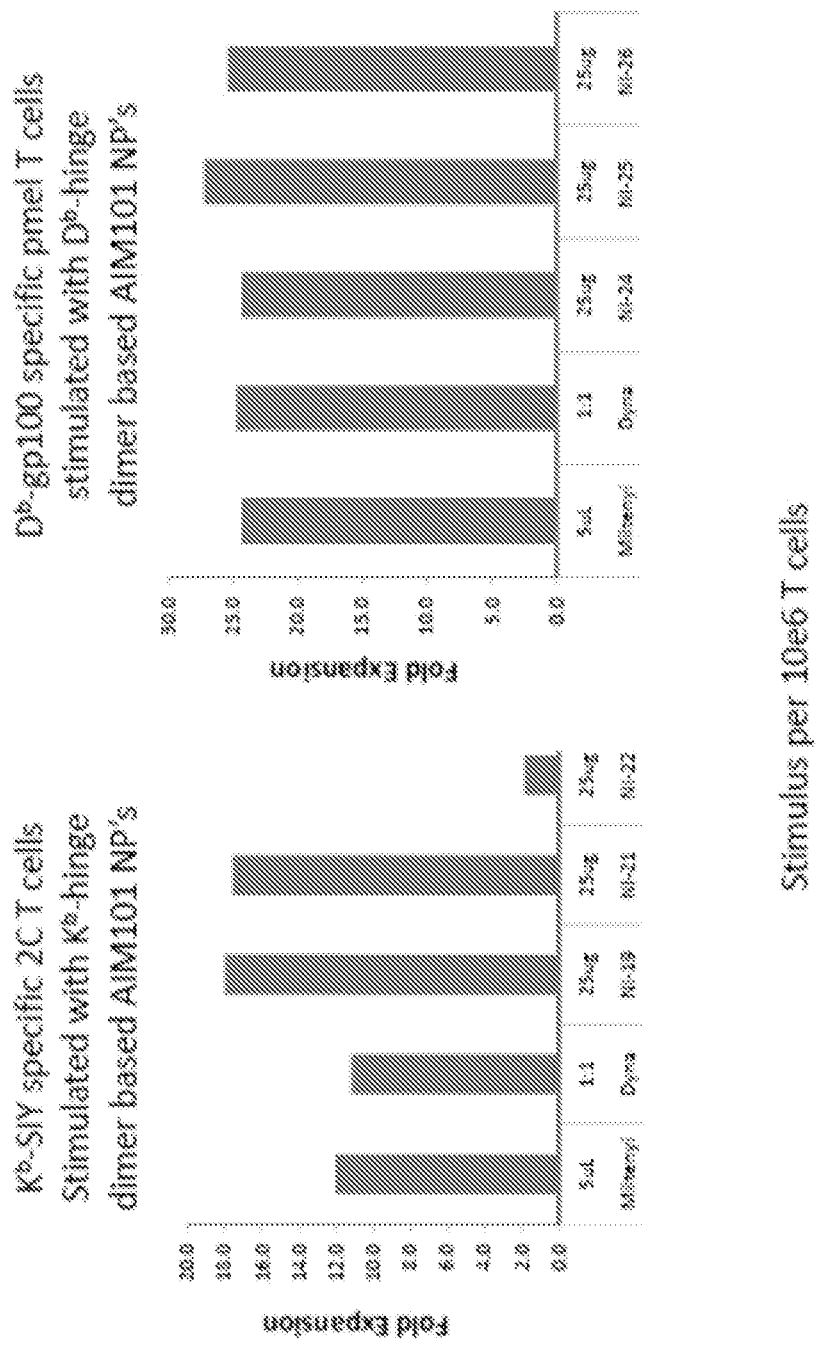
FIG. 29 shows expansion of $K^b$-specific 2C T cells (A) and $D^b$-gp100-specific pmel T cells using nano aAPCs containing hinge dimer constructs.

FIG. 29 shows expansion of Kb-specific 2C T cells (A) and Db-gp100-specific pmel T cells using nano aAPCs containing hinge dimer constructs. Miltenyi beads and Dyna beads (about 4.5 micron diameter) were used for comparison. The physical properties of batches NI-19, NI-21, NI-22 (containing $K^b$ hinge dimer), and batches NI-24 and NI-25 (containing $D^b$ hinge dimer) are shown in FIG. 32. NI-22 is a negative control.

Example 8: Exemplary Nano-aAPC Chemistries

Figure 20:
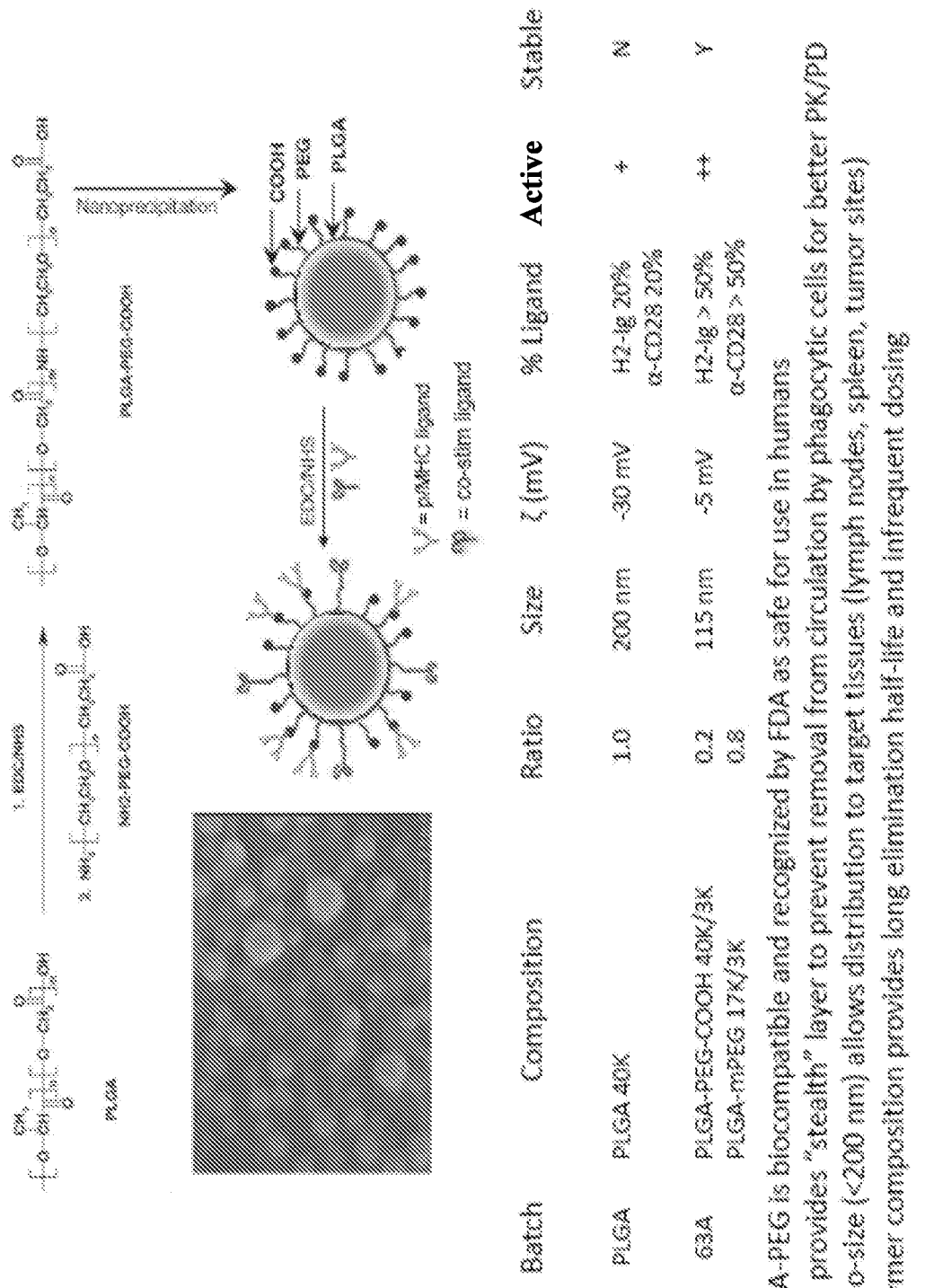
FIG. 20 shows a comparison between PLGA and PLGA-PEG-COOH nano-aAPC, with ligands conjugated through available primary amines. With a PEG-COOH:mPEG ratio of 1:4, beads were both stable and active.
Figure 21:
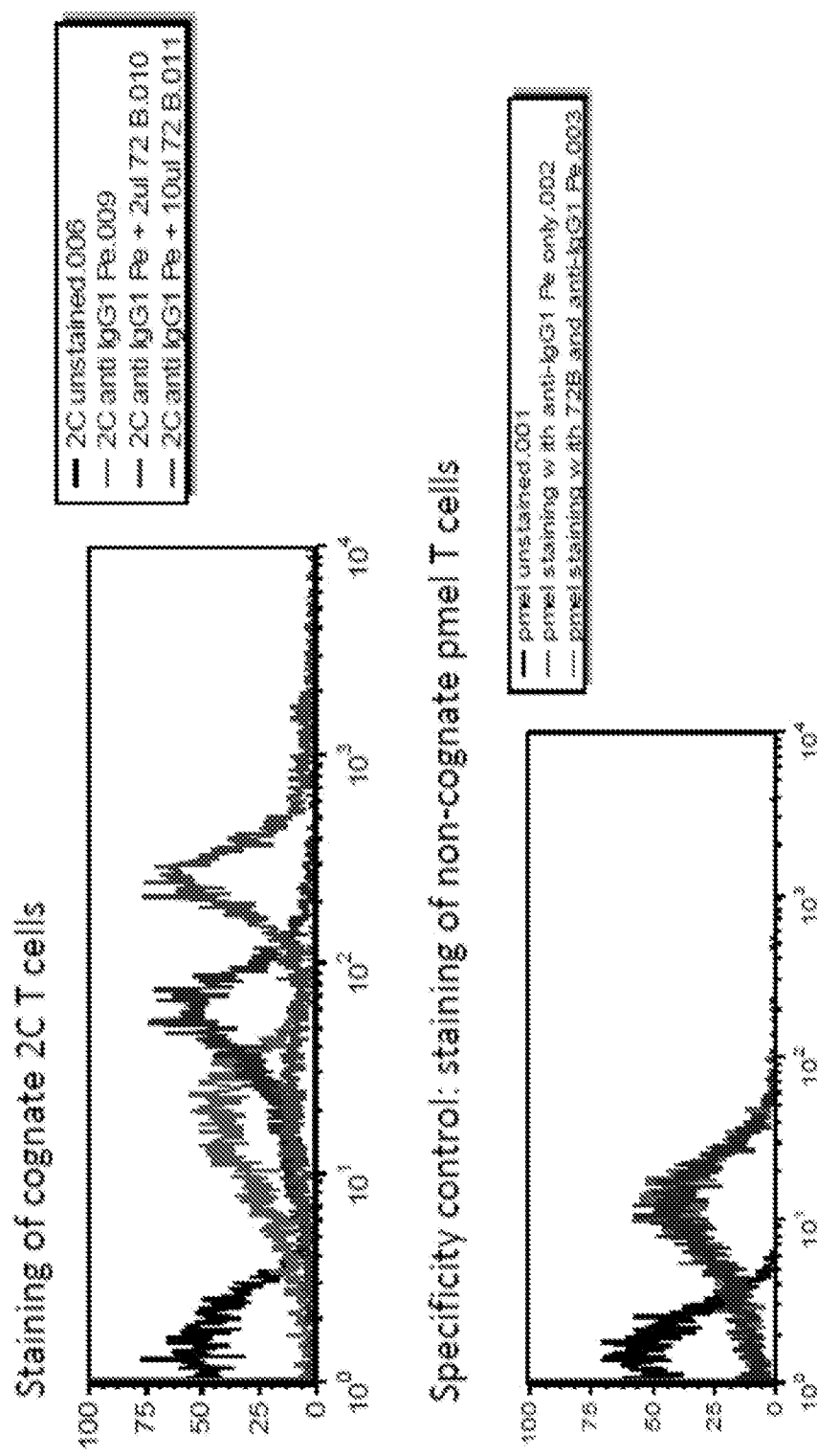
FIG. 21 shows that nano-aAPC specifically stain T cells with cognate TCRs. A FACS-based bioanalytical assay for TCR binding specificity is shown.

PLGA and PLGA-PEG-COOH nano-aAPCs were prepared with ligands conjugated through available primary amines. PLGA particles based on PLGA 40 (200 nm) did not show sufficient stability. Particles based on PLGA-PEG-COOH (40K/3K):PLGA-mPEG (17K/3K), and having a PEG:mPEG ratio of 1:4, showed good stability and activity. FIG. 20.

Figure 31:
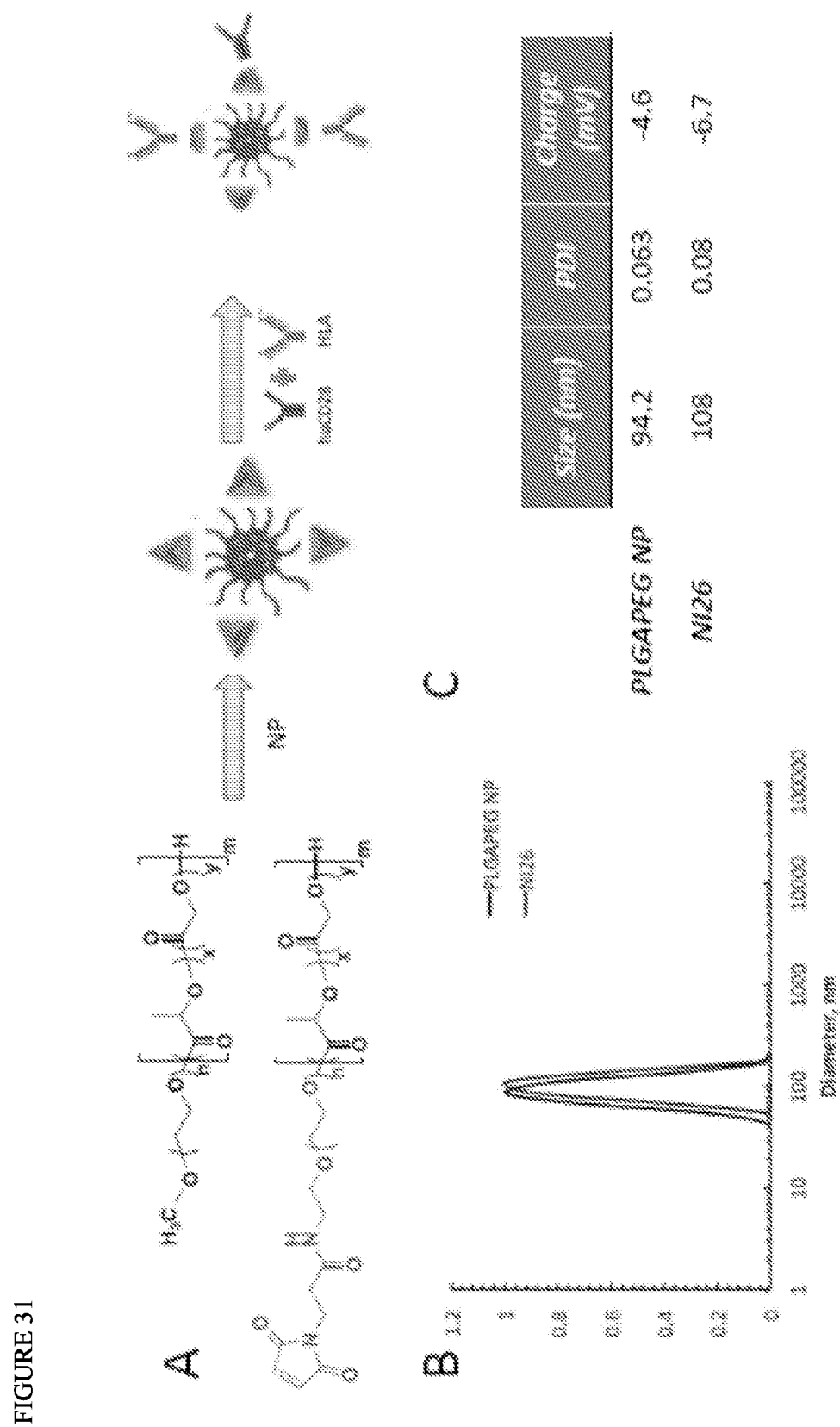
FIG. 31 illustrates exemplary nanoparticle formulations. (A) Conjuugation of ligands to particles with maleimide site-directed chemsitry; (B) characterization of particles by dynamic light scattering (DLS); (C) charge and PDI of NI-26 batch.

The following describes a process for site-directed conjugation of ligands, illustrated in FIG. 31. nano-aAPC were prepared with site-specific thiol conjugation of second generation ligands, including ligands based on the pHLA complexes fused to the Ig hinge region. Both murine and humanized versions of ligands were used to prepare nano-aAPC's. nano-APC's are prepared via two-step method. First, particles composed of PLGA-mPEG and PLGA-PEG-maleimide are prepared by a nanoprecipitation method. For example, a mixture of PLGA-mPEG and PLGA-PEG-maleimide (PLGA-PEG-maleimide % w/w varies between 1-55%) is dissolved in acetonitrile at final concentration of 50 mg/mL. This solution is injected at 5 mL/min using a syringe pump into a PVA solution (MnPVA=9 kDa, 0.5% w/v) under stirring. Organic:aqueous solvent jumps varied between 1:1 to 1:20. Microfluidics, confined impinging jets and multi-inlet vortex mixers devices can be used to prepare the particles ensuring superior consistency and narrow size distribution. Particles are purified by tangential flow filtration (TFF) or using Amicon centrifugal filters. Particles were then resuspended in conjugation buffer (HEPES 50 mM, EDTA 10 mM, pH=6.7). Finally, nano-aAPC's are prepared by conjugating a mixture of anti-CD28 and KbSIY/HLA ligands to particles. Conjugation of ligands to particles is allowed to proceed overnight at room temperature. Mass ratios of ligands:particles ranges from 1-500 μg/mg particle. The ratio of anti-CD28:Kb/HLA varies between 0-1. The unbound ligands are removed using SEC or TFF. Particles with an average size diameter of 90 nm and size distribution between 50-120 nm were prepared. FIG. 32.

Figure 22:
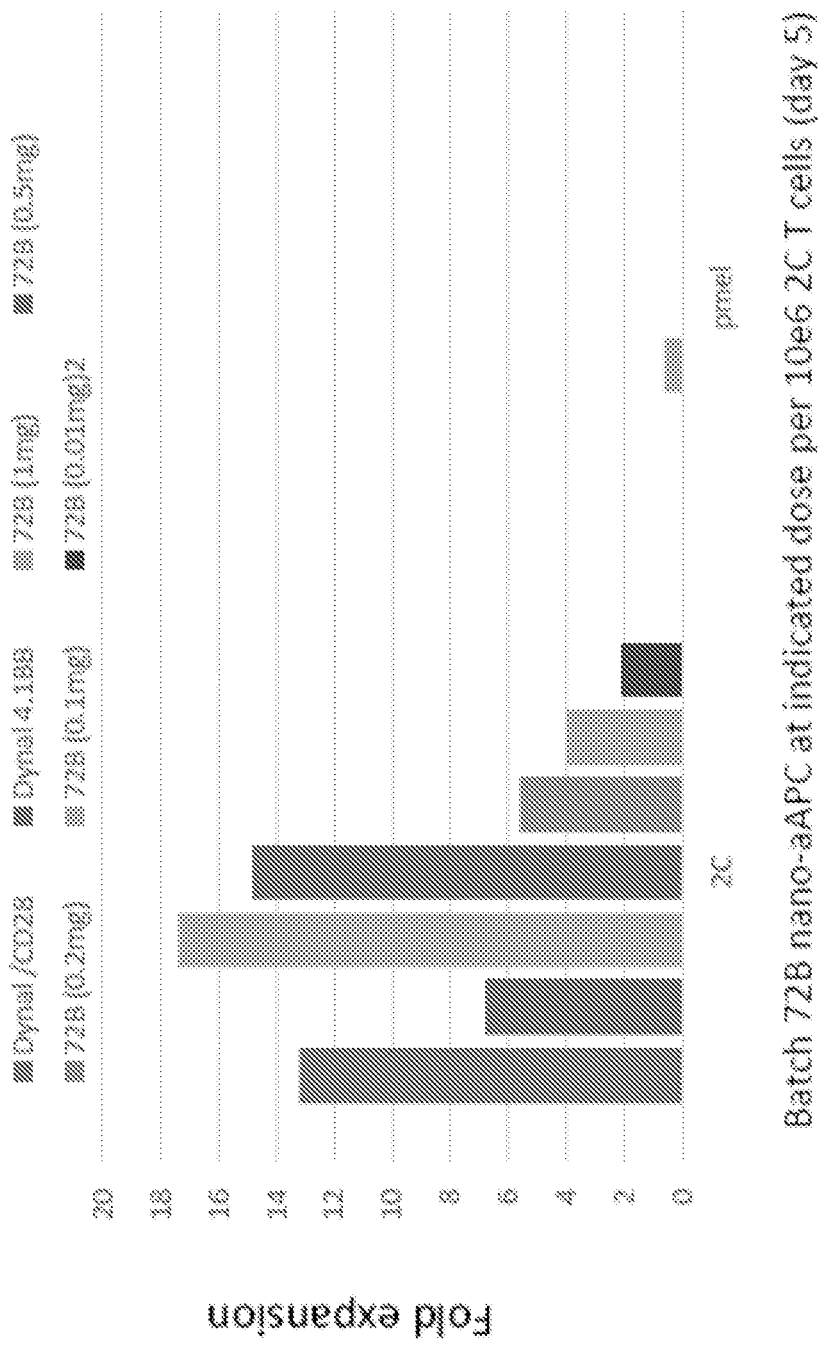
FIG. 22 shows that PLGA-PEG aAPC particles stimulate proliferation of antigen-specific T cells in a dose dependent manner.
Figure 23:
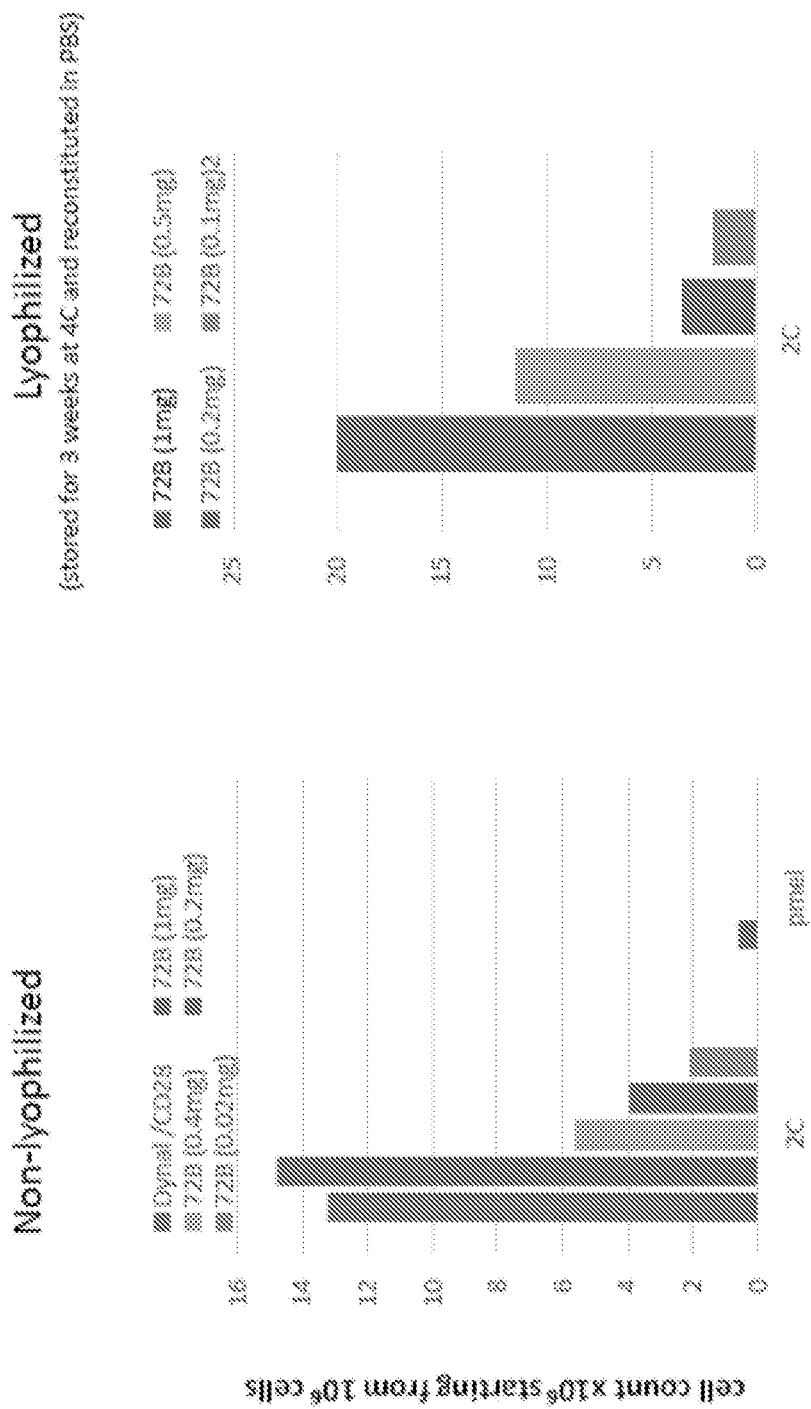
FIG. 23 shows that PLGA-PEG-based aAPCs are stable upon lyophilization.

As shown in FIG. 22, PLGA-PEG aAPC particles stimulate proliferation of antigen-specific T cells in a dose dependent manner. Further, and as shown in FIG. 23, PLGA-PEG-based aAPCs are stable upon lyophilization.

Figure 24:
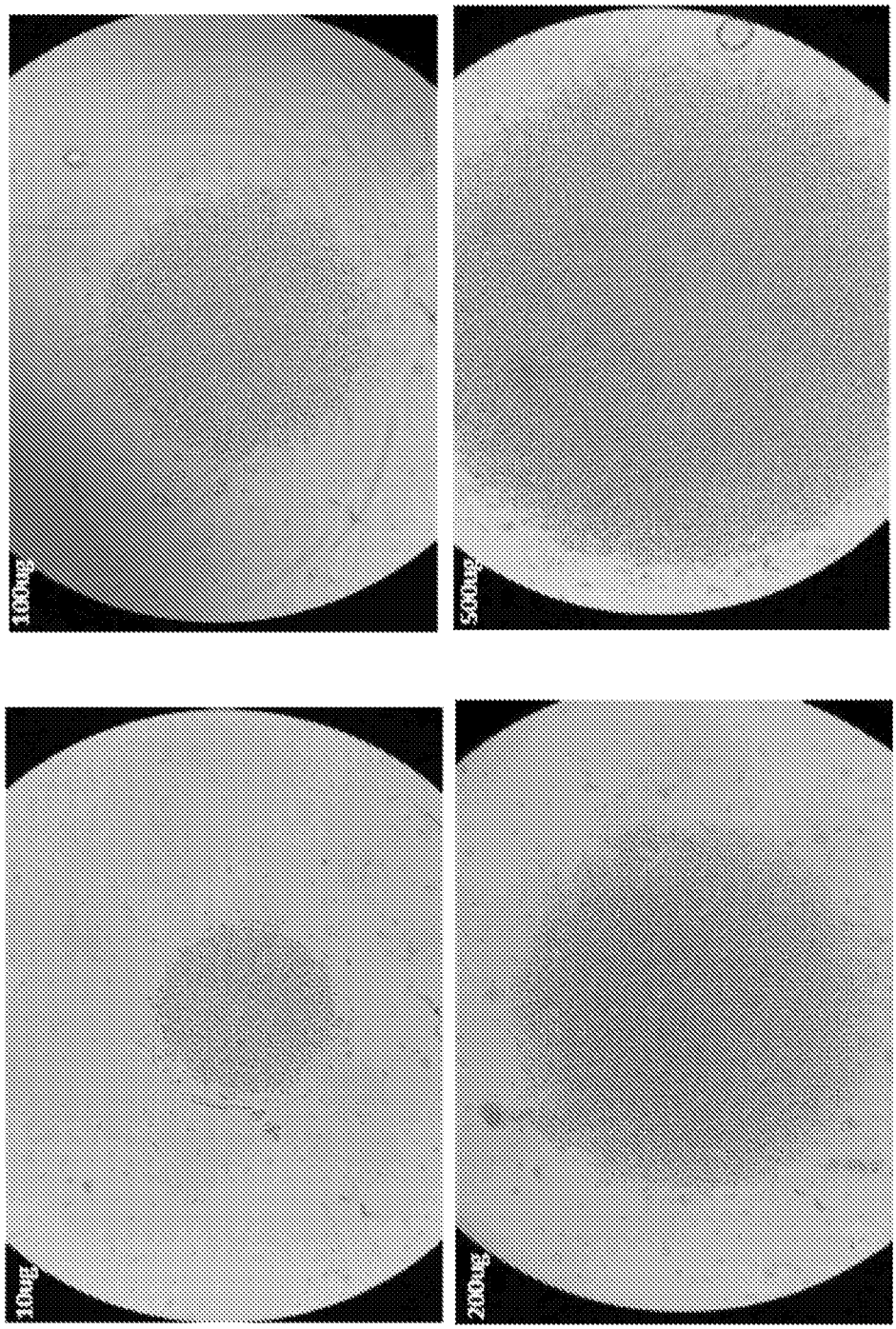
FIG. 24 shows a Day 4 culture of 2C T cells with increasing amounts of SIY-loaded PLGA-PEG nano aAPC.
Figure 25:
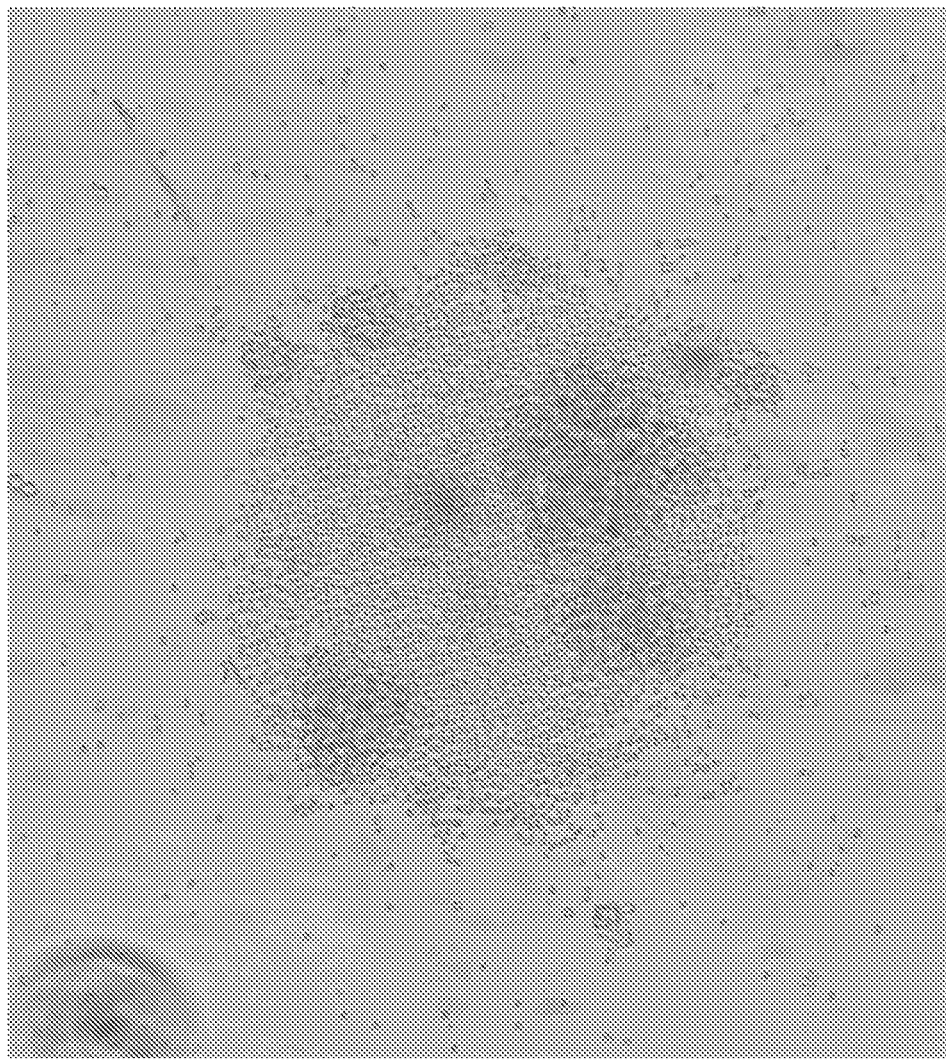
FIG. 25 shows T cell proliferation clusters 1 day after stimulation with nano-aAPCs.
Figure 26:
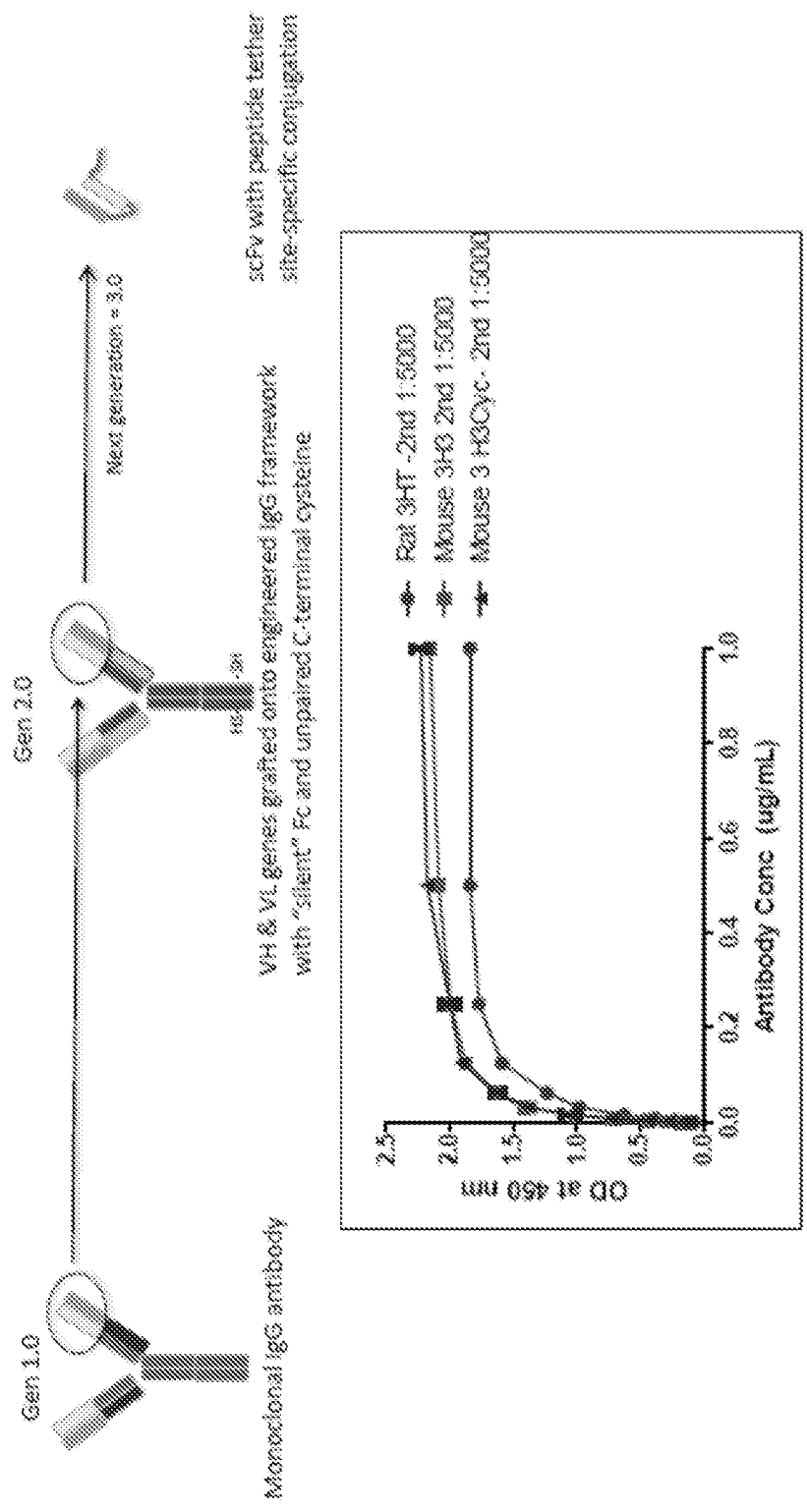
FIG. 26 shows binding activity of modified (Gen 2.0) co-stimulatory ligands.

A Day 4 culture of 2C T cells with increasing amounts of SIY-loaded PLGA-PEG nano aAPC is shown in FIG. 24, showing dose dependent expansion of antigen-specific T cells. FIG. 25 shows T cell proliferation clusters 1 day after stimulation with nano-aAPCs.

Figure 28:
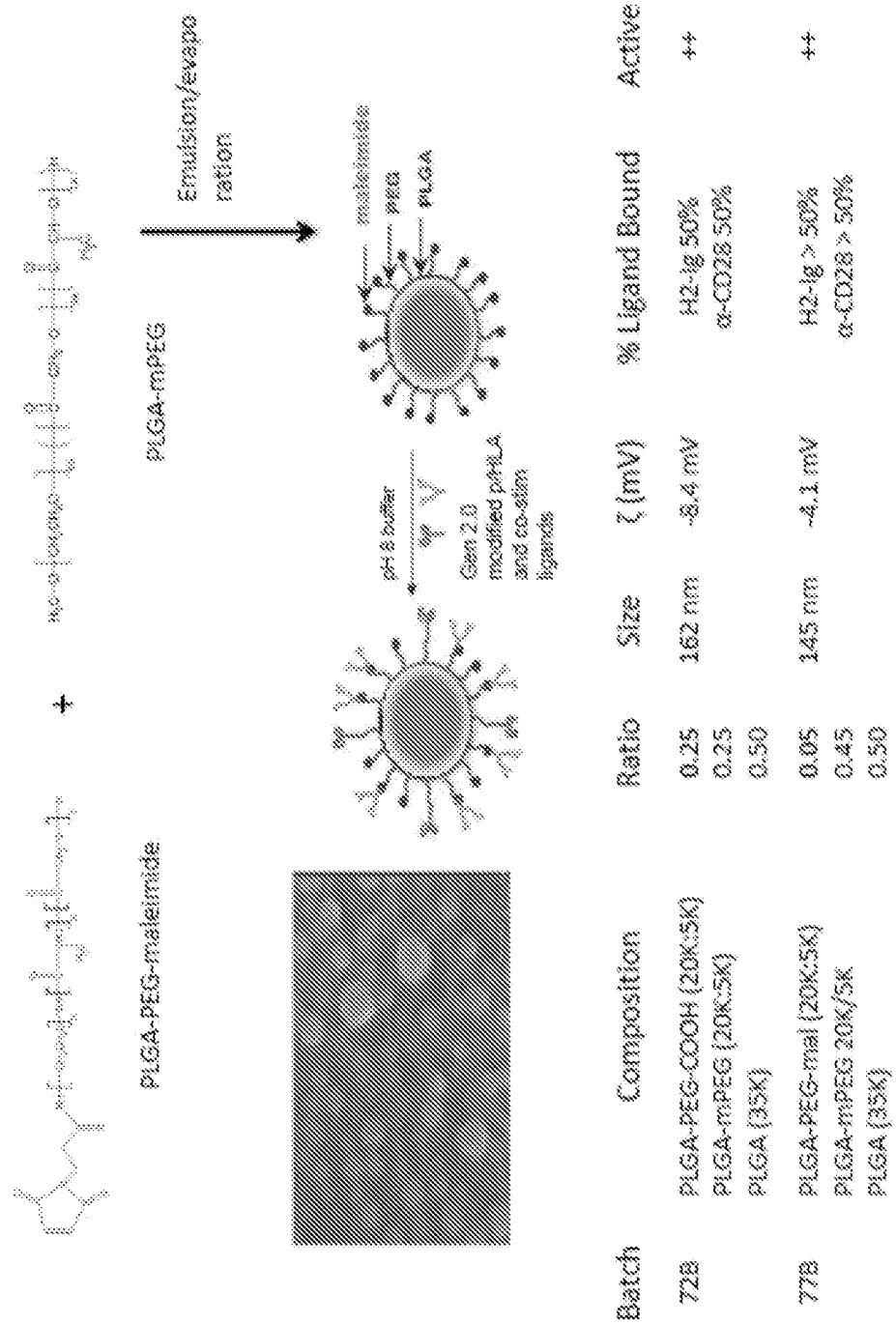
FIG. 28 shows nano-aAPC with site-specific thiol conjugation of ligands. Beads contained a 1:1 ratio of PEG-COOH to mPEG polymers (72B) or a 1:9 PEG-mal:mPEG ratio (77B). Both were stable and active.

FIG. 28 shows nano-aAPC with site-specific thiol conjugation of ligands. Beads contained a 1:1 ratio of PEG-COOH to mPEG polymers (batch 72B) or a 1:9 PEG-mal:mPEG ratio (batch 77B). Both were stable and active.

Figure 30:
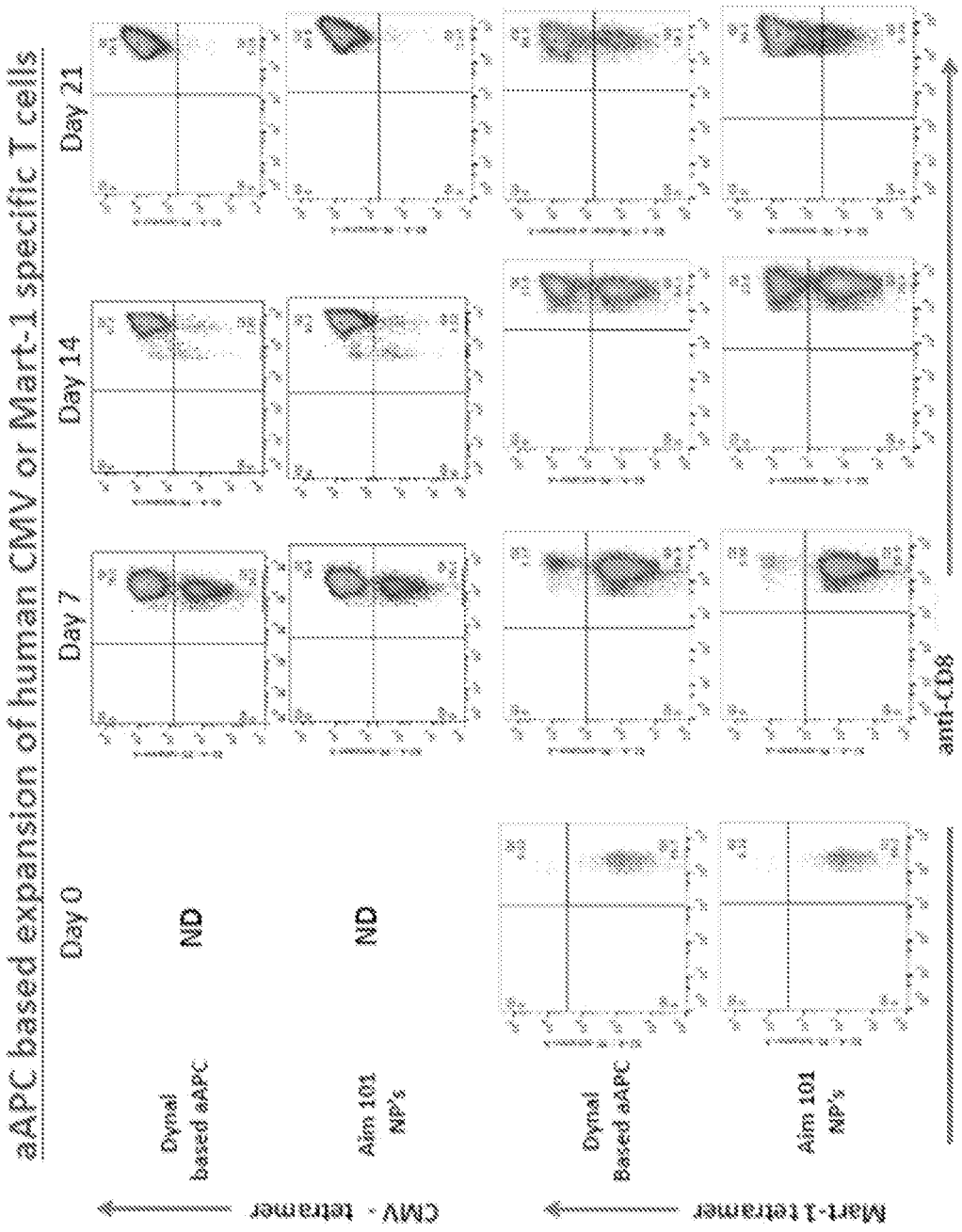
FIG. 30 shows nano aAPC-based expansion of human CMV or MART-1 specific T cells. Dynal-based APCs are shown for comparison.

FIG. 30 shows nano aAPC-based expansion of human CMV or MART-1 specific T cells. Dynal-based APCs are shown for comparison. Expansion is shown at Day 0, Day 7, Day 14, and Day 21. CD8 staining is shown on the X-axis, and antigen-specific T cells are identified on the Y-axis based on peptide-WIC tetramer staining.

FIG. 31 illustrates exemplary nanoparticle formulations, including conjugation of ligands to particles with maleimide site directed chemistry (A); characterization of particles by dynamic light scattering (DLS) (B); and characterization of size, charge and PDI of a representative batch (N126). N126 particles show a peak size distribution at around 108 nm, PDI of 0.08, and charge of −6.7 mV.

INCORPORATION BY REFERENCE

All patents and publications referenced herein are hereby incorporated by reference in their entireties.

---

SEQUENCE LISTING

```
<160> NUMBER OF SEQ ID NOS: 34

<210> SEQ ID NO 1
<211> LENGTH: 360
<212> TYPE: DNA
<213> ORGANISM: Artificial Sequence
<220> FEATURE:
<223> OTHER INFORMATION: Synthetic sequence (Humanized variable heavy
      sequence for anit-CD28)
<220> FEATURE:
<221> NAME/KEY: CDS
<222> LOCATION: (1)..(360)

<400> SEQUENCE: 1 gag gtg aag ctg cag cag tca gga cct ggc ctg gtg aag ccc tca gag      48
Glu Val Lys Leu Gln Gln Ser Gly Pro Gly Leu Val Lys Pro Ser Glu
1               5                   10                  15 acc ctg tcc ctc act tgt act gtc tct ggg ttt tca tta agc gac tat      96
Thr Leu Ser Leu Thr Cys Thr Val Ser Gly Phe Ser Leu Ser Asp Tyr
            20                  25                  30 ggt gtt cat tgg gtt cgc cag gct cca gga aag gga ctg gag tgg ctg     144
Gly Val His Trp Val Arg Gln Ala Pro Gly Lys Gly Leu Glu Trp Leu
        35                  40                  45 gga gta ata tgg gct ggt gga ggc acg aat tat aat tcg gct ctc atg     192
Gly Val Ile Trp Ala Gly Gly Gly Thr Asn Tyr Asn Ser Ala Leu Met
    50                  55                  60 tcc aga aag acc atc agc aaa gac aac tcc aag agc caa gtt ttc tta     240
Ser Arg Lys Thr Ile Ser Lys Asp Asn Ser Lys Ser Gln Val Phe Leu
65                  70                  75                  80
```

```
aaa atg aac agt ctg aca gct gct gac aca gcc gtg tat tac tgt gcc    288
Lys Met Asn Ser Leu Thr Ala Ala Asp Thr Ala Val Tyr Tyr Cys Ala
                85                  90                  95 aga gat aag gga tac tcc tat tac tat tct atg gac tac tgg ggc caa    336
Arg Asp Lys Gly Tyr Ser Tyr Tyr Tyr Ser Met Asp Tyr Trp Gly Gln
           100                 105                 110 ggc acc ctg gtc acc gtc tcc tca                                    360
Gly Thr Leu Val Thr Val Ser Ser
           115                 120

<210> SEQ ID NO 2
<211> LENGTH: 120
<212> TYPE: PRT
<213> ORGANISM: Artificial Sequence
<220> FEATURE:
<223> OTHER INFORMATION: Synthetic Construct

<400> SEQUENCE: 2

Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val His Trp Val Arg Gln Ala Pro Gly Lys Gly Leu Glu Trp Leu
        35                  40                  45

Gly Val Ile Trp Ala Gly Gly Thr Asn Tyr Asn Ser Ala Leu Met
    50                  55                  60

Ser Arg Lys Thr Ile Ser Lys Asp Asn Ser Lys Ser Gln Val Phe Leu
65                  70                  75                  80

Lys Met Asn Ser Leu Thr Ala Ala Asp Thr Ala Val Tyr Tyr Cys Ala
                85                  90                  95

Arg Asp Lys Gly Tyr Ser Tyr Tyr Tyr Ser Met Asp Tyr Trp Gly Gln
           100                 105                 110

Gly Thr Leu Val Thr Val Ser Ser
           115                 120

<210> SEQ ID NO 3
<211> LENGTH: 360
<212> TYPE: DNA
<213> ORGANISM: Artificial Sequence
<220> FEATURE:
<223> OTHER INFORMATION: Synthetic sequence (Anti-CD28 VH2)
<220> FEATURE:
<221> NAME/KEY: CDS
<222> LOCATION: (1)..(360)

<400> SEQUENCE: 3 gag gtg aag ctg cag cag tca gga cct ggc ctg gtg aag ccc tca gag    48
Glu Val Lys Leu Gln Gln Ser Gly Pro Gly Leu Val Lys Pro Ser Glu
1               5                   10                  15 acc ctg tcc ctc act tgt act gtc tct ggg ttt tca tta agc gac tat    96
Thr Leu Ser Leu Thr Cys Thr Val Ser Gly Phe Ser Leu Ser Asp Tyr
            20                  25                  30 ggt gtt cat tgg gtt cgc cag gct cca gga aag gga ctg gag tgg ctg    144
Gly Val His Trp Val Arg Gln Ala Pro Gly Lys Gly Leu Glu Trp Leu
        35                  40                  45 gga gta ata tgg gct ggt gga ggc acg aat tat aat tcg gct ctc atg    192
Gly Val Ile Trp Ala Gly Gly Thr Asn Tyr Asn Ser Ala Leu Met
    50                  55                  60 tcc aga aag acc atc agc aaa gac aac tcc aag agc caa gtt tcc tta    240
Ser Arg Lys Thr Ile Ser Lys Asp Asn Ser Lys Ser Gln Val Ser Leu
65                  70                  75                  80
```

```
aaa atg agc agt gtg aca gct gct gac aca gcc gtg tat tac tgt gcc       288
Lys Met Ser Ser Val Thr Ala Ala Asp Thr Ala Val Tyr Tyr Cys Ala
            85                  90                  95 aga gat aag gga tac tcc tat tac tat tct atg gac tac tgg ggc caa       336
Arg Asp Lys Gly Tyr Ser Tyr Tyr Tyr Ser Met Asp Tyr Trp Gly Gln
            100                 105                 110 ggc acc ctg gtc acc gtc tcc tca                                       360
Gly Thr Leu Val Thr Val Ser Ser
            115                 120

<210> SEQ ID NO 4
<211> LENGTH: 120
<212> TYPE: PRT
<213> ORGANISM: Artificial Sequence
<220> FEATURE:
<223> OTHER INFORMATION: Synthetic Construct

<400> SEQUENCE: 4

Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val His Trp Val Arg Gln Ala Pro Gly Lys Gly Leu Glu Trp Leu
            35                  40                  45

Gly Val Ile Trp Ala Gly Gly Gly Thr Asn Tyr Asn Ser Ala Leu Met
        50                  55                  60

Ser Arg Lys Thr Ile Ser Lys Asp Asn Ser Lys Ser Gln Val Ser Leu
65              70                  75                  80

Lys Met Ser Ser Val Thr Ala Ala Asp Thr Ala Val Tyr Tyr Cys Ala
            85                  90                  95

Arg Asp Lys Gly Tyr Ser Tyr Tyr Tyr Ser Met Asp Tyr Trp Gly Gln
            100                 105                 110

Gly Thr Leu Val Thr Val Ser Ser
            115                 120

<210> SEQ ID NO 5
<211> LENGTH: 360
<212> TYPE: DNA
<213> ORGANISM: Artificial Sequence
<220> FEATURE:
<223> OTHER INFORMATION: Synthetic sequence ((Anti-CD28 VH3)
<220> FEATURE:
<221> NAME/KEY: CDS
<222> LOCATION: (1)..(360)

<400> SEQUENCE: 5 gag gtg aag ctg cag cag tca gga cct ggc ctg gtg aag ccc tca gag        48
Glu Val Lys Leu Gln Gln Ser Gly Pro Gly Leu Val Lys Pro Ser Glu
1               5                   10                  15 acc ctg tcc ctc act tgt act gtc tct ggg ttt tca tta agc gac tat        96
Thr Leu Ser Leu Thr Cys Thr Val Ser Gly Phe Ser Leu Ser Asp Tyr
            20                  25                  30 ggt gtt cat tgg gtt cgc cag gct cca gga aag gga ctg gag tgg ctg       144
Gly Val His Trp Val Arg Gln Ala Pro Gly Lys Gly Leu Glu Trp Leu
            35                  40                  45 gga gta ata tgg gct ggt gga ggc acg aat tat aat tcg gct ctc atg       192
Gly Val Ile Trp Ala Gly Gly Gly Thr Asn Tyr Asn Ser Ala Leu Met
        50                  55                  60 tcc aga gtg acc atc agc aaa gac aac tcc aag agc caa gtt tcc tta       240
Ser Arg Val Thr Ile Ser Lys Asp Asn Ser Lys Ser Gln Val Ser Leu
65              70                  75                  80
```

```
aaa ctg agc agt gtg aca gct gct gac aca gcc gtg tat tac tgt gcc    288
Lys Leu Ser Ser Val Thr Ala Ala Asp Thr Ala Val Tyr Tyr Cys Ala
                85                  90                  95 aga gat aag gga tac tcc tat tac tat tct atg gac tac tgg ggc caa    336
Arg Asp Lys Gly Tyr Ser Tyr Tyr Tyr Ser Met Asp Tyr Trp Gly Gln
            100                 105                 110 ggc acc ctg gtc acc gtc tcc tca                                    360
Gly Thr Leu Val Thr Val Ser Ser
        115                 120

<210> SEQ ID NO 6
<211> LENGTH: 120
<212> TYPE: PRT
<213> ORGANISM: Artificial Sequence
<220> FEATURE:
<223> OTHER INFORMATION: Synthetic Construct

<400> SEQUENCE: 6

Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val His Trp Val Arg Gln Ala Pro Gly Lys Gly Leu Glu Trp Leu
        35                  40                  45

Gly Val Ile Trp Ala Gly Gly Thr Asn Tyr Asn Ser Ala Leu Met
    50                  55                  60

Ser Arg Val Thr Ile Ser Lys Asp Asn Ser Lys Ser Gln Val Ser Leu
65              70                  75                  80

Lys Leu Ser Ser Val Thr Ala Ala Asp Thr Ala Val Tyr Tyr Cys Ala
            85                  90                  95

Arg Asp Lys Gly Tyr Ser Tyr Tyr Tyr Ser Met Asp Tyr Trp Gly Gln
        100                 105                 110

Gly Thr Leu Val Thr Val Ser Ser
            115                 120

<210> SEQ ID NO 7
<211> LENGTH: 333
<212> TYPE: DNA
<213> ORGANISM: Artificial Sequence
<220> FEATURE:
<223> OTHER INFORMATION: Synthetic sequence (Anti-CD28 VK1)
<220> FEATURE:
<221> NAME/KEY: CDS
<222> LOCATION: (1)..(333)

<400> SEQUENCE: 7 gac atc gag ctc act cag tct cca gat tct ttg gct gtg tct cta ggg    48
Asp Ile Glu Leu Thr Gln Ser Pro Asp Ser Leu Ala Val Ser Leu Gly
1               5                   10                  15 gag aga gcc acc atc aac tgc aga gcc agt gag agt gtt gaa tat tat    96
Glu Arg Ala Thr Ile Asn Cys Arg Ala Ser Glu Ser Val Glu Tyr Tyr
            20                  25                  30 gtc aca agt tta atg cag tgg tac cag cag aag cca gga cag cca ccc    144
Val Thr Ser Leu Met Gln Trp Tyr Gln Gln Lys Pro Gly Gln Pro Pro
        35                  40                  45 aaa ctc ctc atc ttt gct gca tcc aac gta gaa tct ggg gtc cct gac    192
Lys Leu Leu Ile Phe Ala Ala Ser Asn Val Glu Ser Gly Val Pro Asp
    50                  55                  60 agg ttt agt ggc agt ggg tct ggg aca aac ttc acc ctc acc atc tct    240
Arg Phe Ser Gly Ser Gly Ser Gly Thr Asn Phe Thr Leu Thr Ile Ser
65              70                  75                  80
```

```
tct ctg cag gag gag gat gtt gca atg tat ttc tgt cag caa agt agg    288
Ser Leu Gln Glu Glu Asp Val Ala Met Tyr Phe Cys Gln Gln Ser Arg
                85                  90                  95 aag gtt cct tac acg ttc gga ggg ggg acc aag gtg gaa ata aaa        333
Lys Val Pro Tyr Thr Phe Gly Gly Gly Thr Lys Val Glu Ile Lys
            100                 105                 110

<210> SEQ ID NO 8
<211> LENGTH: 111
<212> TYPE: PRT
<213> ORGANISM: Artificial Sequence
<220> FEATURE:
<223> OTHER INFORMATION: Synthetic Construct

<400> SEQUENCE: 8

Asp Ile Glu Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Asp
    50                  55                  60

Arg Phe Ser Gly Ser Gly Ser Gly Thr Asn Phe Thr Leu Thr Ile Ser
65                  70                  75                  80

Ser Leu Gln Glu Glu Asp Val Ala Met Tyr Phe Cys Gln Gln Ser Arg
                85                  90                  95

Lys Val Pro Tyr Thr Phe Gly Gly Gly Thr Lys Val Glu Ile Lys
            100                 105                 110

<210> SEQ ID NO 9
<211> LENGTH: 333
<212> TYPE: DNA
<213> ORGANISM: Artificial Sequence
<220> FEATURE:
<223> OTHER INFORMATION: Synthetic sequence (Anti-CD28 VK2)
<220> FEATURE:
<221> NAME/KEY: CDS
<222> LOCATION: (1)..(333)

<400> SEQUENCE: 9 gac atc gag ctc act cag tct cca gat tct ttg gct gtg tct cta ggg    48
Asp Ile Glu Leu Thr Gln Ser Pro Asp Ser Leu Ala Val Ser Leu Gly
1               5                   10                  15 gag aga gcc acc atc aac tgc aga gcc agt gag agt gtt gaa tat tat    96
Glu Arg Ala Thr Ile Asn Cys Arg Ala Ser Glu Ser Val Glu Tyr Tyr
            20                  25                  30 gtc aca agt tta atg cag tgg tac cag cag aag cca gga cag cca ccc   144
Val Thr Ser Leu Met Gln Trp Tyr Gln Gln Lys Pro Gly Gln Pro Pro
        35                  40                  45 aaa ctc ctc atc ttt gct gca tcc aac gta gaa tct ggg gtc cct gac   192
Lys Leu Leu Ile Phe Ala Ala Ser Asn Val Glu Ser Gly Val Pro Asp
    50                  55                  60 agg ttt agt ggc agt ggg tct ggg aca aac ttc acc ctc acc atc tct   240
Arg Phe Ser Gly Ser Gly Ser Gly Thr Asn Phe Thr Leu Thr Ile Ser
65                  70                  75                  80 tct ctg cag gcc gag gat gtt gca atg tat ttc tgt cag caa agt agg   288
Ser Leu Gln Ala Glu Asp Val Ala Met Tyr Phe Cys Gln Gln Ser Arg
                85                  90                  95 aag gtt cct tac acg ttc gga ggg ggg acc aag gtg gaa ata aaa       333
Lys Val Pro Tyr Thr Phe Gly Gly Gly Thr Lys Val Glu Ile Lys
            100                 105                 110
```

<210> SEQ ID NO 10
<211> LENGTH: 111
<212> TYPE: PRT
<213> ORGANISM: Artificial Sequence
<220> FEATURE:
<223> OTHER INFORMATION: Synthetic Construct

<400> SEQUENCE: 10

Asp Ile Glu Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Asp
    50                  55                  60

Arg Phe Ser Gly Ser Gly Ser Gly Thr Asn Phe Thr Leu Thr Ile Ser
65                  70                  75                  80

Ser Leu Gln Ala Glu Asp Val Ala Met Tyr Phe Cys Gln Gln Ser Arg
                85                  90                  95

Lys Val Pro Tyr Thr Phe Gly Gly Gly Thr Lys Val Glu Ile Lys
            100                 105                 110

<210> SEQ ID NO 11
<211> LENGTH: 333
<212> TYPE: DNA
<213> ORGANISM: Artificial Sequence
<220> FEATURE:
<223> OTHER INFORMATION: Synthetic sequence (Anti-CD28 VK3)
<220> FEATURE:
<221> NAME/KEY: CDS
<222> LOCATION: (1)..(333)

<400> SEQUENCE: 11 gac atc gag ctc act cag tct cca gat tct ttg gct gtg tct cta ggg      48
Asp Ile Glu Leu Thr Gln Ser Pro Asp Ser Leu Ala Val Ser Leu Gly
1               5                   10                  15 gag aga gcc acc atc aac tgc aga gcc agt gag agt gtt gaa tat tat      96
Glu Arg Ala Thr Ile Asn Cys Arg Ala Ser Glu Ser Val Glu Tyr Tyr
            20                  25                  30 gtc aca agt tta atg cag tgg tac cag cag aag cca gga cag cca ccc     144
Val Thr Ser Leu Met Gln Trp Tyr Gln Gln Lys Pro Gly Gln Pro Pro
        35                  40                  45 aaa ctc ctc atc ttt gct gca tcc aac gta gaa tct ggg gtc cct gac     192
Lys Leu Leu Ile Phe Ala Ala Ser Asn Val Glu Ser Gly Val Pro Asp
    50                  55                  60 agg ttt agt ggc agt ggg tct ggg aca gac ttc acc ctc acc atc tct     240
Arg Phe Ser Gly Ser Gly Ser Gly Thr Asp Phe Thr Leu Thr Ile Ser
65                  70                  75                  80 tct ctg cag gcc gag gat gtt gca atg tat ttc tgt cag caa agt agg     288
Ser Leu Gln Ala Glu Asp Val Ala Met Tyr Phe Cys Gln Gln Ser Arg
                85                  90                  95 aag gtt cct tac acg ttc gga ggg ggg acc aag gtg gaa ata aaa         333
Lys Val Pro Tyr Thr Phe Gly Gly Gly Thr Lys Val Glu Ile Lys
            100                 105                 110

<210> SEQ ID NO 12
<211> LENGTH: 111
<212> TYPE: PRT
<213> ORGANISM: Artificial Sequence
<220> FEATURE:

<223> OTHER INFORMATION: Synthetic Construct

<400> SEQUENCE: 12

```
Asp Ile Glu Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Asp
50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Met Tyr Phe Cys Gln Gln Ser Arg
                85                  90                  95

Lys Val Pro Tyr Thr Phe Gly Gly Gly Thr Lys Val Glu Ile Lys
            100                 105                 110
```

<210> SEQ ID NO 13
<211> LENGTH: 984
<212> TYPE: DNA
<213> ORGANISM: Artificial Sequence
<220> FEATURE:
<223> OTHER INFORMATION: Synthetic sequence (modified constant heavy sequence)
<220> FEATURE:
<221> NAME/KEY: CDS
<222> LOCATION: (1)..(984)

<400> SEQUENCE: 13

```
gct tcc acc aag ggc cca tcc gtc ttc ccc ctg gcg ccc tgc tcc agg      48
Ala Ser Thr Lys Gly Pro Ser Val Phe Pro Leu Ala Pro Cys Ser Arg
1               5                   10                  15 agc acc tcc gag agc aca gcc gcc ctg ggc tgc ctg gtc aag gac tac      96
Ser Thr Ser Glu Ser Thr Ala Ala Leu Gly Cys Leu Val Lys Asp Tyr
            20                  25                  30 ttc ccc gaa ccg gtg acg gtg tcg tgg aac tca ggc gcc ctg acc agc     144
Phe Pro Glu Pro Val Thr Val Ser Trp Asn Ser Gly Ala Leu Thr Ser
        35                  40                  45 ggc gtg cac acc ttc ccg gct gtc cta cag tcc tca gga ctc tac tcc     192
Gly Val His Thr Phe Pro Ala Val Leu Gln Ser Ser Gly Leu Tyr Ser
    50                  55                  60 ctc agc agc gtg gtg acc gtg ccc tcc agc agc ttg ggc acg aag acc     240
Leu Ser Ser Val Val Thr Val Pro Ser Ser Ser Leu Gly Thr Lys Thr
65                  70                  75                  80 tac acc tgc aat gta gat cac aag ccc agc aac acc aag gtg gac aag     288
Tyr Thr Cys Asn Val Asp His Lys Pro Ser Asn Thr Lys Val Asp Lys
                85                  90                  95 aga gtt gag tcc aaa tat ggt ccc cca tgc cca cca tgc cca gca cct     336
Arg Val Glu Ser Lys Tyr Gly Pro Pro Cys Pro Pro Cys Pro Ala Pro
            100                 105                 110 gag ttc gag ggg gga cca tca gtc ttc ctg ttc ccc cca aaa ccc aag     384
Glu Phe Glu Gly Gly Pro Ser Val Phe Leu Phe Pro Pro Lys Pro Lys
        115                 120                 125 gac act ctc atg atc tcc cgg acc cct gag gtc acg tgc gtg gtg gtg     432
Asp Thr Leu Met Ile Ser Arg Thr Pro Glu Val Thr Cys Val Val Val
    130                 135                 140 gac gtg agc cag gaa gac ccc gag gtc cag ttc aac tgg tac gtg gat     480
Asp Val Ser Gln Glu Asp Pro Glu Val Gln Phe Asn Trp Tyr Val Asp
145                 150                 155                 160
```

```
ggc gtg gag gtg cat aat gcc aag aca aag ccg cgg gag gag cag ttc    528
Gly Val Glu Val His Asn Ala Lys Thr Lys Pro Arg Glu Glu Gln Phe
                165                 170                 175 aac agc acg tac cgt gtg gtc agc gtc ctc acc gtc ctg cac cag gac    576
Asn Ser Thr Tyr Arg Val Val Ser Val Leu Thr Val Leu His Gln Asp
            180                 185                 190 tgg ctg aac ggc aag gag tac aag tgc aag gtc tcc aac aaa ggc ctc    624
Trp Leu Asn Gly Lys Glu Tyr Lys Cys Lys Val Ser Asn Lys Gly Leu
        195                 200                 205 ccg tcc tcc atc gag aaa acc atc tcc aaa gcc aaa ggg cag ccc cga    672
Pro Ser Ser Ile Glu Lys Thr Ile Ser Lys Ala Lys Gly Gln Pro Arg
    210                 215                 220 gag cca cag gtg tac acc ctg ccc cca tcc cag gag gag atg acc aag    720
Glu Pro Gln Val Tyr Thr Leu Pro Pro Ser Gln Glu Glu Met Thr Lys
225                 230                 235                 240 aac cag gtc agc ctg acc tgc ctg gtc aaa ggc ttc tac ccc agc gac    768
Asn Gln Val Ser Leu Thr Cys Leu Val Lys Gly Phe Tyr Pro Ser Asp
                245                 250                 255 atc gcc gtg gag tgg gag agc aat ggg cag ccg gag aac aac tac aag    816
Ile Ala Val Glu Trp Glu Ser Asn Gly Gln Pro Glu Asn Asn Tyr Lys
            260                 265                 270 acc acg cct ccc gtg ctg gac tcc gac ggc tcc ttc ttc ctc tac agc    864
Thr Thr Pro Pro Val Leu Asp Ser Asp Gly Ser Phe Phe Leu Tyr Ser
        275                 280                 285 agg cta acc gtg gac aag agc agg tgg cag gag ggg aat gtc ttc tca    912
Arg Leu Thr Val Asp Lys Ser Arg Trp Gln Glu Gly Asn Val Phe Ser
    290                 295                 300 tgc tcc gtg atg cat gag gct ctg cac aac cac tac aca cag aag agc    960
Cys Ser Val Met His Glu Ala Leu His Asn His Tyr Thr Gln Lys Ser
305                 310                 315                 320 ctc tgc ctg tct ctg ggt aaa tga                                    984
Leu Cys Leu Ser Leu Gly Lys
                325

<210> SEQ ID NO 14
<211> LENGTH: 327
<212> TYPE: PRT
<213> ORGANISM: Artificial Sequence
<220> FEATURE:
<223> OTHER INFORMATION: Synthetic Construct

<400> SEQUENCE: 14

Ala Ser Thr Lys Gly Pro Ser Val Phe Pro Leu Ala Pro Cys Ser Arg
1               5                   10                  15

Ser Thr Ser Glu Ser Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Leu Gly Thr Lys Thr
65                  70                  75                  80

Tyr Thr Cys Asn Val Asp His Lys Pro Ser Asn Thr Lys Val Asp Lys
                85                  90                  95

Arg Val Glu Ser Lys Tyr Gly Pro Pro Cys Pro Pro Cys Pro Ala Pro
            100                 105                 110

Glu Phe Glu Gly Gly Pro Ser Val Phe Leu Phe Pro Pro Lys Pro Lys
        115                 120                 125

Asp Thr Leu Met Ile Ser Arg Thr Pro Glu Val Thr Cys Val Val Val
```

-continued

```
                130                 135                 140
Asp Val Ser Gln Glu Asp Pro Glu Val Gln Phe Asn Trp Tyr Val Asp
145                 150                 155                 160

Gly Val Glu Val His Asn Ala Lys Thr Lys Pro Arg Glu Glu Gln Phe
                165                 170                 175

Asn Ser Thr Tyr Arg Val Val Ser Val Leu Thr Val Leu His Gln Asp
                180                 185                 190

Trp Leu Asn Gly Lys Glu Tyr Lys Cys Lys Val Ser Asn Lys Gly Leu
            195                 200                 205

Pro Ser Ser Ile Glu Lys Thr Ile Ser Lys Ala Lys Gly Gln Pro Arg
            210                 215                 220

Glu Pro Gln Val Tyr Thr Leu Pro Pro Ser Gln Glu Glu Met Thr Lys
225                 230                 235                 240

Asn Gln Val Ser Leu Thr Cys Leu Val Lys Gly Phe Tyr Pro Ser Asp
                245                 250                 255

Ile Ala Val Glu Trp Glu Ser Asn Gly Gln Pro Glu Asn Asn Tyr Lys
                260                 265                 270

Thr Thr Pro Pro Val Leu Asp Ser Asp Gly Ser Phe Phe Leu Tyr Ser
            275                 280                 285

Arg Leu Thr Val Asp Lys Ser Arg Trp Gln Glu Gly Asn Val Phe Ser
            290                 295                 300

Cys Ser Val Met His Glu Ala Leu His Asn His Tyr Thr Gln Lys Ser
305                 310                 315                 320

Leu Cys Leu Ser Leu Gly Lys
                325
```

<210> SEQ ID NO 15
<211> LENGTH: 324
<212> TYPE: DNA
<213> ORGANISM: Artificial Sequence
<220> FEATURE:
<223> OTHER INFORMATION: Synthetic sequence (constant k Light sequence)
<220> FEATURE:
<221> NAME/KEY: CDS
<222> LOCATION: (1)..(324)

<400> SEQUENCE: 15

```
cga act gtg gct gca cca tct gtc ttc atc ttc ccg cca tct gat gag     48
Arg Thr Val Ala Ala Pro Ser Val Phe Ile Phe Pro Pro Ser Asp Glu
1               5                   10                  15 cag ttg aaa tct gga act gcc tct gtt gtg tgc ctg ctg aat aac ttc     96
Gln Leu Lys Ser Gly Thr Ala Ser Val Val Cys Leu Leu Asn Asn Phe
            20                  25                  30 tat ccc aga gag gcc aaa gta cag tgg aag gtg gat aac gcc ctc caa    144
Tyr Pro Arg Glu Ala Lys Val Gln Trp Lys Val Asp Asn Ala Leu Gln
        35                  40                  45 tcg ggt aac tcc cag gag agt gtc aca gag cag gac agc aag gac agc    192
Ser Gly Asn Ser Gln Glu Ser Val Thr Glu Gln Asp Ser Lys Asp Ser
    50                  55                  60 acc tac agc ctc agc agc acc ctg acg ctg agc aaa gca gac tac gag    240
Thr Tyr Ser Leu Ser Ser Thr Leu Thr Leu Ser Lys Ala Asp Tyr Glu
65                  70                  75                  80 aaa cac aaa gtc tac gcc tgc gaa gtc acc cat cag ggc ctg agc tcg    288
Lys His Lys Val Tyr Ala Cys Glu Val Thr His Gln Gly Leu Ser Ser
                85                  90                  95 ccc gtc aca aag agc ttc aac agg gga gag tgt tag                    324
Pro Val Thr Lys Ser Phe Asn Arg Gly Glu Cys
            100                 105
```

<210> SEQ ID NO 16
<211> LENGTH: 107
<212> TYPE: PRT
<213> ORGANISM: Artificial Sequence
<220> FEATURE:
<223> OTHER INFORMATION: Synthetic Construct

<400> SEQUENCE: 16

```
Arg Thr Val Ala Ala Pro Ser Val Phe Ile Phe Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105
```

<210> SEQ ID NO 17
<211> LENGTH: 360
<212> TYPE: DNA
<213> ORGANISM: Artificial Sequence
<220> FEATURE:
<223> OTHER INFORMATION: Synthetic sequence (humanized non-CD28-binding variable region)
<220> FEATURE:
<221> NAME/KEY: CDS
<222> LOCATION: (1)..(360)

<400> SEQUENCE: 17

```
gag gtg aag ctg cag cag tca gga cct ggc ctg gtg aag ccc tca gag      48
Glu Val Lys Leu Gln Gln Ser Gly Pro Gly Leu Val Lys Pro Ser Glu
1               5                   10                  15 acc ctg tcc ctc act tgt act gtc tct ggg ttt aca ttc agc gac tat      96
Thr Leu Ser Leu Thr Cys Thr Val Ser Gly Phe Thr Phe Ser Asp Tyr
            20                  25                  30 ggt gtt cat tgg att cgc cag cct cca gga aag gga ctg gag tgg atc     144
Gly Val His Trp Ile Arg Gln Pro Pro Gly Lys Gly Leu Glu Trp Ile
        35                  40                  45 gga gta ata tgg gct ggt gga ggc acg aat tat aat tcg gct ctc atg     192
Gly Val Ile Trp Ala Gly Gly Gly Thr Asn Tyr Asn Ser Ala Leu Met
    50                  55                  60 tcc aga gtg acc atc agc gtg gac acc tcc aag aac caa ttt tcc tta     240
Ser Arg Val Thr Ile Ser Val Asp Thr Ser Lys Asn Gln Phe Ser Leu
65                  70                  75                  80 aaa ctg agc agt gtg aca gct gct gac aca gcc gtg tat tac tgt gcc     288
Lys Leu Ser Ser Val Thr Ala Ala Asp Thr Ala Val Tyr Tyr Cys Ala
                85                  90                  95 aga gat aag gga tac tcc gct gcc gct tct atg gac tac tgg ggc caa     336
Arg Asp Lys Gly Tyr Ser Ala Ala Ala Ser Met Asp Tyr Trp Gly Gln
            100                 105                 110 ggc acc ctg gtc acc gtc tcc tca                                     360
Gly Thr Leu Val Thr Val Ser Ser
        115                 120
```

<210> SEQ ID NO 18

```
<211> LENGTH: 120
<212> TYPE: PRT
<213> ORGANISM: Artificial Sequence
<220> FEATURE:
<223> OTHER INFORMATION: Synthetic Construct

<400> SEQUENCE: 18

Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Thr Phe Ser Asp Tyr
            20                  25                  30

Gly Val His Trp Ile Arg Gln Pro Pro Gly Lys Gly Leu Glu Trp Ile
        35                  40                  45

Gly Val Ile Trp Ala Gly Gly Thr Asn Tyr Asn Ser Ala Leu Met
    50                  55                  60

Ser Arg Val Thr Ile Ser Val Asp Thr Ser Lys Asn Gln Phe Ser Leu
65                  70                  75                  80

Lys Leu Ser Ser Val Thr Ala Ala Asp Thr Ala Val Tyr Tyr Cys Ala
                85                  90                  95

Arg Asp Lys Gly Tyr Ser Ala Ala Ala Ser Met Asp Tyr Trp Gly Gln
            100                 105                 110

Gly Thr Leu Val Thr Val Ser Ser
        115                 120

<210> SEQ ID NO 19
<211> LENGTH: 733
<212> TYPE: PRT
<213> ORGANISM: Artificial Sequence
<220> FEATURE:
<223> OTHER INFORMATION: Synthetic sequence (humanized HLA-IgG4HC)

<400> SEQUENCE: 19

Gln Val Gln Leu Thr Arg Glu Gly Ser Gly Ser His Ser Met Arg Tyr
1               5                   10                  15

Phe Phe Thr Ser Val Ser Arg Pro Gly Arg Gly Glu Pro Arg Phe Ile
            20                  25                  30

Ala Val Gly Tyr Val Asp Asp Thr Gln Phe Val Arg Phe Asp Ser Asp
        35                  40                  45

Ala Ala Ser Gln Arg Met Glu Pro Arg Ala Pro Trp Ile Glu Gln Glu
    50                  55                  60

Gly Pro Glu Tyr Trp Asp Gly Glu Thr Arg Lys Val Lys Ala His Ser
65                  70                  75                  80

Gln Thr His Arg Val Asp Leu Gly Thr Leu Arg Gly Tyr Tyr Asn Gln
                85                  90                  95

Ser Glu Ala Gly Ser His Thr Val Gln Arg Met Tyr Gly Cys Asp Val
            100                 105                 110

Gly Ser Asp Trp Arg Phe Leu Arg Gly Tyr His Gln Tyr Ala Tyr Asp
        115                 120                 125

Gly Lys Asp Tyr Ile Ala Leu Lys Glu Asp Leu Arg Ser Trp Thr Ala
    130                 135                 140

Ala Asp Met Ala Ala Gln Thr Thr Lys His Lys Trp Glu Ala Ala His
145                 150                 155                 160

Val Ala Glu Gln Leu Arg Ala Tyr Leu Glu Gly Thr Cys Val Glu Trp
                165                 170                 175

Leu Arg Arg Tyr Leu Glu Asn Gly Lys Glu Thr Leu Gln Arg Thr Asp
            180                 185                 190

Ala Pro Lys Thr His Met Thr His His Ala Val Ser Asp His Glu Ala
```

```
            195                 200                 205
Thr Leu Arg Cys Trp Ala Leu Ser Phe Tyr Pro Ala Glu Ile Thr Leu
    210                 215                 220
Thr Trp Gln Arg Asp Gly Glu Asp Gln Thr Gln Asp Thr Glu Leu Val
225                 230                 235                 240
Glu Thr Arg Pro Ala Gly Asp Gly Thr Phe Gln Lys Trp Ala Ala Val
                245                 250                 255
Val Val Pro Ser Gly Gln Glu Gln Arg Tyr Thr Cys His Val Gln His
            260                 265                 270
Glu Gly Leu Pro Lys Pro Leu Thr Trp Ala Arg Glu Val Ser Glu Val
        275                 280                 285
Lys Leu Gln Gln Ser Gly Pro Gly Leu Val Lys Pro Ser Glu Thr Leu
    290                 295                 300
Ser Leu Thr Cys Thr Val Ser Gly Phe Thr Phe Ser Asp Tyr Gly Val
305                 310                 315                 320
His Trp Ile Arg Gln Pro Pro Gly Lys Gly Leu Glu Trp Ile Gly Val
                325                 330                 335
Ile Trp Ala Gly Gly Gly Thr Asn Tyr Asn Ser Ala Leu Met Ser Arg
            340                 345                 350
Val Thr Ile Ser Val Asp Thr Ser Lys Asn Gln Phe Ser Leu Lys Leu
        355                 360                 365
Ser Ser Val Thr Ala Ala Asp Thr Ala Val Tyr Tyr Cys Ala Arg Asp
    370                 375                 380
Lys Gly Tyr Ser Ala Ala Ser Met Asp Tyr Trp Gly Gln Gly Thr
385                 390                 395                 400
Leu Val Thr Val Ser Ser Ala Ser Thr Lys Gly Pro Ser Val Phe Pro
                405                 410                 415
Leu Ala Pro Cys Ser Arg Ser Thr Ser Glu Ser Thr Ala Ala Leu Gly
            420                 425                 430
Cys Leu Val Lys Asp Tyr Phe Pro Glu Pro Val Thr Val Ser Trp Asn
        435                 440                 445
Ser Gly Ala Leu Thr Ser Gly Val His Thr Phe Pro Ala Val Leu Gln
    450                 455                 460
Ser Ser Gly Leu Tyr Ser Leu Ser Ser Val Val Thr Val Pro Ser Ser
465                 470                 475                 480
Ser Leu Gly Thr Lys Thr Tyr Thr Cys Asn Val Asp His Lys Pro Ser
                485                 490                 495
Asn Thr Lys Val Asp Lys Arg Val Glu Ser Lys Tyr Gly Pro Pro Cys
            500                 505                 510
Pro Pro Cys Pro Ala Pro Glu Phe Glu Gly Gly Pro Ser Val Phe Leu
        515                 520                 525
Phe Pro Pro Lys Pro Lys Asp Thr Leu Met Ile Ser Arg Thr Pro Glu
    530                 535                 540
Val Thr Cys Val Val Val Asp Val Ser Gln Glu Asp Pro Glu Val Gln
545                 550                 555                 560
Phe Asn Trp Tyr Val Asp Gly Val Glu Val His Asn Ala Lys Thr Lys
                565                 570                 575
Pro Arg Glu Glu Gln Phe Asn Ser Thr Tyr Arg Val Val Ser Val Leu
            580                 585                 590
Thr Val Leu His Gln Asp Trp Leu Asn Gly Lys Glu Tyr Lys Cys Lys
        595                 600                 605
Val Ser Asn Lys Gly Leu Pro Ser Ser Ile Glu Lys Thr Ile Ser Lys
    610                 615                 620
```

Ala Lys Gly Gln Pro Arg Glu Pro Gln Val Tyr Thr Leu Pro Pro Ser
625                 630                 635                 640

Gln Glu Glu Met Thr Lys Asn Gln Val Ser Leu Thr Cys Leu Val Lys
            645                 650                 655

Gly Phe Tyr Pro Ser Asp Ile Ala Val Glu Trp Glu Ser Asn Gly Gln
        660                 665                 670

Pro Glu Asn Asn Tyr Lys Thr Thr Pro Pro Val Leu Asp Ser Asp Gly
    675                 680                 685

Ser Phe Phe Leu Tyr Ser Arg Leu Thr Val Asp Lys Ser Arg Trp Gln
690                 695                 700

Glu Gly Asn Val Phe Ser Cys Ser Val Met His Glu Ala Leu His Asn
705                 710                 715                 720

His Tyr Thr Gln Lys Ser Leu Ser Leu Ser Leu Gly Lys
                725                 730

<210> SEQ ID NO 20
<211> LENGTH: 218
<212> TYPE: PRT
<213> ORGANISM: Artificial Sequence
<220> FEATURE:
<223> OTHER INFORMATION: Synthetic sequence (Light Chain 3 (LC3 or Vk3))

<400> SEQUENCE: 20

Asp Ile Glu Leu Thr Gln Ser Pro Asp Ser Leu Ala Val Ser Leu Gly
1               5                   10                  15

Glu Arg Ala Thr Ile Asn Cys Arg Ala Ser Glu Ser Val Glu Tyr Tyr
            20                  25                  30

Val Thr Ser Leu Met Gln Trp Tyr Gln Gln Lys Pro Gly Gln Pro Pro
        35                  40                  45

Lys Leu Leu Ile Phe Ala Ala Ser Asn Val Glu Ser Gly Val Pro Asp
    50                  55                  60

Arg Phe Ser Gly Ser Gly Ser Gly Thr Asp Phe Thr Leu Thr Ile Ser
65                  70                  75                  80

Ser Leu Gln Ala Glu Asp Val Ala Met Tyr Phe Cys Gln Gln Ser Arg
                85                  90                  95

Lys Val Pro Tyr Thr Phe Gly Gly Gly Thr Lys Val Glu Ile Lys Arg
            100                 105                 110

Thr Val Ala Ala Pro Ser Val Phe Ile Phe Pro Pro Ser Asp Glu Gln
        115                 120                 125

Leu Lys Ser Gly Thr Ala Ser Val Val Cys Leu Leu Asn Asn Phe Tyr
    130                 135                 140

Pro Arg Glu Ala Lys Val Gln Trp Lys Val Asp Asn Ala Leu Gln Ser
145                 150                 155                 160

Gly Asn Ser Gln Glu Ser Val Thr Glu Gln Asp Ser Lys Asp Ser Thr
                165                 170                 175

Tyr Ser Leu Ser Ser Thr Leu Thr Leu Ser Lys Ala Asp Tyr Glu Lys
            180                 185                 190

His Lys Val Tyr Ala Cys Glu Val Thr His Gln Gly Leu Ser Ser Pro
        195                 200                 205

Val Thr Lys Ser Phe Asn Arg Gly Glu Cys
    210                 215

<210> SEQ ID NO 21
<211> LENGTH: 447
<212> TYPE: PRT
<213> ORGANISM: Artificial Sequence
<220> FEATURE:
<223> OTHER INFORMATION: Synthetic sequence (Heavy Chain 1 (HC1))

<400> SEQUENCE: 21

| | | | | | | | | | | | | | | |
|---|---|---|---|---|---|---|---|---|---|---|---|---|---|---|
| Glu | Val | Lys | Leu | Gln | Gln | Ser | Gly | Pro | Gly | Leu | Val | Lys | Pro | Ser | Glu |
| 1 | | | | 5 | | | | | 10 | | | | | 15 | |
| Thr | Leu | Ser | Leu | Thr | Cys | Thr | Val | Ser | Gly | Phe | Ser | Leu | Ser | Asp | Tyr |
| | | | 20 | | | | | 25 | | | | | 30 | | |
| Gly | Val | His | Trp | Val | Arg | Gln | Ala | Pro | Gly | Lys | Gly | Leu | Glu | Trp | Leu |
| | | 35 | | | | | 40 | | | | | 45 | | | |
| Gly | Val | Ile | Trp | Ala | Gly | Gly | Thr | Asn | Tyr | Asn | Ser | Ala | Leu | Met | |
| | 50 | | | | | 55 | | | | | 60 | | | | |
| Ser | Arg | Lys | Thr | Ile | Ser | Lys | Asp | Asn | Ser | Lys | Ser | Gln | Val | Phe | Leu |
| 65 | | | | | 70 | | | | | 75 | | | | | 80 |
| Lys | Met | Asn | Ser | Leu | Thr | Ala | Ala | Asp | Thr | Ala | Val | Tyr | Tyr | Cys | Ala |
| | | | | 85 | | | | | 90 | | | | | 95 | |
| Arg | Asp | Lys | Gly | Tyr | Ser | Tyr | Tyr | Ser | Met | Asp | Tyr | Trp | Gly | Gln | |
| | | | 100 | | | | | 105 | | | | | 110 | | |
| Gly | Thr | Leu | Val | Thr | Val | Ser | Ser | Ala | Ser | Thr | Lys | Gly | Pro | Ser | Val |
| | | | 115 | | | | | 120 | | | | | 125 | | |
| Phe | Pro | Leu | Ala | Pro | Cys | Ser | Arg | Ser | Thr | Ser | Glu | Ser | Thr | Ala | Ala |
| | 130 | | | | | 135 | | | | | 140 | | | | |
| Leu | Gly | Cys | Leu | Val | Lys | Asp | Tyr | Phe | Pro | Glu | Pro | Val | Thr | Val | Ser |
| 145 | | | | | 150 | | | | | 155 | | | | | 160 |
| Trp | Asn | Ser | Gly | Ala | Leu | Thr | Ser | Gly | Val | His | Thr | Phe | Pro | Ala | Val |
| | | | | 165 | | | | | 170 | | | | | 175 | |
| Leu | Gln | Ser | Ser | Gly | Leu | Tyr | Ser | Leu | Ser | Ser | Val | Val | Thr | Val | Pro |
| | | | 180 | | | | | 185 | | | | | 190 | | |
| Ser | Ser | Ser | Leu | Gly | Thr | Lys | Thr | Tyr | Thr | Cys | Asn | Val | Asp | His | Lys |
| | | | 195 | | | | | 200 | | | | | 205 | | |
| Pro | Ser | Asn | Thr | Lys | Val | Asp | Lys | Arg | Val | Glu | Ser | Lys | Tyr | Gly | Pro |
| | 210 | | | | | 215 | | | | | 220 | | | | |
| Pro | Cys | Pro | Pro | Cys | Pro | Ala | Pro | Glu | Phe | Glu | Gly | Gly | Pro | Ser | Val |
| 225 | | | | | 230 | | | | | 235 | | | | | 240 |
| Phe | Leu | Phe | Pro | Pro | Lys | Pro | Lys | Asp | Thr | Leu | Met | Ile | Ser | Arg | Thr |
| | | | | 245 | | | | | 250 | | | | | 255 | |
| Pro | Glu | Val | Thr | Cys | Val | Val | Asp | Val | Ser | Gln | Glu | Asp | Pro | Glu | |
| | | | 260 | | | | | 265 | | | | | 270 | | |
| Val | Gln | Phe | Asn | Trp | Tyr | Val | Asp | Gly | Val | Glu | Val | His | Asn | Ala | Lys |
| | | | 275 | | | | | 280 | | | | | 285 | | |
| Thr | Lys | Pro | Arg | Glu | Glu | Gln | Phe | Asn | Ser | Thr | Tyr | Arg | Val | Val | Ser |
| | 290 | | | | | 295 | | | | | 300 | | | | |
| Val | Leu | Thr | Val | Leu | His | Gln | Asp | Trp | Leu | Asn | Gly | Lys | Glu | Tyr | Lys |
| 305 | | | | | 310 | | | | | 315 | | | | | 320 |
| Cys | Lys | Val | Ser | Asn | Lys | Gly | Leu | Pro | Ser | Ser | Ile | Glu | Lys | Thr | Ile |
| | | | | 325 | | | | | 330 | | | | | 335 | |
| Ser | Lys | Ala | Lys | Gly | Gln | Pro | Arg | Glu | Pro | Gln | Val | Tyr | Thr | Leu | Pro |
| | | | 340 | | | | | 345 | | | | | 350 | | |
| Pro | Ser | Gln | Glu | Glu | Met | Thr | Lys | Asn | Gln | Val | Ser | Leu | Thr | Cys | Leu |
| | | | 355 | | | | | 360 | | | | | 365 | | |
| Val | Lys | Gly | Phe | Tyr | Pro | Ser | Asp | Ile | Ala | Val | Glu | Trp | Glu | Ser | Asn |
| | 370 | | | | | 375 | | | | | 380 | | | | |
| Gly | Gln | Pro | Glu | Asn | Asn | Tyr | Lys | Thr | Thr | Pro | Pro | Val | Leu | Asp | Ser |
| 385 | | | | | 390 | | | | | 395 | | | | | 400 |

Asp Gly Ser Phe Phe Leu Tyr Ser Arg Leu Thr Val Asp Lys Ser Arg
            405                 410                 415

Trp Gln Glu Gly Asn Val Phe Ser Cys Ser Val Met His Glu Ala Leu
            420                 425                 430

His Asn His Tyr Thr Gln Lys Ser Leu Cys Leu Ser Leu Gly Lys
            435                 440                 445

<210> SEQ ID NO 22
<211> LENGTH: 447
<212> TYPE: PRT
<213> ORGANISM: Artificial Sequence
<220> FEATURE:
<223> OTHER INFORMATION: Synthetic sequence (Heavy Chain 2 (HC2))

<400> SEQUENCE: 22

Glu Val Lys Leu Gln Gln Ser Gly Pro Gly Leu Val Lys Pro Ser Glu
1               5                   10                  15

Thr Leu Ser Leu Thr Cys Thr Val Ser Gly Phe Ser Leu Ser Asp Tyr
            20                  25                  30

Gly Val His Trp Val Arg Gln Ala Pro Gly Lys Gly Leu Glu Trp Leu
            35                  40                  45

Gly Val Ile Trp Ala Gly Gly Thr Asn Tyr Asn Ser Ala Leu Met
    50                  55                  60

Ser Arg Lys Thr Ile Ser Lys Asp Asn Ser Lys Ser Gln Val Ser Leu
65                  70                  75                  80

Lys Met Ser Ser Val Thr Ala Ala Asp Thr Ala Val Tyr Tyr Cys Ala
                85                  90                  95

Arg Asp Lys Gly Tyr Ser Tyr Tyr Ser Met Asp Tyr Trp Gly Gln
            100                 105                 110

Gly Thr Leu Val Thr Val Ser Ser Ala Ser Thr Lys Gly Pro Ser Val
            115                 120                 125

Phe Pro Leu Ala Pro Cys Ser Arg Ser Thr Ser Glu Ser Thr Ala Ala
    130                 135                 140

Leu Gly Cys Leu Val Lys Asp Tyr Phe Pro Glu Pro Val Thr Val Ser
145                 150                 155                 160

Trp Asn Ser Gly Ala Leu Thr Ser Gly Val His Thr Phe Pro Ala Val
                165                 170                 175

Leu Gln Ser Ser Gly Leu Tyr Ser Leu Ser Ser Val Val Thr Val Pro
            180                 185                 190

Ser Ser Ser Leu Gly Thr Lys Thr Tyr Thr Cys Asn Val Asp His Lys
            195                 200                 205

Pro Ser Asn Thr Lys Val Asp Lys Arg Val Glu Ser Lys Tyr Gly Pro
    210                 215                 220

Pro Cys Pro Pro Cys Pro Ala Pro Glu Phe Glu Gly Gly Pro Ser Val
225                 230                 235                 240

Phe Leu Phe Pro Pro Lys Pro Lys Asp Thr Leu Met Ile Ser Arg Thr
                245                 250                 255

Pro Glu Val Thr Cys Val Val Val Asp Val Ser Gln Glu Asp Pro Glu
            260                 265                 270

Val Gln Phe Asn Trp Tyr Val Asp Gly Val Glu Val His Asn Ala Lys
            275                 280                 285

Thr Lys Pro Arg Glu Glu Gln Phe Asn Ser Thr Tyr Arg Val Val Ser
    290                 295                 300

Val Leu Thr Val Leu His Gln Asp Trp Leu Asn Gly Lys Glu Tyr Lys
305                 310                 315                 320

-continued

```
Cys Lys Val Ser Asn Lys Gly Leu Pro Ser Ser Ile Glu Lys Thr Ile
                325                 330                 335

Ser Lys Ala Lys Gly Gln Pro Arg Glu Pro Gln Val Tyr Thr Leu Pro
            340                 345                 350

Pro Ser Gln Glu Glu Met Thr Lys Asn Gln Val Ser Leu Thr Cys Leu
        355                 360                 365

Val Lys Gly Phe Tyr Pro Ser Asp Ile Ala Val Glu Trp Glu Ser Asn
370                 375                 380

Gly Gln Pro Glu Asn Asn Tyr Lys Thr Thr Pro Pro Val Leu Asp Ser
385                 390                 395                 400

Asp Gly Ser Phe Phe Leu Tyr Ser Arg Leu Thr Val Asp Lys Ser Arg
                405                 410                 415

Trp Gln Glu Gly Asn Val Phe Ser Cys Ser Val Met His Glu Ala Leu
            420                 425                 430

His Asn His Tyr Thr Gln Lys Ser Leu Cys Leu Ser Leu Gly Lys
        435                 440                 445

<210> SEQ ID NO 23
<211> LENGTH: 5
<212> TYPE: PRT
<213> ORGANISM: Artificial Sequence
<220> FEATURE:
<223> OTHER INFORMATION: Synthetic sequence

<400> SEQUENCE: 23

Asp Tyr Gly Val His
1               5

<210> SEQ ID NO 24
<211> LENGTH: 16
<212> TYPE: PRT
<213> ORGANISM: Artificial Sequence
<220> FEATURE:
<223> OTHER INFORMATION: Synthetic sequence

<400> SEQUENCE: 24

Val Ile Trp Ala Gly Gly Gly Thr Asn Tyr Asn Ser Ala Leu Met Ser
1               5                   10                  15

<210> SEQ ID NO 25
<211> LENGTH: 12
<212> TYPE: PRT
<213> ORGANISM: Artificial Sequence
<220> FEATURE:
<223> OTHER INFORMATION: Synthetic sequence

<400> SEQUENCE: 25

Asp Lys Gly Tyr Ser Tyr Tyr Tyr Ser Met Asp Tyr
1               5                   10

<210> SEQ ID NO 26
<211> LENGTH: 15
<212> TYPE: PRT
<213> ORGANISM: Artificial Sequence
<220> FEATURE:
<223> OTHER INFORMATION: Synthetic sequence

<400> SEQUENCE: 26

Arg Ala Ser Glu Ser Val Glu Tyr Tyr Val Thr Ser Leu Met Gln
1               5                   10                  15

<210> SEQ ID NO 27
```

<211> LENGTH: 7
<212> TYPE: PRT
<213> ORGANISM: Artificial Sequence
<220> FEATURE:
<223> OTHER INFORMATION: Synthetic sequence

<400> SEQUENCE: 27

Ala Ala Ser Asn Val Glu Ser
1               5

<210> SEQ ID NO 28
<211> LENGTH: 9
<212> TYPE: PRT
<213> ORGANISM: Artificial Sequence
<220> FEATURE:
<223> OTHER INFORMATION: Synthetic sequence

<400> SEQUENCE: 28

Gln Gln Ser Arg Lys Val Pro Tyr Thr
1               5

<210> SEQ ID NO 29
<211> LENGTH: 5
<212> TYPE: PRT
<213> ORGANISM: Artificial Sequence
<220> FEATURE:
<223> OTHER INFORMATION: Synthetic sequence

<400> SEQUENCE: 29

Gly Gly Gly Ser Gly
1               5

<210> SEQ ID NO 30
<211> LENGTH: 5
<212> TYPE: PRT
<213> ORGANISM: Artificial Sequence
<220> FEATURE:
<223> OTHER INFORMATION: Synthetic sequence

<400> SEQUENCE: 30

Ala Ala Ala Gly Gly
1               5

<210> SEQ ID NO 31
<211> LENGTH: 51
<212> TYPE: DNA
<213> ORGANISM: Artificial Sequence
<220> FEATURE:
<223> OTHER INFORMATION: Synthetic sequence (N-terminal linker)
<220> FEATURE:
<221> NAME/KEY: CDS
<222> LOCATION: (1)..(51)

<400> SEQUENCE: 31 cag gtc caa ctg acg cgt gag ggg tcc ggc tct cac tcc atg agg tat    48
Gln Val Gln Leu Thr Arg Glu Gly Ser Gly Ser His Ser Met Arg Tyr
1               5                   10                  15 ttc                                                                51
Phe

<210> SEQ ID NO 32
<211> LENGTH: 17
<212> TYPE: PRT
<213> ORGANISM: Artificial Sequence
<220> FEATURE:
<223> OTHER INFORMATION: Synthetic Construct

<400> SEQUENCE: 32

```
Gln Val Gln Leu Thr Arg Glu Gly Ser Gly Ser His Ser Met Arg Tyr
1               5                   10                  15
Phe

<210> SEQ ID NO 33
<211> LENGTH: 57
<212> TYPE: DNA
<213> ORGANISM: Artificial Sequence
<220> FEATURE:
<223> OTHER INFORMATION: Synthetic sequence (C-terminal linker)
<220> FEATURE:
<221> NAME/KEY: CDS
<222> LOCATION: (1)..(57)

<400> SEQUENCE: 33 gag ggt ttg ccc aag ccc ctc acc tgg gct cga gag gtg agc gag gtc        48
Glu Gly Leu Pro Lys Pro Leu Thr Trp Ala Arg Glu Val Ser Glu Val
1               5                   10                  15 aag ctg cag                                                            57
Lys Leu Gln <210> SEQ ID NO 34
<211> LENGTH: 19
<212> TYPE: PRT
<213> ORGANISM: Artificial Sequence
<220> FEATURE:
<223> OTHER INFORMATION: Synthetic Construct

<400> SEQUENCE: 34

Glu Gly Leu Pro Lys Pro Leu Thr Trp Ala Arg Glu Val Ser Glu Val
1               5                   10                  15

Lys Leu Gln
```

The invention claimed is:

1. A method of treating cancer, comprising:
administering to a cancer patient, either during, concomitantly, or after therapy with one or more checkpoint inhibitors, a composition comprising a nano-scale artificial antigen presenting cell (aAPC) comprising:
a nanoparticle having an average diameter of less than about 400 nm, comprising a hydrophilic sheath formed from polyethylene glycol (PEG) chains;
a population of anti-CD28 T cell costimulatory ligands on the surface of the nanoparticle; and
a population of MHC Class I antigen presenting complex ligands on the surface of the nanoparticle, wherein a tumor-associated antigenic peptide is bound to the MHC Class I antigen binding cleft; and wherein the costimulatory ligands and MHC class I antigen presenting complex ligands are attached to terminal ends of the PEG chains.

2. The method of claim 1, wherein the cancer is a carcinoma.

3. The method of claim 1, wherein the cancer is a melanoma.

4. The method of claim 1, wherein the cancer is a lung cancer.

5. The method of claim 1, wherein the cancer is a lymphoma.

6. The method of claim 1, wherein the cancer is non-small cell lung carcinoma.

7. The method of claim 1, wherein the cancer is a head and neck cancer.

8. The method of claim 1, wherein the cancer is a renal cancer.

9. The method of claim 1, wherein the checkpoint inhibitor is selected from an anti-CTLA4, or an anti-PD1, or an anti-PD-L1 antibody.

10. The method of claim 1, wherein the checkpoint inhibitor is an anti-PD1 antibody.

11. The method of claim 1, wherein the checkpoint inhibitor is an anti-PD-L1 antibody.

12. The method of claim 1, wherein the checkpoint inhibitor is selected from Nivolumab, Pembrolizumab, and Ipilimumab.

13. The method of claim 1, wherein the nanoparticles have a size in the range of about 20 to 200 nm.

14. The method of claim 13, wherein the nanoparticles have a size in the range of about 100 to 200 nm.

15. The method of claim 1, wherein the nano-aAPC is administered after about 1 to 8 weeks of checkpoint inhibitor therapy.

16. The method of claim 15, wherein the nano-aAPC is administered after about 2 to 4 weeks of checkpoint inhibitor therapy.

17. The method of claim 1, wherein the nano-aAPC is administered about once every four weeks.

18. The method of claim 1, wherein the nano-aAPC is administered about once every two weeks.

19. The method of claim 1, wherein the nano-aAPC is administered concomitantly with the checkpoint inhibitor therapy.

20. The method of claim 1, wherein the patient received the checkpoint inhibitor therapy, and was resistant, only partially responsive, or transiently responsive to the checkpoint inhibitor therapy.

21. The method of claim 1, wherein the nanoparticle comprises a PLGA or PLA polymer core and wherein the polymer core is based on 1:0 to 1:1 Lactic Acid:Glycolic Acid ratio.

22. The method of claim 1, wherein the nanoparticle comprises a PLGA polymer core having about 1:1 Lactic Acid:Glycolic Acid.

23. The method of claim 1, wherein the nanoparticle comprises a PLGA or PLA polymer core and the core polymer has a molecular weight of from about 10K to about 50K.

24. The method of claim 1, wherein the nanoparticle comprises a PLGA or PLA polymer core, and PLGA-PEG and/or PLA-PEG block co-polymers, the PEG portion forming the hydrophilic shell.

25. The method of claim 24, wherein the polypeptide ligands are attached through functional groups at the PEG terminus.

26. The method of claim 1, wherein the nanoparticle comprises a PLGA or PLA polymer core and wherein the PLA-PEG co-polymer contains a PLA portion having a molecular weight of from about 10K to about 50K, and a PEG portion having molecular weight(s) of from about 2K to about 10K, or wherein the PLGA-PEG co-polymer contains a PLGA portion having molecular weight of from about 10K to about 50K, and a PEG portion having molecular weight(s) of from about 2K to about 10K.

27. The method of claim 26, wherein the PLA portion of the PLA-PEG has a molecular weight of about 20K, and the PEG portion has a molecular weight of about 3K and/or about 5K, or wherein the PLGA-PEG has a molecular weight of about 20K, and the PEG portion has a molecular weight of about 3K and/or about 5K.

28. The method of claim 1, wherein the population of MHC Class I antigen presenting complexes comprise an HLA amino acid sequence fused to each of two immunoglobulin sequences, each immunoglobulin sequence having a partial heavy chain sequence of a CH2 and CH3 domain and a hinge region, in the absence of a variable domain sequence and in the absence of a light chain sequence, wherein the HLA amino acid sequences are fused to the hinge regions.

* * * * *